(12) United States Patent
Manhas et al.

(10) Patent No.: US 12,342,808 B2
(45) Date of Patent: *Jul. 1, 2025

(54) COMPOSITIONS, DEVICES AND METHODS FOR CONTROL OF PESTS USING VAPOR ACTIVITY

(71) Applicant: 0903608 B.C. Ltd., Vancouver (CA)

(72) Inventors: Karan Manhas, Vancouver (CA); Annett Rozek, Port Moody (CA); Nathan Woodbury, Burnaby (CA); Shannon Lentz, Vancouver (CA); Robert James Etsu Takeuchi, Vancouver (CA); Sasha Ozeroff, Vancouver (CA)

(73) Assignee: 0903608 B.C. Ltd., Vancouver (CA)

( * ) Notice: Subject to any disclaimer, the term of this patent is extended or adjusted under 35 U.S.C. 154(b) by 514 days.

This patent is subject to a terminal disclaimer.

(21) Appl. No.: 15/037,513

(22) PCT Filed: Nov. 18, 2014

(86) PCT No.: PCT/IB2014/066139
§ 371 (c)(1),
(2) Date: May 18, 2016

(87) PCT Pub. No.: WO2015/071890
PCT Pub. Date: May 21, 2015

(65) Prior Publication Data
US 2016/0286782 A1    Oct. 6, 2016

Related U.S. Application Data

(60) Provisional application No. 62/008,425, filed on Jun. 5, 2014, provisional application No. 61/941,049, filed on Feb. 18, 2014, provisional application No. 61/918,641, filed on Dec. 19, 2013, provisional application No. 61/913,194, filed on Dec. 6, 2013, provisional application No. 61/911,434, filed on Dec. 3, 2013, provisional application No. 61/905,415, filed on Nov. 18, 2013.

(51) Int. Cl.
| | | |
|---|---|---|
| A01M 13/00 | (2006.01) | |
| A01M 1/20 | (2006.01) | |
| A01M 17/00 | (2006.01) | |
| A01N 25/18 | (2006.01) | |
| A61K 31/12 | (2006.01) | |

(52) U.S. Cl.
CPC ........ *A01M 13/003* (2013.01); *A01M 1/2022* (2013.01); *A01M 1/2027* (2013.01); *A01M 1/2033* (2013.01); *A01M 1/2044* (2013.01); *A01M 1/2055* (2013.01); *A01M 1/2061* (2013.01); *A01M 1/2077* (2013.01); *A01M 17/008* (2013.01); *A01N 25/18* (2013.01); *A61K 31/12* (2013.01); *A01M 2200/011* (2013.01)

(58) Field of Classification Search
CPC .............. A01M 13/003; A01M 1/2022; A01M 1/2027; A01M 1/2033; A01M 1/2044; A01M 1/2055; A01M 1/2061; A01M 1/2077; A01M 17/008; A01M 2200/011; A01N 25/18; A61K 31/12; A61P 9/14
See application file for complete search history.

(56) References Cited

U.S. PATENT DOCUMENTS

| | | |
|---|---|---|
| 1,003,393 A | 9/1911 | Bauer |
| 2,058,177 A | 10/1936 | Raff |
| 2,396,054 A | 3/1946 | McKim |
| 2,793,154 A | 5/1957 | Shillitoe et al. |
| 2,897,112 A | 7/1959 | Hartford et al. |
| 2,979,268 A * | 4/1961 | Brun ........................ A61L 9/03 239/55 |
| 3,169,705 A | 2/1965 | Geiger |
| 3,630,446 A | 12/1971 | Roth |
| 3,771,254 A | 11/1973 | Scott |
| 3,996,348 A | 12/1976 | Greenberg |
| 4,123,518 A | 10/1978 | Behrenz |
| 4,202,472 A | 5/1980 | Lin |
| 4,283,878 A | 8/1981 | Hill et al. |
| 4,400,909 A | 8/1983 | Reese |
| 4,556,562 A | 12/1985 | Larson |
| 4,576,844 A * | 3/1986 | Murray ................... B29C 66/71 428/35.2 |
| 4,804,142 A | 2/1989 | Riley |

(Continued)

FOREIGN PATENT DOCUMENTS

| | | |
|---|---|---|
| CA | 2066527 C | 10/1992 |
| CA | 2068039 A1 | 6/1993 |

(Continued)

OTHER PUBLICATIONS

S. Michaelraj & R.K. Sharma, Fumigant Toxicity of Neem Formulations Against Sitophilus oryzae and Rhyzopertha dominica, 2 J Agricult. Tech. (Year: 2006).*
Gunter Schmal, et al, The Efficacy of Neem Seed Extracts (Tre-san, MiteStop) on a Broad Spectrum of Pests and Parasites, 107 Parasitol. Res. 261 (Year: 2010).*
Samir Tine, et al, Laboratory Evaluation of Azadirachtin Against the Oriental Cockroach, *Blatta orientalis* L. (Dictyoptera, Blattellidae): Insecticidal Activity and Reproductive Effects, 10 AFR. J Biotechnol. 19816 (Year: 2011).*
Gahukar, R.T., "Formulations of neem based products/pesticides", Pestology, 1996, 20(9):44-45.

(Continued)

*Primary Examiner* — Sean M Basquill
(74) *Attorney, Agent, or Firm* — Viridant IP

(57) ABSTRACT

Devices and methods for the control of pests using the vapors of a pesticidal composition. Compostions, devices and methods for the selective control of pests while not harming one or more beneficial insects are also disclosed. In some embodiments, the pests are bed bugs, fleas, lice, ticks, or the like. In some embodiments, the pests are varroa mites and the beneficial insects are honey bees.

26 Claims, 24 Drawing Sheets

(56) References Cited

U.S. PATENT DOCUMENTS

| | | | |
|---|---|---|---|
| 4,817,824 A * | 4/1989 | LaFleur | B65D 90/205 |
| | | | 222/105 |
| 4,923,745 A | 5/1990 | Wolfert | |
| 4,943,434 A | 7/1990 | Lidert | |
| 5,001,146 A | 3/1991 | Carter et al. | |
| 5,060,597 A | 10/1991 | Fredericks | |
| 5,145,604 A | 9/1992 | Neumiller | |
| 5,405,612 A | 4/1995 | Locke et al. | |
| 5,472,700 A | 12/1995 | Staetz et al. | |
| 5,679,662 A | 10/1997 | Chang et al. | |
| 5,738,863 A | 4/1998 | Sackin et al. | |
| 5,792,465 A | 8/1998 | Hagarty | |
| 5,885,600 A | 3/1999 | Blum et al. | |
| 5,900,244 A | 5/1999 | Howse | |
| 5,961,043 A | 10/1999 | Samuelson | |
| 6,294,571 B1 | 9/2001 | Subbaraman et al. | |
| 6,339,897 B1 | 1/2002 | Hayes | |
| 6,610,254 B1 | 8/2003 | Furner | |
| 6,641,827 B2 | 11/2003 | Yoshida et al. | |
| 6,646,014 B2 | 11/2003 | Watkins | |
| 6,703,034 B2 | 3/2004 | Parmar et al. | |
| 6,849,614 B1 | 2/2005 | Bessette | |
| 6,942,835 B2 | 9/2005 | Monblanc | |
| 6,949,587 B1 | 9/2005 | Bessette | |
| 7,381,431 B2 | 6/2008 | Baker et al. | |
| 7,402,302 B2 | 7/2008 | Plato | |
| 7,497,623 B2 | 3/2009 | Thomas | |
| 7,687,533 B2 | 3/2010 | Critcher et al. | |
| 7,955,609 B2 | 6/2011 | Baron et al. | |
| 8,012,554 B2 | 9/2011 | Shelley | |
| 8,105,620 B2 | 1/2012 | Williams | |
| 8,119,150 B2 | 2/2012 | Tamarkin et al. | |
| 8,707,616 B1 | 4/2014 | Black | |
| 9,999,218 B2 * | 6/2018 | Manhas | A01N 25/02 |
| 2003/0168521 A1 | 9/2003 | Skalitzky | |
| 2003/0224939 A1 | 12/2003 | Miles | |
| 2004/0034149 A1* | 2/2004 | Garcia | A01N 65/00 |
| | | | 524/474 |
| 2005/0220374 A1 | 10/2005 | Thomas | |
| 2006/0121073 A1 | 6/2006 | Goyal | |
| 2006/0130391 A1* | 6/2006 | Livingston | A01M 29/12 |
| | | | 43/124 |
| 2006/0276339 A1* | 12/2006 | Windsor | A01N 25/32 |
| | | | 504/127 |
| 2007/0134127 A1 | 6/2007 | Smith | |
| 2008/0250698 A1 | 10/2008 | Chadha | |
| 2008/0269177 A1 | 10/2008 | Bessette | |
| 2009/0235949 A1 | 9/2009 | Ritterband | |
| 2009/0257958 A1 | 10/2009 | Sims | |
| 2010/0120724 A1 | 5/2010 | Bessette | |
| 2010/0158965 A1* | 6/2010 | Beitzel | A01N 25/34 |
| | | | 424/405 |
| 2010/0264232 A1 | 10/2010 | Gruenbacher | |
| 2011/0070308 A1 | 3/2011 | Williams et al. | |
| 2011/0113674 A1 | 5/2011 | Levy | |
| 2011/0164834 A1 | 7/2011 | Stiglic | |
| 2011/0229589 A1 | 9/2011 | Elraz | |
| 2012/0171313 A1 | 7/2012 | Boone | |
| 2012/0181349 A1 | 7/2012 | Adleff | |
| 2013/0295153 A1 | 11/2013 | Miresmailli | |
| 2014/0048614 A1 | 2/2014 | Santini | |
| 2014/0048620 A1 | 2/2014 | Semenov | |
| 2014/0166774 A1 | 6/2014 | Morhain | |
| 2014/0208636 A1 | 7/2014 | Black | |
| 2014/0209698 A1* | 7/2014 | Olchovy | A01M 1/2055 |
| | | | 239/6 |
| 2014/0220164 A1 | 8/2014 | Manhas et al. | |
| 2014/0242138 A1 | 8/2014 | Kritzman | |
| 2014/0242199 A1 | 8/2014 | Manhas et al. | |
| 2014/0335140 A1 | 11/2014 | Hoag | |

FOREIGN PATENT DOCUMENTS

| | | |
|---|---|---|
| CA | 2237484 A1 | 11/1998 |
| CA | 2677936 C | 3/2011 |
| CA | 2849270 A1 | 4/2013 |
| CN | 1276161 C | 12/2000 |
| CN | 1322110 C | 11/2001 |
| CN | 1513319 A | 7/2004 |
| CN | 1633849 A | 7/2005 |
| CN | 101296710 A | 10/2008 |
| CN | 101442908 A | 5/2009 |
| CN | 101448394 A | 6/2009 |
| CN | 101537044 A | 9/2009 |
| CN | 102091337 A | 6/2011 |
| CN | 102171321 A | 8/2011 |
| DE | 1230259 B | 12/1966 |
| DE | 2026119 A1 | 12/1970 |
| DE | 1694240 A1 | 1/1971 |
| DE | 1954501 A1 | 5/1971 |
| DE | 2028226 A1 | 6/1971 |
| DE | 091898 A1 | 8/1972 |
| DE | 2231099 A1 | 1/1974 |
| DE | 2145318 A1 | 8/1974 |
| DE | 8812770 U1 | 11/1988 |
| EP | 0019010 A1 | 11/1980 |
| EP | 0218162 A2 | 4/1987 |
| EP | 494067 A1 | 7/1992 |
| EP | 948892 A1 | 10/1999 |
| EP | 2250904 A1 | 11/2010 |
| GB | 2405340 A | 3/2005 |
| JP | S50-42053 | 4/1975 |
| JP | 63-96101 A | 4/1988 |
| JP | 64-38006 | 2/1989 |
| JP | 4-308511 | 10/1992 |
| JP | 5-139907 A | 6/1993 |
| JP | 6-10122 B2 | 2/1994 |
| JP | 8-267086 | 10/1996 |
| JP | 2000-247809 A | 9/2000 |
| JP | 2000-281509 A | 10/2000 |
| JP | 2001-199807 A | 7/2001 |
| JP | 2002-511391 A | 4/2002 |
| JP | 2002-521406 A | 7/2002 |
| JP | 2003-12411 A | 1/2003 |
| JP | 2005-513053 A2 | 5/2005 |
| JP | 2005-255664 A | 9/2005 |
| JP | 2006-306835 A | 11/2006 |
| JP | 2010-515775 A | 5/2010 |
| JP | 2010-522236 A | 7/2010 |
| JP | 2011-517685 A | 6/2011 |
| TW | 201306740 A1 | 2/2013 |
| WO | 9747193 | 12/1997 |
| WO | 00/05964 A1 | 2/2000 |
| WO | 01/00034 A1 | 1/2001 |
| WO | 03028456 A1 | 4/2003 |
| WO | 2009/038599 A1 | 3/2009 |
| WO | 2009/144712 A2 | 12/2009 |
| WO | 2011029754 A3 | 3/2011 |
| WO | 2012/107266 A1 | 8/2012 |
| WO | 2013050967 A1 | 4/2013 |
| WO | 2013063534 A1 | 5/2013 |

OTHER PUBLICATIONS

Gochev, V., et al., "Chemical composition and antimicrobial activity of Bulgarian peppermint oils", Bulgaria Scientific Papers, 2008, 36(5):83.

Granger Passet, "Thymus vulgaris spontane de France: Races chimiques et chemotaxonomie", Phytochemistry, 1973, 12(7):1683-1691.

Harwood, S.H., et al., "Toxicity of peppermint monoterpenes to the variegated cutworm (Lepidoptera: Noctuidae)", J. Econ. Entomol, 1990, 83:1761-1767.

Hierro, I., et al., "Action of different monoterpenic compounds against Anisakis simplex S.I.L. larvae", Phytomedicine, 2004, 11:77-82.

Hui, L., et al., "Chemical composition of lavender essential oil and its antioxidant activity and inhibition against rhinitis-related bacteria", Afri. J. of Micro. Res., 2010, 4(4):309-313.

(56) References Cited

OTHER PUBLICATIONS

Hummelbrunner, A.L., et al., "Acute, sublethal, antifeedant and synergistic effects of monoterpenoid essential oil compounds on the tobacco cut worm (Lepidoptera: Noctuidae)", J. Agric. Food Chem., 2001, 49:715-720.

Isman, M.B., et al., "Pesticides based on plant essential oils: from traditional practice to commercialization", Naturally Occurring Bioactive Compounds, 2006, 3(2):29-44.

Jones, C. and Fim, R., "Some allelochemicals of Ptteridium aquilinum and their involvement in resistance to Pieris brassicae", Biochem. Syst. Ecol, 1979, 7:187-192.

Karr, L.L. and Coats, J.R., "Effects of four monoterpenoids on growth and reproduction of the German cockroach (Blattodea: Blattellidae)", J. Econ. Entomol, 1992, 85:424-429.

Kaul, P.N., et al., Volatile constituents of essential oils isolated from different parts of cinnamon (*Cinnamomum zeylanicum* Blume), J. Sci. Food Agri., 2003, 83:53-55.

Khattak, M.K., et al., "Repellency and residual effect of neem or mineral oil on the distribution and oviposition of maize weevil, *Sitophilus zeamais* Motsch", Pakistan Journal of Biological Sciences, 2000, 3(12): 2131-2134.

Kim, E.H., et al., "Acaricidal activity of clove bud oil compounds against Dermatophagoides farinae and Dermatophagoides pteronyssinus (Acari: Pyroglyphidae)", J. Agric Food Chem, 2003, 51:885-889.

Kimbaris, A.C., et al., "Quantitative analysis of garlic (*Allium sativum*) oil unsaturated acyclic components using FT-Raman spectroscopy", Food Chemistry, 2006, 94(2):287-295.

Lee, S., et al., "Insecticidal activity of monoterpenoids to western corn root worm (Coleoptera: Chrysomelidae), spotted spidermite (Acari: Tetranychidae) and Housefly (Diptera: Muscidae)", J. Econ. Entomol, 1997, 90:883-892.

Lota, M.L., et al., "Volatile components of peel and leaf oils of lemon and lime species", J. Agri. Food Chem., 2002, 50:796-805.

Marcus C. and Lichtenstien, P., "Biologically active components of anise: toxicity and interactions with insecticides in insects", J. Agri. Food Chem., 1979, 27(6):1217-1223.

Miresmailli, S., et al., "Comparative toxicity of *Rosmarinus officinalis* L. essential oil blends of its major constituents against Tetranychus urticae Koch 20 (Acari: Tetranychidae) on two different host plants", Pest Manag Sci, 2006, 62:366-371.

Mishra, A.K., et al., "Use of neem oil as a mosquito repellent in tribal villages of mandla district, madhya pradesh", Indian J Malariol, 1995, 32(3):99-103.

Momen, F.M., et al., "Influence of mint and peppermint on Tetrynychus urticae and some predacious mites of the Family Phytoseiidae (Acari: Tetranychidae: Phytoseiidae)", Acta Phytopathologica et Entomologica Hungaria, 2001, 36(1-2):143-153.

Naqvi, S.N.H., et al., "Comparative toxicity of RB-A [Neem Formulation] and Malathion against bed bugs", Proceedings of Pakistan Congress of Zoology, 1993, 13:369-377.

National Research Council, Board on Science and Technology for International Development, Ad Hoc Panel Report, Neem: A Tree for Solving Global Problems, Washington: National Academy Press, 1992.

Obeng-Ofori, D., et al., "Bioactivity of eugenol, a major component of essential oil of Ocimum suvae (wild) against four species of stored product coleopteran", Int. J. Pest Manag. 1997, 43:89-94.

Pavela, R., et al., "Effectiveness of Neem (*Azidirachta indica*) insecticides against Brassica pod midge (*Dasinera brassicae* Winn.)", Journal of Pest Science, 2009, 82(3):235-240.

Perrucci, S., et al., "Therapeutic efficacy of linalool for the topical treatment of parasitic otitis caused by Psoroptes cuniculi in the rabbit and in the goat", Med. Vet. Entomol, 1997, 11:300-302.

Product labels for Cirkil CX and Cirkil RTU products, first sold in the United States on or about Jun. 25, 2012.

Rahman, A and Talukder, F.A., "Bioefficacy of some plant derivatives that protect grain against the pulse beetle, *Callosobruchus maculatus*", Journal of Insect Science, 2006, 6:03.

Rajeswara, Rao, B.R., et al., "Volatile flower oils of three genotypes of rose-scented geranium (*Pelargonium* sp.)", Flavour Frag J. , 2000, 15:105-107.

Romero, A., et al., "Insecticide resistance in the bed bug: a factor in the pests sudden resurgence", J Med Entomol, 2007, 44(2):175-178.

Salom, S.M., et al., "Laboratory evaluation of biologically-based compounds as antifeedants for the pales weevil, hulobius-pale (Herbst)", J. Entomol, Sci., 1994, 29:407-419.

Samarasekera, R., "Mosquitocidal activity of leaf and bark essential oils of Ceylon Cinnamomum zeylanicum", Journal of Essential Oil Research, 2005, 17(3):301-303.

Santos, P.M., et al., "Essential oils from hairy root cultures and fruits and roots of Pimpinella anisum", Phytochemistry, 1998, 48:455-460.

Schmahl, G., et al., "The efficacy of neem seed extracts (Tre-San, MiteStop) on broad spectrum of pests and parasites", Parasitology Research, 2010, 107(2):261-269.

Schmutterer, H. "Properties and potential of natural pesticides from the neem tree, *Azadirachta indica*", Annu Rev Entomol, 1990, 35:271-297.

Shabnum, S. and Wagay, M., "Essential oil composition of *Thymus vulgaris* L. and their uses", Journal of Research Development, 2011, 25(11):83-94.

Shellie, R., et al., "Characterisation of lavender essentail oils by using gas chromatography-mass spectrometry with correlation of linear retention indices and comparison with comprehensive two-dimensional gas chromatography", J. Chromatogr. A., 2002, 970:225-234.

Simic, A., et al., "The chemical composition of some Lauraceae essential oils and their antifungal activities", Phytother. Res. 2004, 18:713-717.

Thompson, J., et al., "Qualitative and quantitative variation in monoterpene co-occurrence and composition in the essential oil of Thymus vulgaris chemotypes", J. Chem Ecol, 2003, 29:859.

Toncer, O., et al., "Changes in essential oil composition of oregano (*Origanum onites* L.) due to diurnal variations at different developmental stages", Notulae Botanicae Horti Agrobotanici Cluj, 2009, 37(2):177-181.

Traboulsi, A.F., et al., "Insecticidal properties of essential plant oils against the mosquito *Culex pipiens* molestus (Diptera: Culicidae)", Pest Manag Sci, 2002, 58(5):491-495.

Tripathi, A.K., et al., "Effects of volatile oil constituents of Mentha species against stored grain pests, *Callosobruchus maculatus* and *Tribolium castanum*", J. Med Arom Plant Sci, 2000, 22:549-556.

Tripathi, A.K., et al., "Toxicity, feeding deterrence, and effect of activity of 1, 8-cineole from Artemisia annua on progeny production of Tribolium castanaeum (Coleoptera: Tenebrionidae)", J. Econ. Entomol, 2001, 94:979-983.

Trongtokit Y., et al., "Comparative repellency of 38 essential oils against mosquito bites", Phytotherapy Res, 2005, 19:303-309.

Vasudeva, N. and Sharma, T., "Chemical composition and antimicrobial activity of essential oil of citrus limettioides Tanaka", Journal of Pharmaceutical Technology and Drug Research, 2012, 1(1):2.

Vokou, D., et al., "Geographic variation of Greek oregano (*Origanum vulgare* ssp. *Hirtum*) essential oils", Biochem Syst Ecol, 1993, 21:287-295.

Webb, et al, "On the penetration of insecticides through the insect cuticle" (Cooper Technical Bureau: Berkhamsted), Journal of Experimental Biology, 1945, 22:8-20.

Xia, Y., et al., "The molecular and cellular bassis of olfactory-driven behaviour in Anopheles gambiae larvae", Proceedings of the National Academy of Sciences of the USA, 2008, 105:6433-6438.

Yang, Y.C. et al., "Ovicidal and adulticidal effects of Eugenia caryophyllata bud and leaf oil compound on Pediculus capitis", J Agri Food Chem, 2003, 51:4884-4888.

Yang, Y.C., et al., Ovicidal and adulticidal activities of Cinnamomum zeylanicum bark essential oil compounds and related compounds against Pediculus humanus capitis (Anoplura: Pediculidae), Int J Parasitol, 2005, 35:1595-1600.

"Animal Health Farms Products—Checkmite". Accessed Dec. 10, 2016. <http://animal health.bayer.ca/en/farms/heckmite/>.

(56) References Cited

OTHER PUBLICATIONS

"Apiguard: Varroa control Vita Europe". Accessed Oct. 12, 2016. <http://www.vita-europe.com/products/apiguard/>.

"Apistan: Varroa control Vita Europe". Accessed Dec. 10, 2016. <http://www.vita-europe.com/products/apistan/>.

Apivar Varroa Mite Strips. Accessed Dec. 10, 2016. <http://apivar.co/nz>.

Guzman-Novoa, E, et al, "Varroa destructor is the main culprit for the death and reduced populations of overwintered honey bee (*Apis mellifera*) colonies in Ontario, Canada", Apidologie, 2010, 41(4): 443-450.

Melathopoulos, AP, et al, "Field evaluation of neem and canola oil for the selective control of the honey bee (Hymenoptera: Apidae) mite parasites *Varroa jacobsoni* (Acari: Varroidae) and *Acarapis woodi* (Acari: Tarsonemidae)", Journal of Economic Entomology, 2000, 93(3):559-567.

"Mite Away Quick Strips—NOD Apiary Products". Accessed Oct. 13, 2016. <http://nodglobal/com/mite-away-quick-strips/.

"Mite Gone for Effective Control of the Varroa & Tracheal Mites". Accessed Oct. 13, 2016. <http:/www.mitegone.com/>.

Thompson, HM, et al, "First report of varroa destructor resistance to pyrethroids in the UK", Apidologie, 2002, 33(4):357-366.

"Thymovar". Accessed Dec. 10, 2016. <http://biovet.ch/en/lmkerei/thymovar.html>.

Abbassy, M.A., et al., "Insecticidal and synergistic effects of Majorana hortensis essential oil and some of its major constituents", Entomologia Experimentalis et Applicata, 2009, 131(3):225-232.

Ahmed, K.S., et al., "Effects of plant oils on oviposition preference and larval survivorship of Callosobruchus chinesis on azuki bean", Applied Entomology and Zoology, 1999, 34(4):547-550.

Ansari, M.A., et al. "Larvicidal and mosquito repellent action of peppermint (*Mentha piperita*) oil", Bioresource Technology, 2000, 71(3):267-271.

Arslan, N., et al., "Variation in essential oil content and composition in Turkish anise (*Pimpinella anisum* L.) populations", Turk. J. Agri. For., 2004, 28:173-177.

Avato, P., et al., "Allysulfide constituents of garlic volatile oil as antimicrobial agents", Phytomedicine, 2000, 7(3):239-243.

Barnard, D.R., "Repellency of essential oils to mosquitoes (*Diptera culicidae*)", Journal of Medical Entomology, 1999, 36(5):625-629.

Brahmachari, G., "Neem—an omnipotent plant: a retrospection", Chembiochem, 2004, 5:408-421.

Chaieb, K., et al., "The chemical composition and biological activity of clove essential oil, Eugenia caryophyllata (*Syzigium aromaticum* L. Myrtaceae): a short review", Phytotherapy Research, 2007, 21(6):501-506.

Chang, K.S. and Ahn, Y.T., "Fumigant activity of {E)—anethole identified in Illicium verum fruit against Blatella germanica", Pest Manage. Sci., 2001, 58:161-166.

Chang, S.T. and Cheng, S.S., "Antitermitic activity of leaf essential oils and components from Cinnamomum osmophleum", J. Agric. Food Chem., 2002, 50:1389-1392.

Chastrette, M., et al., "Approach to general classification of solvents using a multivariate statistical treatment of quantitative solvent parameters", Journal of the American Chemical Society, 1985, 107(1):1520-1526.

Cheng, S.S., et al., "Variations in insecticidal activity and chemical compositions of leaf essential oils from Cryptomeria japonica at different ages", Bioresource Tech., 2009, 100(1):465-470.

Choi, W., et al., Toxicity of plant essential oils to Tetranychus urticae (Acari:Tetranychidae) and Phytoseiulus persimilis (Acari:Phytoseiidae), Journal of Economic Entomology, 2004, 97(2):553-558.

Clark, R.J. and Menary, R.C., "Variations in compositions of peppermint oil in relation to production areas", Econ. Bot., 1981, 35:59-69.

Daniel, S.H. and Smith, R.H., "The repellent effect of neem (*Azadirachta indica* A Juss) oil and its residual efficacy against Callosobruchus maculatus on cowpea", in Fleurat-Lessard, F, Ducom, P. eds (Proceedings Fifth International Working Conference on Stored-Product Protection) (Bordeaux, 1990), 1589-1597.

Don-Pedro, K.M., "Investigation of single and joint fumigant insecticidal action of citrus peel oil components", Pestic. Sci., 1996, 46:79-84.

Ellis, M.D., and Baxendale, F.P., "Toxicity of seven monoterpenoids to tracheal mites (Acari: Tarsonemidae) and their honey bee (Hymenoptera: Apidae) hosts when applied as fumigants", J. Econ. Entomol, 1997, 90:1087-1091.

Erbilgin, et al., "Acetophenone as an anti-attractant for the Western Pine Beetle, *Dendroctonus brevicomis* Leconte", J Chem Ecol, 2007, 33:817-823.

Franzios, G., et al., "Insecticidal and genotoxic activities of mint essential oils", J. Agric. Food Chem., 1997, 45:2690-2694.

Fuhremann, T.W., et al.,. "Effects of naturally occurring food plant components on insecticide degradation in rats", J. Agri. Food Chem., 1978, 26(5):1068-1075.

* cited by examiner

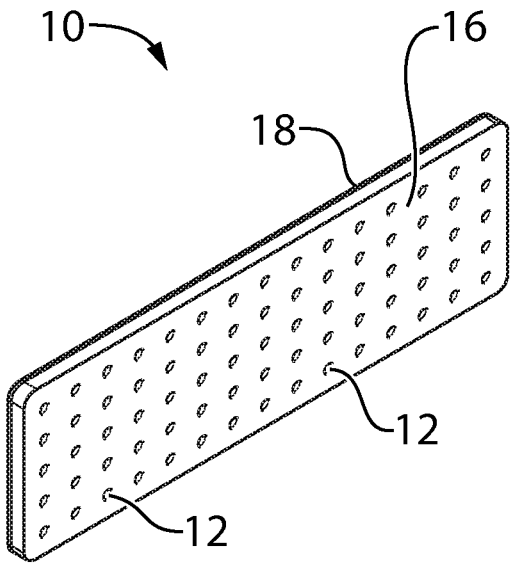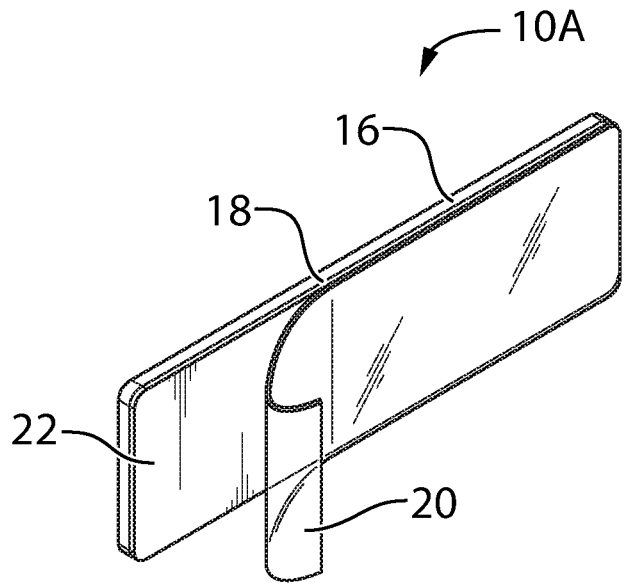
FIG.1  FIG.2
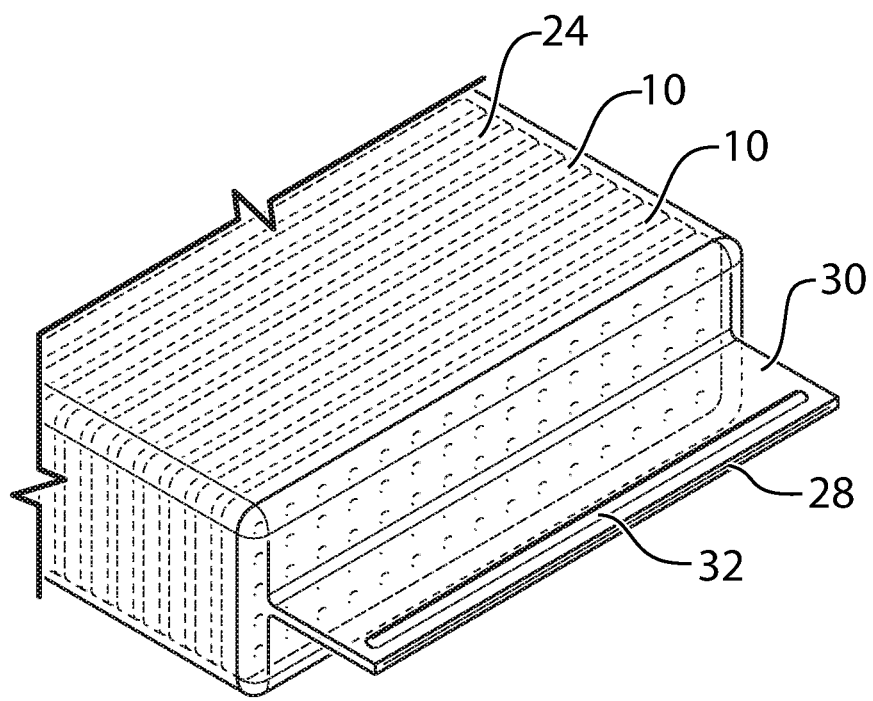
FIG.3

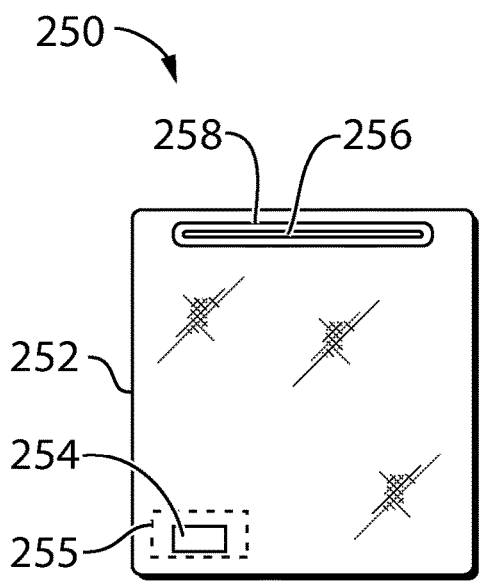
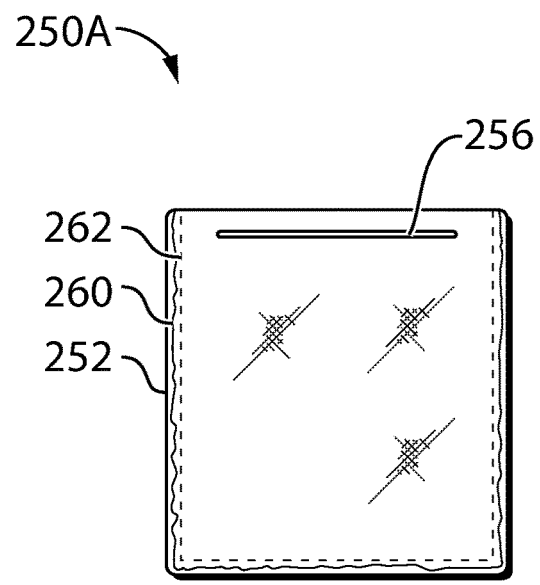
FIG.14a  FIG. 14b
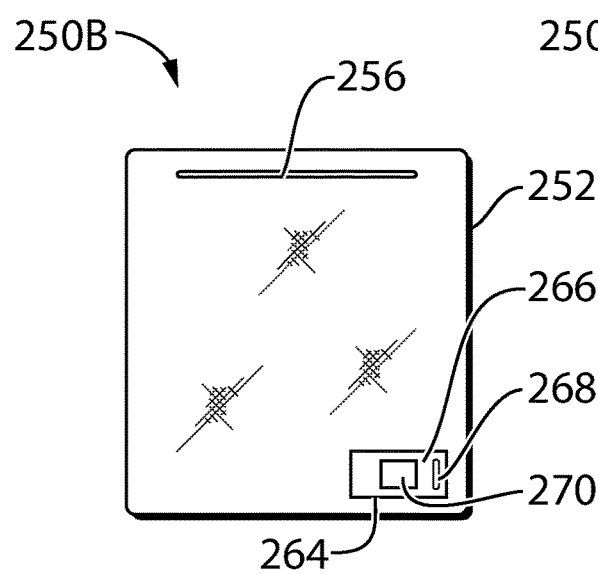
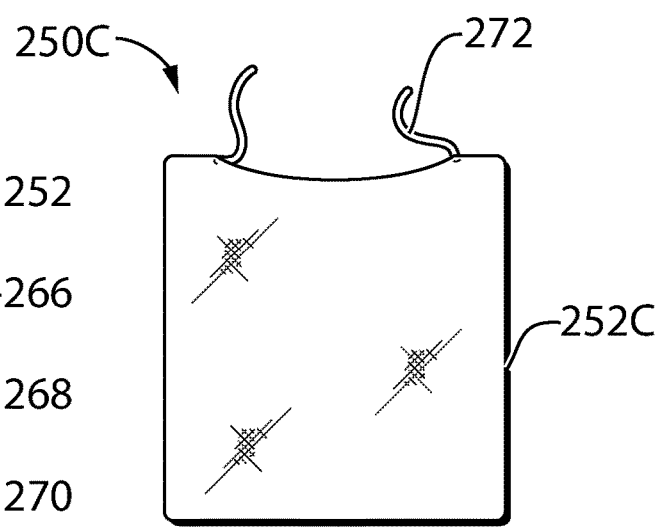
FIG.14c  FIG.14d

COMPOSITIONS, DEVICES AND METHODS FOR CONTROL OF PESTS USING VAPOR ACTIVITY

REFERENCE TO RELATED APPLICATIONS

This application is a 371 of Patent Cooperation Treaty patent application No. PCT/IB2014/066139 filed 18 Nov. 2014, which claims priority to, and the benefit of, U.S. provisional patent application Nos. 61/905,415; 61/911,434; 61/913,194; 61/918,641; 61/941,049; and 62/008,425. Each of these applications is incorporated by reference herein.

TECHNICAL FIELD

Some embodiments of the present invention pertain to compositions, substrates and/or devices that can be used to control a variety of pests. Some embodiments of the present invention can be used to control arthropods, including for example, bed bugs, varroa mites, granary weevils, and/or other pests. Some embodiments of the present invention are compositions, substrates or devices that release vapors having pesticidal activity. Some embodiments of the present invention pertain to compositions, methods or apparatus for selectively controlling an undesirable pest, including an arthropod, while not harming or harming to a lesser extent than the undesirable pest a desirable organism, including an arthropod. In some embodiments, the compositions, methods or apparatus are used to control household pests, to control parasitic infestations, and/or to treat foodstuffs and the like.

BACKGROUND

Pest control is an ongoing, worldwide problem. Lack of effective pesticides has resulted in nearly epidemic growth of some pests. There is consistently increasing demand for safe, naturally-derived, effective pest control solutions to address these issues.

There are several problems with existing products. Conventional chemical pesticides are toxic or do not work well enough. Many insects have developed high levels of resistance to common conventional pesticides. Many conventional pesticides are being limited or phased out by governments. This has prompted a search for natural solutions, but traditional botanical biochemicals can be inconsistent, unstable, hard to deliver and only work on contact.

One particular challenge in controlling pests such as bed bugs and other arthropods is that the pests may harbor in areas that are difficult to treat or susceptible to damage by conventional liquid spray products and methods. For example, bed bugs are known to hide in any available cracks and crevices, including within books, electronics, frames, seams, etc., that cannot be effectively or safely treated by conventional sprays or dusts. These conventional pesticide products typically require direct contact between the pest and the pesticide in its solid or liquid form in order to be effective.

Examples of pests include all life-stages of insects of the orders Hemiptera, Blattodea, Hymenoptera, Siphonaptera, Coleoptera, Lepidoptera, Diptera, Thysanura, Psocoptera, Dermaptera, Orthoptera Thysanoptera, including pests that impact human health such as bed bugs (*Cimex lectularius*), kissing bugs (*Triatoma* spp., *Paratriatoma* spp.), cockroaches (*Blattella* spp., *Periplaneta* spp., *Blatta* spp., *Supella* spp.), ants (family Formicidae), and fleas (*Ctenocephalides* spp. *Pulex* spp., *Xenopsylla* spp.), as well as insect pests that invade human structures such as beetles (*Sitophilus* spp., *Dermestes* spp., *Attagenus* spp., *Anthrenus* spp., *Trogoderma* spp., *Tenebrio* spp.), moths (*Tinea pellinella, Tineola bisselilella, Plodia* spp.), flies (*Drosophila* spp., *Calliphora* spp., *Phaenicia* spp., *Pollenia* spp., *Musca* spp., *Sarcophaga* spp., *Wohlfahrtia vigil, Psychoda* spp., *Telmatoscopus albipunctatus, Dohrniphora cornuta, Megaselia scalaris,* family Sciaridae, family Mycetophilidae), stink bugs (*Boisea trivattata*), silverfish (*Lepisma saccharina, Ctenolepisma longicaudata*), firebrats (*Thermobia domestica*), booklice (*Lachesilla pedicularia, Liposcscelis* spp.), earwigs (*Forficula auricularia, Emorellia annulipes, Labidura riparia*), crickets (*Acheta donesticus, Gryllus* spp.), and the like. Examples of non-insect arthropod pests include all life stages of human body lice (*Pediculus humanus, Pediculus humanus capitis, Pthirus pubis*), ticks (Family Ixodidae), chiggers (Family Tromiculidae), human & vertebrate mites (*Sarcoptes scabies, Ornithonyssus* spp., *Dermanyssus gallinae, Pyemotes tritici*, invertebrate mites (*Varroa destructor*), and the like. Pests also include pests that can infest stored products (including for example foodstuffs), including almond moth (*Cadra cautella*), Angoumois grain moth (*Sitotroga cerealella*), carpet beetle (*Dermestes maculatus*), Cadelle (*Tenebroides mauritanicus*), cigarette beetle (*Lasioderma serricorne*), coffee bean weevil (*Araecerus fasciculatus*), confused flour beetle (*Tribolium confusum*), cowpea weevil (*Callosobruchus maculatus*), drugstore beetle (*Stegobium paniceum*), European grain moth (*Nemopogon granella*), flat grain beetle (*Cryptolestes pusillus*), grain mite (*Acarus siro*), granary weevil (*Sitophilus granarius*), Indian meal moth (*Plodia interpunctella*), Khapra beetle (*Trogoderma granarium*), larder beetle (*Dermestes lardarius*), lesser grain borer (*Rhyzopertha dominica*), maize weevil (*Sitophilus zeamais*), mealworm (*Tenebrio molitor*), Mediterranean flour moth (*Anagasta kuehniella*), merchant grain beetle (*Oryzaephilus mercator*), red flour beetle (*Tribolium castaneum*), rice moth (*Corcyra cephalonica*), rice weevil (*Sitophilus oryzae*), rusty grain beetle (*Cryptolestes ferrugineus*), sawtooth grain beetle (*Oryzaephilus surinamensis*), warehouse beetle (*Trogoderma variable*), and the like.

Another problem in controlling pests is that, while there are pests that are arthropods, there are also a number of beneficial species that are also arthropods. It may be desirable to control pest species of arthropods, while not harming, or at least harming to a lesser extent, a beneficial species of arthropod. One example of such a problem needing to be addressed is varroa mite infestations of honey bee colonies. *Varroa* mites are an external parasitic mite that attach to and feed on honey bees and are believed to be the largest contributing factor in the present decline of honey bee populations. A significant mite infestation may be a contributing factor to colony collapse disorder (CCD) and can lead to the death of a honey bee colony. This has a major economic impact on the beekeeping industry as well as a serious environmental impact due to the beneficial role bees play in the ecosystem. *Varroa* mites are smaller in size (i.e. have a lower mass) than honey bees. There is a need for compositions, methods and apparatus that can be used to control *varroa* mites without significantly harming honey bees.

*Varroa* mites are arthropods that are members of the Class Arachnida, Subclass Acari, Family Varroidae, Genus *Varroa*, Species *destructor*. Honey bees are also arthropods that are members of the Class Insecta, Order Hymenoptera, Family Apidae, Genus *Apis*, Species *mellifera*. *Varroa* mites are smaller in size (i.e. have a lower mass) than honey bees.

There is a need for compositions, methods and apparatus that can be used to control *varroa* mites without significantly harming honey bees. There are existing treatments for treating *varroa* mites in honey bee colonies (Apistan™ strips (Tau-fluvalinate) and Mite-Away Quick Strips™ (formic acid)). However, formic acid vapour is very corrosive, and special handling precautions must be used when formic-acid based treatments used. Apistan™ strips have relatively high contact toxicity for humans, and therefore require the use of gloves and protective clothing when being handled. Furthermore, residues from Apistan™ strips can accumulate in wax, and some *Varroa* mite populations have developed resistance to its active ingredient.

Existing products that use vapors to treat pests typically have high toxicity. Vapona™ or Nuvan™ strips (dichlorvos or DDVP) are too toxic to use in bee hives, and when used to treat bed bugs and other pests, exposure to vapour or liquid risk acute and chronic toxicity to humans.

There is a need for improved pest control products and methods that utilize vapor action to effectively and safely treat pests in a manner that addresses the drawbacks of existing treatments. Vapors have the advantage of dispersing evenly throughout a given volume of space, including penetrating into small and hidden spaces that would be difficult or impossible to reach otherwise. Vapors allow the maximum and most even penetration within a volume of space of a given mass of a pesticide. Gas phase vapors also have the advantage of not adversely affecting many types of materials such as electronics, books, or other valuable items, that can be damaged by application of a liquid (e.g. short-circuiting, warping, staining, etc.), or adversely affecting such materials to a lesser extent than a liquid.

One disadvantage of some pesticidal compounds, including botanical oils such as neem oil for example, is that they have low volatility and do not release effective quantities of pesticidal vapors. There remains a need for compositions and methods that improve the volatilization of pesticidal compounds and/or otherwise allow for the release of vapors having effective pesticidal activity.

Potential references of interest include the following, each of which is incorporated by reference herein:

WO 2013/050967.

Thompson H M, Brown M A, Ball R F, Bew M H (2002). First report of *Varroa destructor* resistance to pyrethroids in the UK". Apidologie 33 (4): 357-366. doi:10.1051/apido:2002027.

Guzmán-Novoa E, Eccles L, Calvete Y, Mcgowan J, Kelly P G & Correa-Benítez A (2009) *Varroa destructor* is the main culprit for the death and reduced populations of overwintered honey bee (*Apis mellifera*) colonies in Ontario, Canada. Apidologie 41 (4): 443-450. doi:10.1051/apido/2009076.

Melathopoulos A P, Winston M L, Whittington W R, Higo H, Le Doux M (2000). Field evalustion of neem and canola oil for the selective control of the honey bee (Hymenoptera: Apidae) mite parsites *Varroa jacobsoni* (Acari: Varroidae) and *Acarapis woodi* (Acari: Tarsonemidae). Journal of Economic Entomology 93: 559-567.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Devices and methods are provided for controlling pests using pesticidal vapors. The pests can be terrestrial arthropods, including subterranean arthropods. In some embodiments, an arthropod pest is controlled while a beneficial species, which can also be an arthropod, is not harmed, or is harmed to a lesser extent, by the pesticidal vapors. In some such embodiments, the pest is *varroa* mites and the beneficial species is honey bees.

In some embodiments, pesticidal vapors are released from a substrate impregnated with a pesticidal composition, from a gel comprising a pesticidal composition, and/or from a device for releasing pesticidal vapors, including from a liquid pesticidal composition.

In some embodiments, the device has a housing with a reservoir for containing a pesticidal composition, and a mechanism for releasing vapors of the pesticidal composition. In some embodiments, the device is or has a substrate impregnated with a pesticidal composition. The substrate can be a naturally occurring polymer or a synthetic polymer. In some embodiments, the substrate is cotton, paper, or a porous plastic made from polyethylene or polyester fibres. In some embodiments, the release of vapors by the device is enhanced by an active release mechanism. In some embodiments, an indicator is provided to provide a visual indication of the amount of pesticidal composition remaining in the device.

In some embodiments, a source of pesticidal vapors is placed in a treatment enclosure containing pests or articles infested or thought to be infested with pests. In some embodiments, the source of pesticidal vapors is integrated with or provided as an integral component of the treatment enclosure. In some embodiments, the source of pesticidal vapors is enclosed within the treatment enclosure for a period of time sufficient to control pests within the treatment enclosure. In some embodiments, the supply of pesticidal composition to the substrate is periodically or continuously replenished to continue production of pesticidal vapors over a period of time, for example by pumping additional pesticidal composition to the substrate. In some embodiments, the pesticidal composition is supplied to a device for releasing pesticidal vapors as a self-contained puck, and the puck is periodically exchanged for a fresh puck.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 1 shows an impregnated substrate with an impermeable backing in accordance with one example embodiment of the invention.

FIG. 2 shows an impregnated substrate with an adhesive backing in accordance with an example embodiment of the invention.

FIG. 3 shows a package of impermeable substrates with a resealable closure in accordance with an example embodiment of the invention.

FIG. 12a shows the impregnated substrate in a sealed package that is opened by a user to release pesticidal vapors, although the substrate and package are separately illustrated for clarity.

FIG. 14a shows schematically a bag with integrated pesticide-impregnated substrate according to one example embodiment. FIG. 14b shows schematically an example embodiment of a multi-layer bag with a pesticidal composition impregnated substrate membrane. FIG. 14c shows an example embodiment of a reusable treatment enclosure with an external enclosure for receiving a source of pesticidal vapors. FIG. 14d shows an example embodiment of a single layer bag with a pesticidal composition impregnated therein.

DESCRIPTION

Figure 4A:
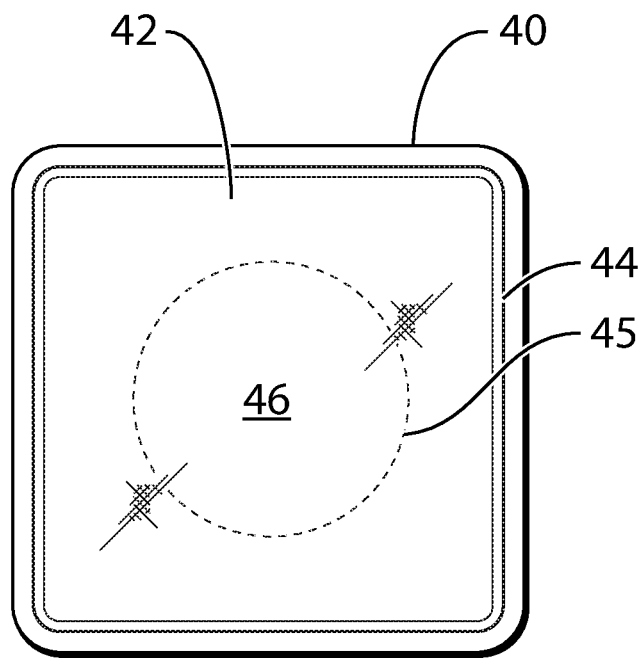
FIG. 4abc show passive versions of devices with a permeable membrane (FIG. 4a), a non-adjustable venting method (FIG. 4b) and an adjustable venting method (FIG. 4c) in accordance with some example embodiments of the invention.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless defined otherwise, all technical and scientific terms used herein have the same meaning as commonly understood by one of ordinary skill in the art to which this invention belongs.

As used herein, singular forms include plural references unless the context clearly dictates otherwise. As used herein, "comprises" or "comprising" are to be interpreted in their open-ended sense, i.e. as specifying that the stated features, elements, steps or components referred to are present, but not excluding the presence or addition of further features, elements, steps or components.

As used herein, the term "pest" refers to organisms that negatively affect a host or other organism—such as a plant or an animal such as a mammal—by colonizing, damaging, attacking, competing with them for nutrients, or infecting them, as well as undesired organisms that infest human structures, dwellings, living spaces or foodstuffs. Pests can include arthropods, including insects, arachnids and cockroaches, and includes sucking, biting and stinging pests such as bed bugs, kissing bugs, mites, ticks, ants, lice, fleas, chiggers, biting flies, mosquitoes, and wasps, as well as insects that infest stored products such as moths, mites and weevils.

Exemplary pests against which some embodiments can be used include terrestrial arthropods (including subterranean arthropods), including all life-stages of insects of the orders Hemiptera, Blattodea, Hymenoptera, Siphonaptera, Coleoptera, Lepidoptera, Diptera, Thysanura, Psocoptera, Dermaptera, Orthoptera Thysanoptera, including pests that impact human health such as bed bugs (*Cimex lectularius*), kissing bugs (*Triatoma* spp., *Paratriatoma* spp.), cockroaches (*Blattella* spp., *Periplaneta* spp., *Blatta* spp., *Supella* spp.), ants (family Formicidae), and fleas (*Ctenocephalides* spp. *Pulex* spp., *Xenopsylla* spp.), as well as insect pests that invade human structures such as beetles (*Sitophilus* spp., *Dermestes* spp., *Attagenus* spp., *Anthrenus* spp., *Trogoderma* spp., *Tenebrio* spp.), moths (*Tinea pellinella, Tineola bissellilella, Plodia* spp.), flies (*Drosophila* spp., *Calliphora* spp., *Phaenicia* spp., *Pollenia* spp., *Musca* spp., *Sarcophaga* spp., *Wohlfahrtia vigil, Psychoda* spp., *Telmatoscopus albipunctatus, Dohrniphora cornuta, Megaselia scalaris,* family Sciaridae, family Mycetophilidae), stink bugs (*Boisea trivattata*), silverfish (*Lepisma saccharina, Ctenolepisma longicaudata*), firebrats (*Thermobia domestica*), booklice (*Lachesilla pedicularia, Liposcscelis* spp.), earwigs (*Forficula auricularia, Emorellia annulipes, Labidura riparia*), crickets (*Acheta donesticus, Gryllus* spp.), and the like. Examples of non-insect arthropod pests include all life stages of human body lice (*Pediculus humanus, Pediculus humanus capitus, Pthirus pubis*), ticks (Family Ixodidae), chiggers (Family Tromiculidae), human & vertebrate mites (*Sarcoptes scabies, Ornithonyssus* spp., *Dermanyssus gallinae, Pyemotes tritici,* invertebrate mites (*Varroa destructor*), and the like. Pests also include pests that can infest stored products, including almond moth (*Cadra cautella*), Angoumois grain moth (*Sitotroga cerealella*), carpet beetle (*Dermestes maculatus*), Cadelle (*Tenebroides mauritanicus*), cigarette beetle (*Lasioderma serricorne*), coffee bean weevil (*Araecerus fasciculatus*), confused flour beetle (*Tribolium confusum*), cowpea weevil (*Callosobruchus maculatus*), drugstore beetle (*Stegobium paniceum*), European grain moth (*Nemopogon granella*), flat grain beetle (*Cryptolestes pusillus*), grain mite (*Acarus siro*), granary weevil (*Sitophilus granarius*), Indian meal moth (*Plodia interpunctella*), Khapra beetle (*Trogoderma granarium*), larder beetle (*Dermestes lardarius*), lesser grain borer (*Rhyzopertha dominica*), maize weevil (*Sitophilus zeamais*), mealworm (*Tenebrio molitor*), Mediterranean flour moth (*Anagasta kuehniella*), merchant grain beetle (*Oryzaephilus mercator*), red flour beetle (*Tribolium castaneum*), rice moth (*Corcyra cephalonica*), rice weevil (*Sitophilus oryzae*), rusty grain beetle (*Cryptolestes ferrugineus*), sawtooth grain beetle (*Oryzaephilus surinamensis*), warehouse beetle (*Trogoderma variable*), and the like.

As used herein, the term "vapor" has the meaning as defined by the Merriam Webster dictionary, of a "substance that is in the form of a gas or that consists of very small drops or particles mixed with the air." Examples of vapors include, without limitation, gases, aerosols, mist, smoke, steam, fog, fumes and fumigants.

As used herein, the term "substrate" refers to any substance that contains or is impregnated with a pesticidal composition. The substrate provides a medium for absorbing a liquid pesticidal composition and releasing vapors of the pesticidal composition.

As used herein, the term "gel" refers to a solid or semi-solid material having a substantially dilute cross-linked system, which exhibits no flow when in the steady-state.

As used herein, the term "liquid" refers to a substance that has a definite volume but no fixed shape. The "viscosity" of a liquid refers to the resistance of a liquid to gradual deformation by shear stress or tensile stress. A liquid with a higher viscosity is a relatively thicker (slower flowing) liquid.

As used herein, the term "diffuse" or "diffusion" refers to the spreading out of a substance through a volume of space, generally from regions of high concentration to regions of lower concentration. "Passive diffusion" refers to naturally occurring diffusion of a gas or aerosol unaided or influenced by application of an outside force, whereas "active diffusion" refers to diffusion that is aided or facilitated or influenced by the application of an outside force, agent or device.

As used herein, the term "phoretic mites" means mites living on adult bees, outside of the brood cells where the bees matured.

As used herein, the terms "control" or "controlling" include, but are not limited to, any killing, growth regulating, knockdown or peststatic (inhibiting or otherwise interfering with the normal life cycle of the pest) activities of a composition against a given pest. These terms include for example sterilizing activities which prevent the production of ova or sperm, cause death of sperm or ova, or otherwise cause severe injury to the genetic material. Further activities intended to be encompassed within the scope of the terms "control" or "controlling" include preventing larvae from developing into mature progeny, modulating the emergence of pests from eggs including preventing eclosion, degrading the egg material, suffocation, reducing gut motility, inhibiting the formation of chitin, disrupting mating or sexual communication, and preventing feeding (antifeedant) activity. "Knockdown" is the inability of an arthropod to make coordinated movement, which eliminates its ability to locate food, shelter and/or host organisms.

Some embodiments of the present invention provide pesticidal compositions that release vapors (via evaporation, aerosolization, etc.) having effective pesticidal activity against pests and their eggs. Some embodiments provide substrates impregnated with a pesticidal composition such that the substrate releases pesticidal vapors over time. Some embodiments provide devices comprising a liquid or gelled pesticidal composition or a substrate impregnated with a pesticidal composition, wherein the device actively or passively diffuses pesticidal vapors.

In some embodiments, the pesticidal composition is applied in liquid form to a substrate such that the substrate contains, absorbs or is impregnated with the pesticidal composition and serves as a vehicle for release of the pesticidal composition in vapor form. Examples of such substrates include any kind of cloth, paper, textile, wipe, pad, sponge, or other porous or absorbent material.

In some example embodiments, the substrate is a naturally occurring polymer, such as cellulose (for example in the form of cotton, paper, wood, wood pulp, or the like), wool, felt, chitin, silk or the like. Natural plant fibers can also be 'manufactured' into an artificial material where they are processed into pulp and then extruded like synthetic fibers like polyester or nylon to produce an artificial fiber like rayon or viscose, and these materials can be used as substrates in some example embodiments.

In some embodiments, the substrate is non-woven, for example, cotton batting and filter paper are examples of non-woven cellulose substrates. In some embodiments, the substrate is woven, for example, cotton cloth, wool or silk are examples of a woven cellulose substrates.

As used herein, a "woven" substrate refers to a substrate formed by weaving or knitting fibers together. The fibers can be synthetic (e.g. polyester or polypropylene) or natural (e.g. plant-derived like pulp or cotton or animal derived like wool or silk).

As used herein, a "non-woven" substrate is a substrate that is not woven. In some cases, naturally-occurring non-woven substrates will be produced naturally or with some human processing, for example in the case of cotton and paper. In some cases, fabric-like materials can be made through processing techniques that do not result in the formation of a woven substrate, and hence are non-woven, for example, some fabric-like materials are made from long fibers bonded together by chemical, mechanical, heat or solvent treatments, for example felt.

In some example embodiments, the substrate is a synthetic polymer, such as polyester, copolyester, cellulose acetate, olefins, nylon, modacrylate, polyphenylene sulfide, rayon, nylon, polypropylene, polyethylene, polybutylene terephthalate, polyurethanes, acrylic polymers, latex, styrene/butadiene, a silicone, or the like. In some embodiments, the synthetic polymer is woven. In some embodiments, the synthetic polymer is non-woven.

In some example embodiments, the substrate is a non-woven synthetic material, such as polyester, copolyester, cellulose acetate, olefins, nylon, modacrylate, polyphenylene sulfide, viscose, rayon, or the like. In some example embodiments, the substrate is a woven synthetic polymer, for example, polyester, nylon, polypropylene, polyethylene, or the like.

In some embodiments, the synthetic material can be partly or fully biodegradable.

In some embodiments, the substrate is a sponge. In some embodiments, the sponge is made from a synthetic material, for example, a foamed plastic polymer, a low density polyether, polyvinyl acetate (PVA), silicone or polyurethane foam, polyester, or the like. In some embodiments, the sponge is manufactured from a naturally occurring material such as cellulose, including cellulose obtained from wood.

In some embodiments, the substrate is a natural or manufactured cellulose material. In some embodiments, the natural cellulose material is in granular form, for example, corncob, wood, wood pulp, nut shells, chips, bark or the like.

In some embodiments, the substrate is a mineral, such as zeolite, diatomaceous earth, clay, sepiolite, bentonite clay, silica, silicate, silicon dioxide, or the like. In some embodiments, the mineral is provided in granular form.

In some embodiments, the substrate is a carrier such as a wax, such as an animal wax (e.g. beeswax), a plant wax (e.g. carnuba wax), or a petroleum-based wax (e.g. paraffin wax).

In some embodiments, the substrate is porous. In some embodiments, the pores have an average diameter of from about 5 to about 500 micrometers, or any amount or range there between, for example from about 10 to about 200, or from about 50 to about 150 micrometers, including any value therebetween, e.g. 25, 50, 100, 150, 200, 250, 300, 350, 400 or 450 micrometers.

In some embodiments, the substrate is a porous plastic. In some embodiments, the porous plastic comprises polyethylene, polyethylene terephthalate or polyester fibres. The fibres may be felted or glued, or fused to provide an open cell or porous structure that is non-woven.

The substrate should be selected to be compatible with the pesticidal solution to be released, and should be mechanically strong to retain a porous structure and be resistant to solvent degradation. Without being bound by theory, it is believed that any material that provides appropriate gaps between the fibers for receiving a pesticidal composition can be used in some embodiments of the present invention, regardless of whether the material is woven or non-woven. The gaps are believed to provide a space for receiving (i.e. absorbing) the liquid pesticidal composition, and the fibers are believed to assist with transporting the liquid pesticidal composition throughout the substrate to facilitate release of pesticidal vapors.

In some embodiments, the pesticide-impregnated substrate is replaced with a gelled pesticidal composition, i.e. a pesticidal composition which has been provided with a solid or semi-solid gel consistency by the addition of appropriate gelling agents.

In some embodiments, the pesticidal composition is formulated into a solid or gel that serves as a vehicle for releasing pesticidal vapors. For example, alginate, agar or any other gelling or thickening agent may be used to gel an aqueous solution containing a pesticidal composition, including for example suitable polymers. The gel may comprise natural gelling agents, or synthetic gelling agents, or a combination thereof. Examples of natural gelling agents include starches, agars, gums, pectin, proteins, collagen, gelatin, furcellaran, saccharides, hydrocolloids, and the like. Examples of synthetic gelling agents include silicones, polyethylene glycol (PEG), polyvinyl alcohol, or the like.

Addition of a gelling agent to an aqueous solution forms a weakly cohesive internal structure, to form a homogeneous gel (which may be solid or semi-solid, or creamy or pasty in some embodiments) from a solution of a pesticidal composition. Pesticidal vapors are then released from the gel.

In some embodiments, the pesticidal composition is absorbed or impregnated into a porous solid substrate or provided as a gel. In some embodiments, the solid substrate or gel compositions assist with controlling the rate of release of pesticidal vapors. While the embodiments described below are described with reference to the use of a substrate impregnated with a pesticidal composition or a liquid pesticidal composition contained in some suitable manner, in some embodiments, the substrate or the liquid composition are replaced with a pesticidal composition in gel form.

In some embodiments, the substrate is adapted to provide a visual indication of the relative amount of pesticidal composition remaining within the substrate. In some embodiments, the substrate changes dimensions (for example, by swelling or enlarging), when the pesticidal composition is applied to the substrate. In some embodiments, the substrate changes dimensions (for example, by shrinking), as the pesticidal composition is released as a vapor from the substrate (for example, by evaporation). Thus, a visual inspection of the relative dimensions of the substrate can provide a visual indication of the relative amount of pesticidal composition remaining within the substrate.

In some embodiments, the substrate includes an indicator, dye, or co-evaporating colored substance, so that the color of the substrate changes and provides a visual indication of the absorption and release of pesticidal composition from the substrate.

In some embodiments in which the carrier solvent for the pesticidal composition comprises an alcohol, an oxidative-reductive approach can be used as an indicator to provide a visual indication of the absorption and release of pesticidal composition from the substrate. For example, chromic acid derivatives can be used for oxidizing primary and secondary alcohols, such as Jones reagent (a solution of sodium dichromate in aqueous sulfuric acid) and pyridinium chlorochromate, $C_5H_5NH^{(+)}CrO_3Cl^{(-)}$, commonly known as PCC. Both reagents involve the use of chromium in which it is reduced from $Cr^{+6}$ to $Cr^{+3}$ in the presence of the alcohol and acid. $Cr^{+6}$ is yellowish orange in color and when it is reduced to $Cr^{+3}$, the color is changed to blue-green.

In some embodiments, a chromic acid derivative and a suitable acid such as sulphuric acid or hydrochloric acid are preloaded on an indicator paper associated with the substrate impregnated with a pesticidal composition comprising an alcohol as a carrier solvent, and the alcohol vapor released from the substrate as pesticidal vapors are released should react with the preloaded chromic acid derivative indicator paper to cause the paper to change color from yellow to green. The color change from yellow to green can be used as a visual indicator of the relative amount of pesticidal composition remaining in the substrate (i.e. when the color has changed from yellow to green, this indicates that most or all of the pesticidal composition has been released from the substrate). In alternative embodiments, rather than using a separate indicator paper, the indicator is integrated with the substrate.

In some embodiments, an indicator covered by a soluble coating that dissolves in the presence of pesticidal vapors is used to provide a visual indication of the amount of pesticidal composition remaining. As pesticidal vapor is released from a release device, the soluble coating is exposed to and dissolved by the pesticidal vapors. Once the coating has dissolved, the indicator is rendered visible. The thickness and/or composition of the coating can be adjusted so that the coating is dissolved after a majority of the pesticidal composition in the release device has been released as a vapor. Thus, the visibility of the indicator provides a visual indication that most or all of the pesticidal composition has been released from the substrate.

In some embodiments, the release of pesticidal vapors from a substrate proceeds by passive means, such as diffusion, evaporation, vaporization, aerosolization, or other natural process.

In some embodiments, the release of pesticidal vapors from a substrate proceeds by active means, i.e. the natural release of pesticidal vapors from the substrate is enhanced by another mechanism, for example, heating, air exchange (for example by the operation of a fan), sonication, addition of a chemical compound or enzyme that stimulates release of pesticidal vapors from the substrate or produces an exothermic reaction, addition of a gas such as $CO_2$, application of electrical current, or the like.

In some embodiments, an effective concentration of pesticidal vapors are used to control a pest. In some embodiments, pesticidal vapors are contained within a treatment enclosure to enhance the efficacy of treatment of a particular pest infested article (e.g. as compared with allowing the free diffusion of pesticidal vapors into the external environment). In some embodiments, the treatment enclosure is sealable, such that pesticidal vapors are released and contained within a confined space. In some embodiments, the treatment enclosure is permeable to pesticidal vapors, so that pesticidal vapors can diffuse out of the treatment enclosure. In some such embodiments, the permeable treatment enclosure slows the rate of diffusion of pesticidal vapors out of the treatment enclosure, as compared with the rate of diffusion of pesticidal vapors in open air. In some such embodiments, the permeable treatment enclosure helps to retain a sufficiently high vapor concentration within the treatment enclosure for a sufficiently long period of time to control any pests within the treatment enclosure.

In some embodiments, the pesticidal vapors are released from a liquid solution containing a pesticidal composition that is appropriately contained, for example by being contained within a membrane that is permeable to pesticidal vapors but not to liquid, or by being contained within a reservoir of a device for releasing pesticidal vapors, for example as described with reference to example embodiments of such devices below. In some embodiments, a viscosity-modifying agent is added to the liquid, to modulate the rate of release of pesticidal vapors from the liquid and/or to modulate the rate of flow of the liquid by modifying its viscosity. In some embodiments, petroleum jelly, liquid silicones, polyethylene glycol (PEG), polyvinyl alcohol, sulfonates, sodium or calcium salts, or the like are used as viscosity-modifying agents to modulate the viscosity of a liquid source of pesticidal vapors. In some embodiments, modulating the viscosity of a liquid source of pesticidal vapors can adjust the rate of release of pesticidal vapors from the liquid composition.

FIG. 1 illustrates an example embodiment of a pesticidal device 10 for releasing pesticidal vapors. Pesticidal device 10 has an absorbent substrate 16 that has been impregnated with a pesticidal composition or material that produces a pesticidal vapor. Pesticidal device 10 has an impermeable membrane 18 provided on one edge of the impregnated substrate 16. In embodiments where it is provided, impermeable membrane 18 may act as a backing to help prevent the pesticidal composition contained within impregnated substrate 16 from contacting surfaces on which pesticidal device 10 is placed.

In the illustrated embodiment of FIG. 1, impregnated substrate 16 has a plurality of dimples 12. Dimples 12 create a waffled surface. In some embodiments, dimples 12 may serve as wells to retain an applied (or pre-dosed) pesticidal composition to aid in absorption of that pesticidal composition into impregnated substrate 16. For example, dimples 12 may serve to prevent an applied liquid pesticidal composition from running off substrate 16 while the pesticidal composition is absorbed into substrate 16. In some embodiments, dimples 12 may be formed as a result of the process of manufacturing substrate 16 and/or device 10, and may be a pressure point binding multiple layers of substrate 16. In some embodiments, dimples 12 may be formed as a result of using a peg, optionally of the same material as substrate 16, to bind multiple layers of substrate 16 together.

In some example embodiments, an absorbent multi-layered substrate 16 comprises fibrous material that has been 'felted' together with pressure and/or friction in specific locations to produce dimples 12. In some embodiments, spot applications of adhesive are applied, penetrating multiple of layers to anchor them together, while leaving the majority of the surface and layers available for absorption of the applied pesticidal composition. In some example embodiments, mechanical aids such as dowels could be inserted through multiple layers of substrate 16, to help bind the separate layers together. In other embodiments, multiple layers of substrate 16 can be held together in any suitable manner.

In some embodiments, a base of the impregnated substrate is covered by an impermeable membrane 18 to prevent the release of moisture or vapors through that side so as to protect the surface on which the substrate is placed. With reference to FIG. 2, illustrating an alternative device 10A, in some embodiments, the base 18 of the substrate comprises an adhesive strip 22 for securing the substrate, for example within a treatment enclosure. In some embodiments, a side of the substrate comprises a removable cover strip 20 covering adhesive strip 22, to protect adhesive strip 22 and help it retain its adhesive properties until device 10 is deployed and the removable cover strip 20 removed by a user. In some embodiments, both an impermeable membrane 18 and an adhesive strip 22 are provided with the impermeable membrane 18 interposing adhesive strip 22 and impregnated substrate 16.

In some embodiments, a side of the substrate comprises a removable adhesive cover strip that is impermeable to prevent the release of moisture or vapors from the substrate until after the removable adhesive coverstrip is removed (e.g. after a user has removed the removable adhesive strip to activate the device). In some embodiments, the side of the substrate comprising the removable adhesive cover strip is the side opposite to the side of the substrate on which the impermeable membrane 18 is provided.

With reference to FIG. 3, in some embodiments, one or more impregnated substrates 16 or devices 10 are contained within an impermeable sealable package to prevent the release and escape of vapors when not in use. In the illustrated embodiment, an exemplary impermeable sealed package has a body 24 and an end 28 with a resealable opening 30. In alternative embodiments, the sealed package may just have a body with a resealable opening, with no distinct or clearly definable end like end 28 defined thereon. The resalable opening 30 can have any suitable resealable closure, for example a releasable port, a zipper-like seal, a pressure seal, a reusable adhesive seal, or the like). In the illustrated embodiment, resealable opening 30 has a resealable pressure seal 32 such as that commonly found in small plastic bags sold generally to consumers.

In some embodiments, each substrate is pre-dosed with an appropriate quantity of pesticidal composition for easy application within a given treatment volume. In some embodiments, the substrates 16 are pre-dosed with between 10 mL and 100 mL of pesticidal composition. In some such embodiments, the substrates 16 are intended for use in a treatment enclosure having a volume in the range of 10 L to 1000 L, including any volume therebetween e.g. 100, 200, 300, 400, 500, 600, 700, 800 or 900 L. In some embodiments, a plurality of pre-dosed substrates 16 are packaged together in a suitable resealable package, and can be removed individually from a package when needed.

In some embodiments, a pesticidal composition in liquid form is contained in a vessel or reservoir from which vapors are releasable. In some embodiments, vapors are released passively by a wick, diffuser or through a permeable membrane. In some embodiments, diffusion and/or evaporation may be actively aided by a heater, fan, aerator, pump, or other electrical or mechanical means. In some embodiments, evaporation is actively increased or controlled by lowering or modifying the surface tension of the pesticidal composition via electrical or mechanical means. In some embodiments, evaporation is actively increased by adding a chemical agent to the pesticidal composition. In some such embodiments, the chemical agent catalyzes release of vapors of the pesticidal composition from the device. In some embodiments, the chemical agent causes an exothermic reaction that enhances release of vapors of the pesticidal composition from the device.

Some embodiments comprise a means for actively diffusing a pesticidal vapor, such as a fan, pump, or other such mechanical diffuser, an ultrasonic or humidifying diffuser, an evaporative diffuser, a heat diffuser, or other such diffusion-aiding components. Some embodiments comprise a means for increasing or controlling the rate of evaporation of vapors, such as a heater, fan, aerator (e.g. a device for passing air or gas through or over a solution containing a pesticidal composition), aerosolizer (e.g. an atomizer or other device for creating a mist of a pesticidal composition), pump, etc. Some devices comprise mechanical and/or electrical components to achieve the functions described herein.

Devices according to some embodiments of the present invention comprise a portable housing containing a pesticidal composition, gel or substrate as described above. In some embodiments, this housing comprises mesh, slits or holes or other openings (i.e. apertures) through which vapors may be released. In some embodiments, these openings may be opened and closed by appropriate means. In some embodiments, these openings are adjustable to control the rate of release of vapors. In some embodiments, the housing comprises a permeable membrane or porous material that allows vapors to be released while containing any liquid or solid contents of the device. In some embodiments, the permeable membrane or porous material allows for the controlled release of vapors at a desired rate or dose. In some embodiments, the pesticidal composition within the device is refillable.

With reference to FIG. 4a, an example embodiment of a device for passively releasing vapors of a pesticide through a permeable membrane has an enclosure 40 with a pesticidal composition 46 received therein. In some embodiments, the pesticidal composition 46 is provided in enclosure 40 on an impregnated substrate or other vehicle for gradually releasing pesticidal vapors. In some embodiments, the pesticidal composition is spotted on a substrate in liquid form within enclosure 40, and diffuses outwardly within the absorbent substrate, as indicated by dashed line 45 showing the extent of diffusion of pesticidal composition 46 on the substrate in FIG. 4a. Enclosure 40 has a permeable membrane 42 on one edge thereof affixed at a lip 44 to the main body of enclosure 40, so that pesticidal vapours can diffuse out of enclosure 40. In alternative embodiments, a reservoir such as reservoir 55 described below can be provided in enclosure 40 for receiving a pesticidal composition in liquid form and releasing vapors therefrom via permeable membrane 42. In alternative embodiments, a gelled pesticidal composition can replace the substrate impregnated with a pesticidal composition.

In the illustrated embodiment, enclosure 40 has a lip 44. In some embodiments, permeable membrane 42 is coupled to enclosure 40 via lip 44 in any suitable manner. In some embodiments, permeable membrane 42 is coupled to lip 44 by a suitable adhesive, melting or welding process, pressure or fusion method, solvent melt, or the like. In some embodiments, lip 44 is bevelled, for example to avoid having any sharp edges on enclosure 40 that might puncture a bag or other structure that is used to contain enclosure 40, or other enclosures 40 stored together.

Enclosure 40 is generally cuboid in shape, with one edge of the cuboid being defined by permeable membrane 42. This configuration allows a pesticide-impregnated substrate to be inserted inside enclosure 40, while permeable membrane 42 allows pesticidal vapors to diffuse from the pesticide-impregnated substrate. In some embodiments, the sides of enclosure 40 other than the side defined by permeable membrane 42 are made from a non-permeable material (e.g. glass or a suitable plastic), so that enclosure 40 can be placed on a surface without releasing pesticide onto that surface, e.g. to avoid causing damage to that surface. While the exemplary embodiment has been illustrated as generally cuboid, enclosure 40 could be provided with any suitable shape, e.g. spheroid, oval, cylindrical, pyramidal, or the like.

Figure 4B:
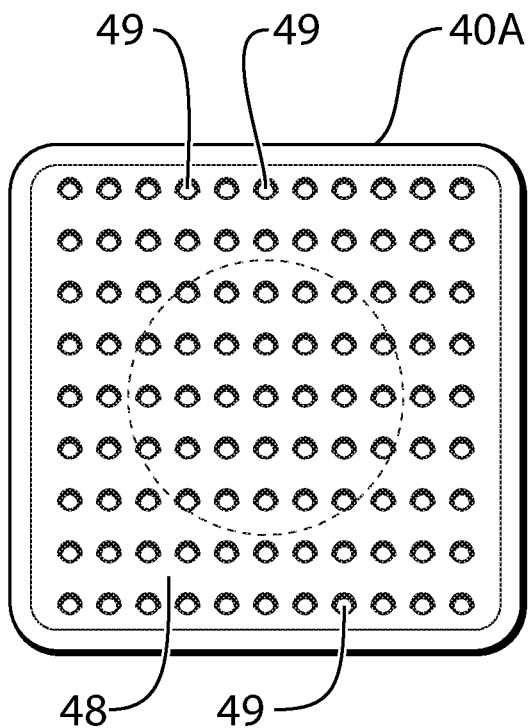

With reference to FIG. 4b, an example embodiment of an alternative enclosure 40A for delivering pesticidal vapors is illustrated. Enclosure 40A is similar to enclosure 40, but has a perforated or mesh surface 48 having a plurality of apertures 49 therethrough that allow for non-adjustable release of pesticidal vapors from a substrate impregnated with a pesticidal composition 46 instead of a permeable membrane 42. In some embodiments, perforated or mesh surface 48 is supported on lip 44 so that surface 48 does not contact the substrate impregnated with pesticidal composition.

Figure 4C:
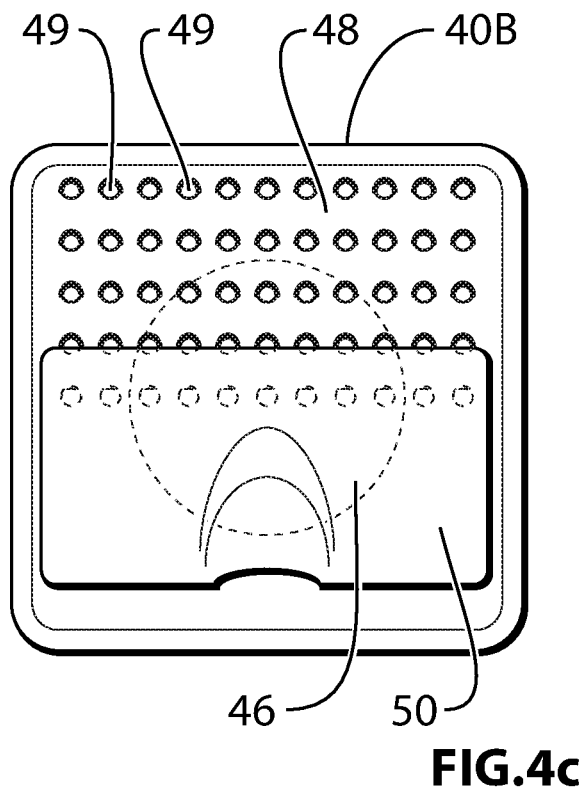

With reference to FIG. 4c, an example embodiment of an alternative enclosure 40B for adjustably delivering pesticidal vapors is illustrated. Enclosure 40B is similar to enclosure 40A, but has an adjustment shield 50 slidably mounted thereon. Perforated or mesh surface 48 on enclosure 40B allows pesticidal vapors to diffuse from a substrate impregnated with a pesticidal composition 46. Adjustment shield 50 is slidable over perforated or mesh surface 48 to obscure some or all of the apertures 49 therethrough. A user can slide adjustment shield 50 to cover more or fewer of apertures 49 to decrease or increase, respectively, the rate of release of pesticidal composition 46 as pesticidal vapors out of enclosure 40B.

In alternative embodiments, perforated or mesh surface 48 could be replaced with a permeable membrane 42.

Figure 5A:
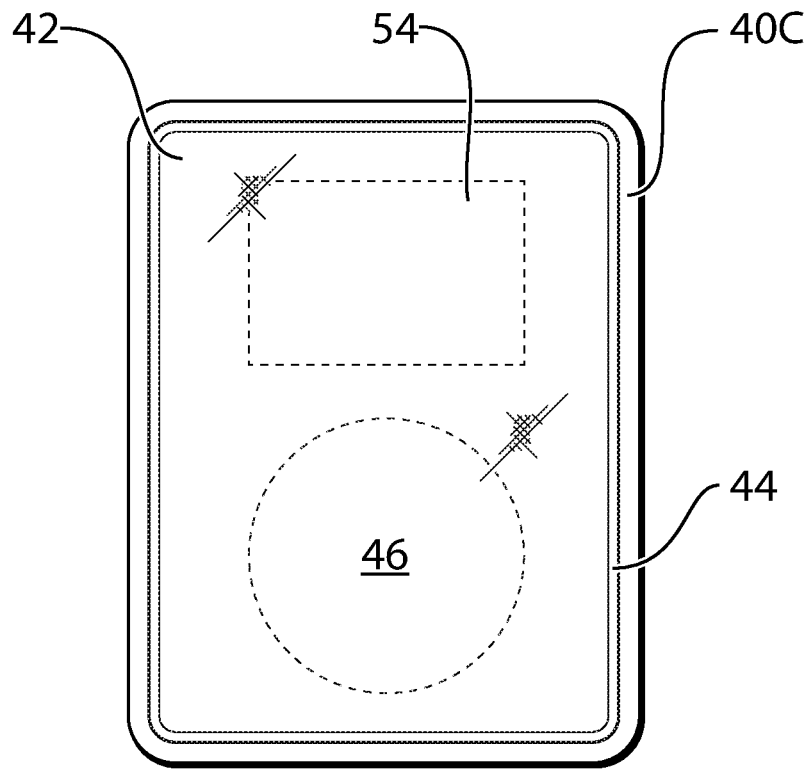
FIG. 5abc show non-passive versions of devices with a permeable membrane (FIG. 5a), a non-adjustable venting method (FIG. 5b) and an adjustable venting method (FIG. 5c) in accordance with some example embodiments of the invention.

With reference to FIG. 5a, an example embodiment of a device for actively diffusing pesticidal vapors from a substrate impregnated with a pesticidal composition 46 (or a gelled pesticidal composition, or a reservoir containing a liquid pesticidal composition in alternative embodiments) is illustrated. Enclosure 40C has a permeable membrane 42 for allowing release of pesticidal vapors therefrom, and a bevelled region 44 connecting permeable membrane 42 to the main body of enclosure 40C. Enclosure 40C further includes a diffusion/evaporation aid 54. Examples of diffusion/evaporation aids that could be used in some embodiments include a heater, fan, aerator, pump, or other electrical or mechanical means. Diffusion/evaporation aid 54, when operated, acts to enhance or increase the rate of release of pesticidal vapors from enclosure 40C. In some embodiments, a user can control the level of operation (e.g. the temperature setting of a heater, or the speed of rotation of a fan) or the length of time that diffusion/evaporation aid 54 is operated to enhance the release of pesticidal vapours to a desired level. In some embodiments, a user can provided a directionality to the operation of diffusion/evaporation aid 54, for example by adjusting a direction of output of a fan, for example in order to direct vapors to a specific area or to concentrate vapors in a specific region.

Figure 5B:
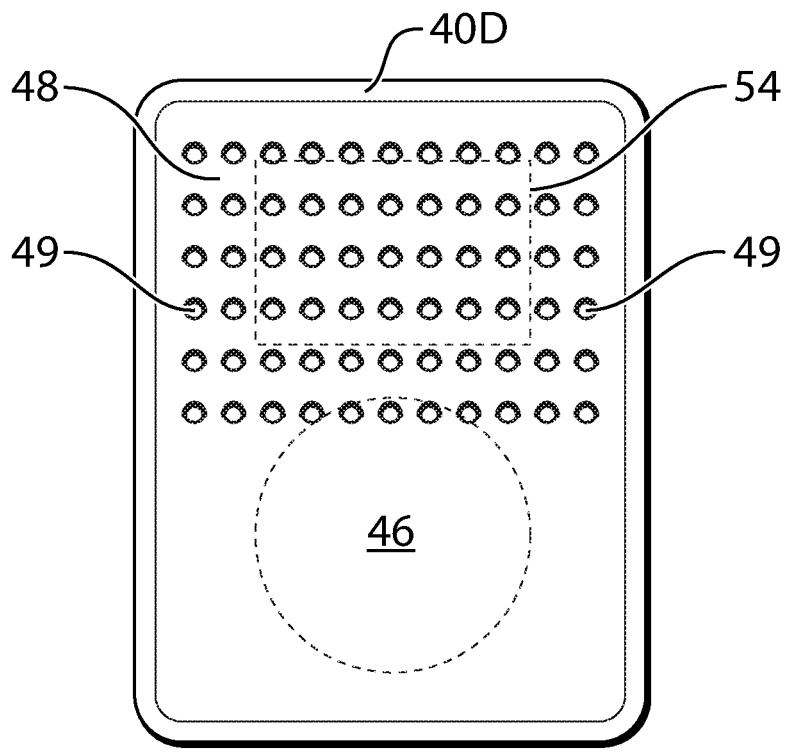

With reference to FIG. 5b, another example embodiment of a device for actively diffusing pesticidal vapors from a substrate impregnated with a pesticidal composition is illustrated. Enclosure 40D is similar to enclosure 40C, but rather than having a permeable membrane 42, enclosure 40D has a non-adjustable perforated or mesh surface 48 to facilitate venting (i.e. release) of pesticidal vapors of pesticidal composition 46 through apertures 49 therein. A diffusion/evaporation aid 54 is provided to enhance or increase the rate of release of pesticidal vapors through apertures 49 when operated.

Figure 5C:
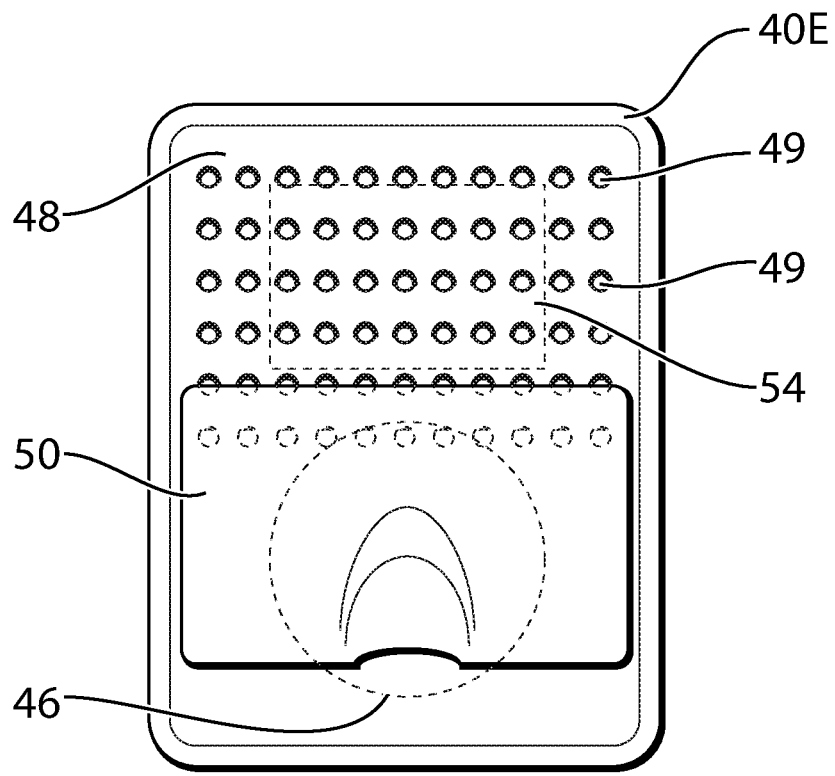

With reference to FIG. 5c, another example embodiment of a device for actively diffusing pesticidal vapors having an adjustable venting method is provided. Enclosure 40E is generally similar to enclosure 40D, but is further provided with an adjustment shield 50 that can be slid by a user to cover some or all of apertures 49 on perforated or mesh surface 48, so that a user can regulate the rate of release of pesticidal composition 46 by another mechanism other than regulation of diffusion/evaporation aid 54.

Figure 6:
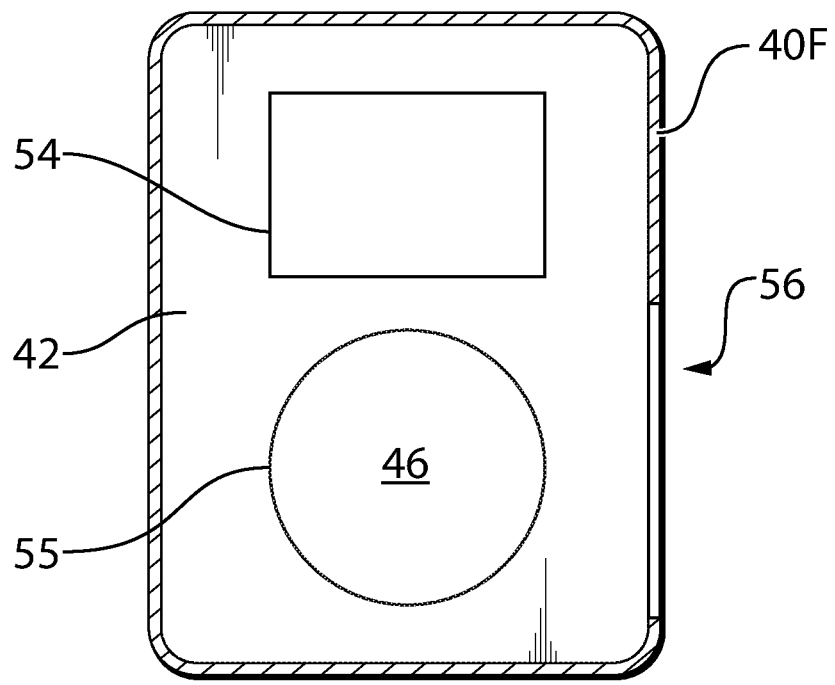
FIG. 6 is a schematic cross-sectional view showing a non-passive device with a view of the interior components and a refilling port in accordance with an example embodiment of the invention.

With reference to FIG. 6, a further example embodiment of a non-passive device for releasing pesticidal vapors is illustrated in cross-section. Enclosure 40F includes a permeable membrane 42 for allowing release of pesticidal vapors from a reservoir 55 with a pesticidal composition 46 contained therein. Enclosure 40F includes a diffusion/ evaporation aid 54 for stimulating the release of pesticidal vapors from pesticidal composition 46, to enhance the release of pesticidal vapors through permeable membrane 42. Enclosure 40F further includes a refilling port 56, which allows a user to add further pesticidal composition 46 to enclosure 40F.

In some embodiments, pesticidal composition 46 is provided as a "puck", i.e. a substrate impregnated with a pesticidal composition, or a solution of a pesticidal composition contained within a permeable membrane that contains the liquid form of the pesticidal composition but allows diffusion of vapours therefrom, or a gel containing a pesticidal composition, and refilling port 56 allows a user to remove a spent puck from enclosure 40F and insert a fresh puck therein. In other embodiments, refilling port 56 provides an access pathway so that a user can use a pipettor or other dispensing device to add additional liquid pesticidal composition 46 to reservoir 55.

Figure 7:
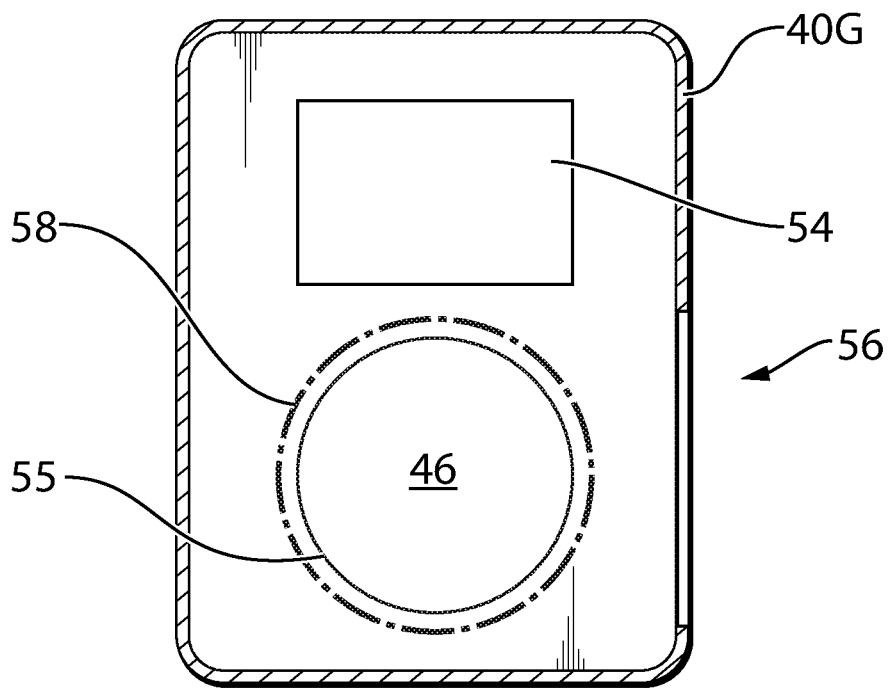
FIG. 7 is a schematic cross-sectional view showing a non-passive device with a wick, diffuser or permeable membrane at least partially surrounding the reservoir in accordance with an example embodiment of the invention.

With reference to FIG. 7, a further example embodiment of a non-passive device is illustrated. Enclosure 40G has a reservoir 55 for receiving a pesticidal composition 46. At least a portion of the perimeter of reservoir 55 (and the entire perimeter in the illustrated embodiment) is provided with a diffusion member, for example, a wick, diffuser or permeable membrane, illustrated schematically as 58. In some embodiments, diffusion member 58 is formed of the same materials as permeable membrane 42, or from any suitable substrate. Diffusion member 58 facilitates diffusion of pesticidal vapors from pesticidal composition 46. Enclosure 40G also includes a diffusion/evaporation aid 54, to further enhance the release of pesticidal vapors from pesticidal composition 46. Enclosure 40G also includes a refilling port 56, to allow additional pesticidal composition 46 to be introduced therein. In the embodiment of enclosure 40G, pesticidal composition 46 would typically be provided as a liquid composition that could flow into the wick, diffuser or permeable membrane 58.

Figure 8:
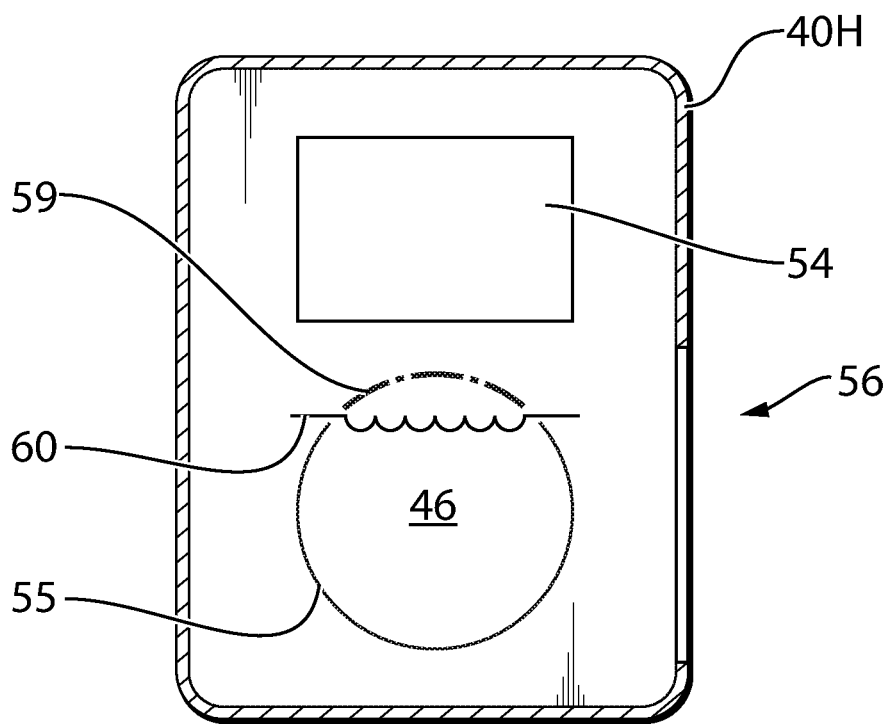
FIG. 8 is a schematic cross-sectional view showing a non-passive device with a means to alter surface tension in accordance with an example embodiment of the invention.

With reference to FIG. 8, a further example embodiment is illustrated. Enclosure 40H has a reservoir 55 for containing a pesticidal composition 46. The reservoir 55 is partially bounded by a diffusion member 59, such as a wick, diffuser or permeable membrane. Diffusion member 59 is generally similar to diffusion member 58, except that it is provided along only a portion of reservoir 55. A surface tension modification device 60 is provided associated with reservoir 55, for modifying the surface tension of the pesticidal composition 46 contained in reservoir 55. In some example embodiments, suitable means for modifying the surface tension include a mechanism for bubbling air or another gas through reservoir 55, a vibrator, a sonicator, an impeller or other agitator, electrodes, or the like. In some embodiments, decreasing the surface tension of a liquid contained in reservoir 55 may allow the pesticidal composition 46 to flow more easily through fibres or across a membrane or other surface, in order to increase the rate of vapor release from that composition. This is another means of active diffusion. In the embodiment of enclosure 40H, pesticidal composition 46 would be provided as a liquid composition.

In some embodiments, some devices allow for easy assessment by users of the quantity of product remaining. Some devices with a liquid store of pesticidal composition allow for visual windows onto the fill level or for floats to indicate the amount of liquid remaining. Devices which incorporate a composition-impregnated substrate may have the substrate change color depending on its moisture level. In yet other embodiments, gel substrates may co-evaporate with or otherwise degrade with the evaporation of the pesticidal composition, such that the quantity of pesticidal composition remaining is indicated by the quantity of substrate remaining. In other embodiments, solid substrates may degrade with the evaporation of the pesticidal composition, so that the quantity of pesticidal composition remaining is indicated by the quantity of substrate remaining.

Figure 9A:
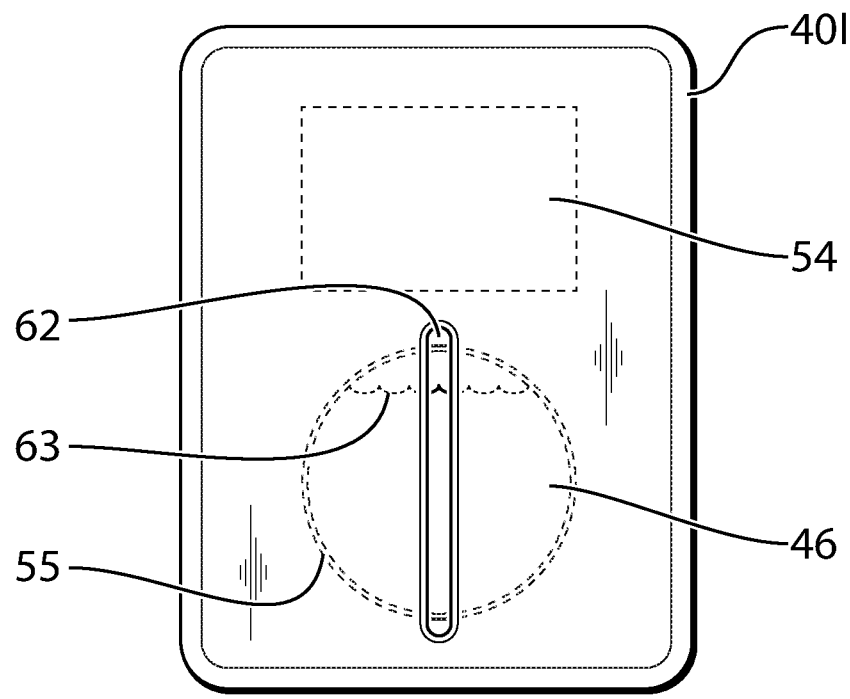
FIG. 9abc are schematic drawings showing non-passive versions of devices with a viewing window (FIG. 9a), a float (FIG. 9b) and a co-evaporating/color changing substrate (FIG. 9c) in accordance with example embodiments of the invention.
Figure 9B:
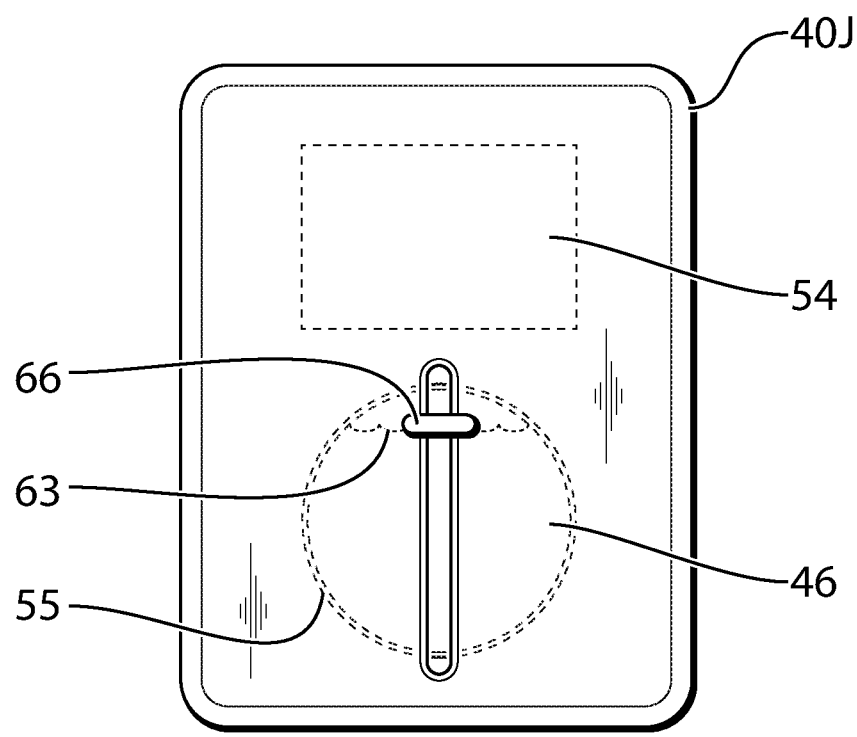
Figure 9C:
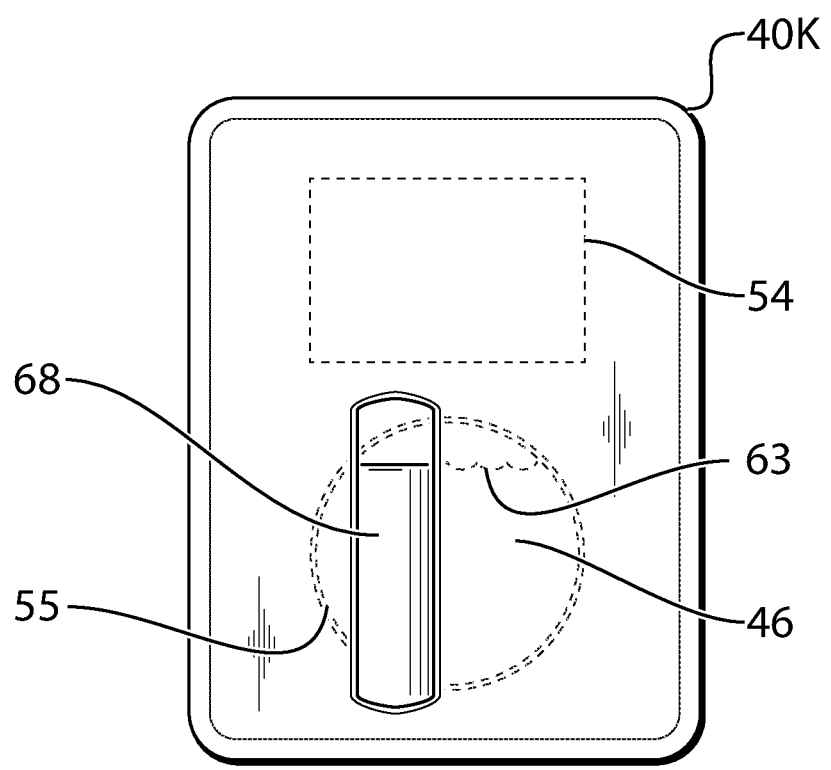

FIGS. 9a, 9b and 9c illustrate example embodiments of non-passive devices for releasing pesticidal vapors. These example embodiments include visual indicators to indicate the amount of pesticidal composition 46 remaining in the device.

The example embodiment of an enclosure 40I illustrated in FIG. 9a has a viewing window 62 that allows a user to visually ascertain the level 63 of a liquid pesticidal composition 46 within a reservoir 55 of the device. In some such embodiments, a refilling port similar to refilling port 56 is provided, so that a user can refill the liquid pesticidal composition 46 within reservoir 55 when the level 63 is observed to fall below a predetermined level.

The example embodiment of an enclosure 40J illustrated in FIG. 9b has a visual indicator, a float 66 in the illustrated embodiment, that provides a visual indication on the outside of enclosure 40J of the level 63 of liquid pesticidal composition 46 remaining in reservoir 55. In some such embodiments, a refilling port similar to refilling port 56 is provided, so that a user can refill the liquid pesticidal composition 46 within reservoir 55 when the level 63, as indicated by float 66, is observed to fall below a predetermined level.

The example embodiment of an enclosure 40K shown in FIG. 9c has a colored co-evaporating substance 68 that evaporates at the same or a similar rate as pesticidal composition 46 contained within reservoir 55. Thus, a user can ascertain the level 63 of pesticidal composition 46 remaining in reservoir 55 by viewing the level of the colored co-evaporating substance 68. In some such embodiments, a refilling port similar to refilling port 56 is provided, so that a user can refill the liquid pesticidal composition 46 within reservoir 55 when the level 63, as indicated by visual inspection of colored co-evaporating substance 68, is observed to fall below a predetermined level. In alternative embodiments, a similar colored visual indication of the level of pesticidal composition remaining in the device could be provided by the use of a color-changing substrate (i.e. a substrate that changes color as it dries out), or by providing a separate reservoir of a colored volatile compound that evaporates at a rate similar to pesticidal composition 46.

Some embodiments of the present invention allow for a controlled release of a particular dose of a pesticidal vapor. Some devices according to the present invention include a means for monitoring and/or self-regulating the dose of pesticidal vapor that is released over time. In some devices, this monitoring and/or self-regulating is accomplished by measuring a weight change over time of the device or the substrate or composition contained in the device.

Figure 10:
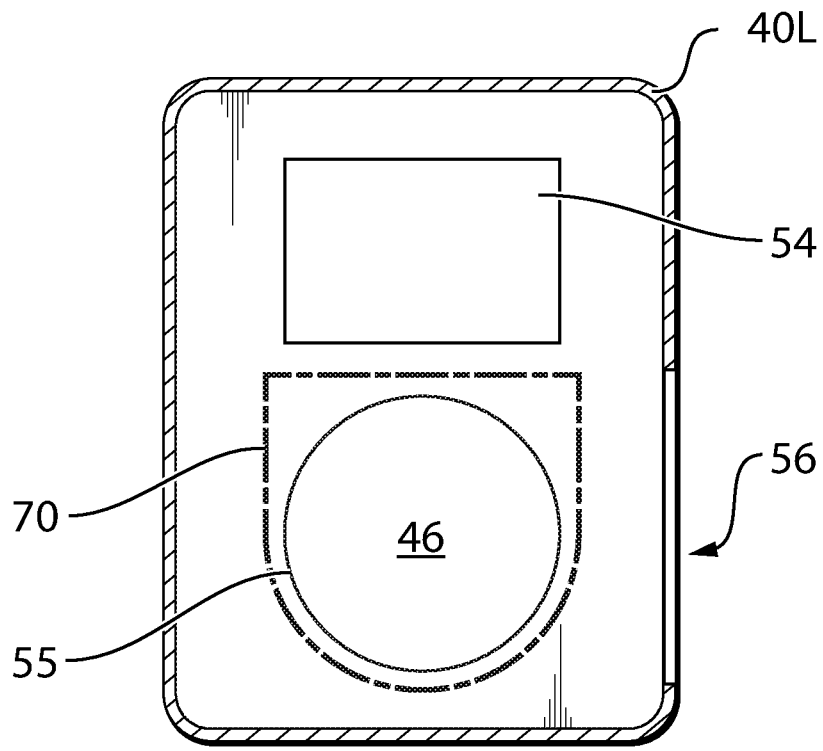
FIG. 10 shows a non-passive device with a monitoring and/or self-regulating component in accordance with an example embodiment of the invention.
Figure 11:
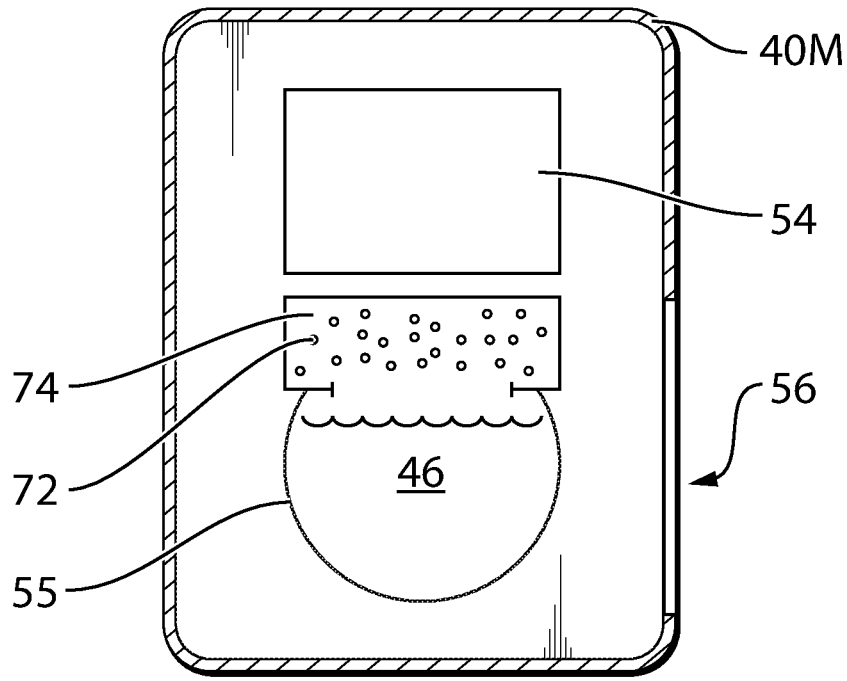
FIG. 11 shows a schematic cross-sectional view of a non-passive device employing an activation agent in accordance with an example embodiment of the invention.

FIG. 10 shows an example embodiment of a non-passive device for releasing pesticidal vapors with a monitoring and/or self-regulating component 70. Enclosure 40L has a pesticidal composition 46 contained within a reservoir 45, and a diffusion/evaporation aid 54 to promote release of pesticidal vapors. Enclosure 40L further includes a monitoring and/or self-regulating component 70, which is a device for measuring the change in weight over time of the pesticidal composition 46 contained in reservoir 55. Enclosure 40L also includes a refilling port 56. In some embodiments, a user can add more pesticidal composition 46 to enclosure 40L through refilling port 56 in response to a signal or indication by monitoring and/or self-regulating device 70 indicating that the level of pesticidal composition 46 in reservoir 55 has dropped below a predetermined level. Such a signal can be generated by any suitable means, e.g. a visual indication, an audible indication, an electrical signal transmitted by wired or wireless means to a monitoring station, or the like.

FIG. 11 shows an example embodiment of a non-passive device, enclosure 40M, having an activation agent 72 that enhances the release of pesticidal vapors from pesticidal composition 46. In some embodiments, including the illustrated embodiment, activation agent 72 is contained in a well, reservoir, or other structure such as reservoir 74, that can be placed in fluid communication with reservoir 55. Activation agent 72 can be any suitable agent that interacts with pesticidal composition 46 to enhance the release of vapors therefrom, for example, a catalyst, enzyme or other reaction initiator, or a chemical compound that causes an exothermic reaction to heat pesticidal composition 46 and thereby increase the rate of release of pesticidal vapors therefrom. In some embodiments, enclosure 40M also includes a diffusion/evaporation aid 54, to further assist in increasing the release of vapor from pesticidal composition 46. In some embodiments, enclosure 40M includes a refilling port 56, to facilitate adding additional pesticidal composition 46 to enclosure 40M.

In some devices, the pesticidal composition or impregnated substrate is formulated to release vapors upon contact with an activation agent. The activation agent may chemically react with the pesticidal composition or substrate, or serve as a catalyst to a chemical reaction, that releases vapors. In some embodiments the activation agent is water or another solvent. Without being bound by theory, water or another solvent may act as an activation agent by (1) dissolving or emulsifying an insecticidal composition which then enters a vapor phase with evaporating water; (2) water may be miscible with at least one component of an pesticidal composition and when combined, the water and the component co-evaporate at a higher rate and/or lower temperature than the component would evaporate at if not combined with water; and/or (3) exothermic reactions with water (e.g. an acid-base reaction) can heat the pesticidal composition to increase its evaporation rate. In some embodiments, the user triggers the release of vapors by adding the activation agent to the device, or otherwise causing the activation agent to come into contact with the pesticidal composition or substrate in the device.

In some embodiments, the activation agent is a chemical compound that causes an exothermic reaction, for example, calcium oxide, nitrocellulose potassium nitrate, peroxide of potassium permanganate, or the like, as described in JP 394189382 and TW 201306740A, both of which are incorporated by reference herein. In some embodiments, in a device for releasing pesticidal vapors, a chemical compound that causes an exothermic reaction is added to a water bath that surrounds and/or contacts a substrate impregnated with a pesticidal composition via an interposed impermeable layer, so that heat from the water bath is transferred to the substrate.

In some embodiments, a device for providing vapors of a pesticidal composition has a pump or other discharge mechanism for releasing a controlled amount of a pesticidal solution from a liquid reservoir onto a substrate from which pesticidal vapors can be released from the pesticidal solution. In some such embodiments, the pump is set to deliver a pre-determined amount of liquid pesticidal composition to the substrate to replace the pesticidal composition that is being released as a vapor at approximately the same rate that the pesticidal composition is released as vapor. In some such embodiments, the pump is set to deliver a pre-determined amount of liquid pesticidal composition to the substrate to maintain a substantially constant concentration of pesticidal vapor within a treatment enclosure. In some embodiments, the pump is set to deliver a pre-determined amount of liquid pesticidal composition to the substrate periodically over time, to periodically deliver an effective amount of pesticidal vapor within a treatment enclosure to control pests within the treatment enclosure on an ongoing basis or at multiple time intervals. In some embodiments, the pump is set to deliver a pre-determined amount of liquid pesticidal composition for a prolonged period of time, for example from 1 day to 6 months, or any period of time therebetween, e.g. 15 days, 30 days, 45 days, 60 days, 3 months, 4 months or 5 months. In some embodiments, the pump is set to deliver a pre-determined amount of liquid pesticidal composition a specified intervals, e.g. for 2 days every month on an ongoing basis.

With reference to FIG. 12*a*, an example embodiment of a pillow-packaged substrate 200 that provides a device for releasing pesticidal vapors is illustrated. Pillow-packaged substrate 200 has an outer housing 202 made from an impermeable material, containing a substrate 204 impregnated with a pesticidal composition therein. In the illustrated embodiment, outer housing 202 is formed from top and bottom layers of impermeable material, sealed together along their edges to define a space therein for receiving substrate 204. FIG. 12*a* shows the substrate 204 and outer housing 202 adjacent one another to better show the features of pillow packaged substrate 200. In some embodiments, substrate 204 is impregnated with pesticidal composition and placed inside outer housing 202, which is then sealed. Outer housing 202 remains sealed until a user is ready to use substrate 204 to release pesticidal vapors. The user then opens outer housing 202 in any suitable manner and removes substrate 204 for use.

Examples of suitable impermeable materials that can be used to form outer housing 202 include any suitable plastic or similar impermeable material, including polyesters like polyethylene, low/medium and high density polyethylene, biaxially-oriented polyethylene terephthalate (e.g. Mylar™), polypropylene, biaxially oriented polypropylene, metalized polyester, nylon, biaxially oriented nylon, paper poly foil poly, ethylene-vinyl acetate, film foil laminations, poly extrusion laminations, and the like.

FIG. 12*b* shows an example embodiment of a pillow-packaged substrate 200A. Pillow-packaged substrate 200A is generally similar to pillow-packaged substrate 200, except that outer housing 202A includes a peel strip 206 one face thereof. Peel strip 206 can be peeled back from the main body of outer housing 202A to reveal a perforated surface 208 of outer housing 202A. Perforated surface 208 is provided with a plurality of apertures 210. When peel strip 206 is in the sealed position, perforated surface 208 (and more specifically, all of apertures 210) are sealingly covered by peel strip 206. In some embodiments, substrate 204 is impregnated with a pesticidal composition and placed inside outer housing 202A, which is then sealed. Outer housing 202A remains sealed, until a user is ready to use substrate 204 to release pesticidal vapors. The user then peels back peel strip 206 to expose some or all of apertures 210 on perforated surface 208, so that pesticidal vapors can be released from pillow-packaged substrate 200A via apertures 210.

Figure 12A:
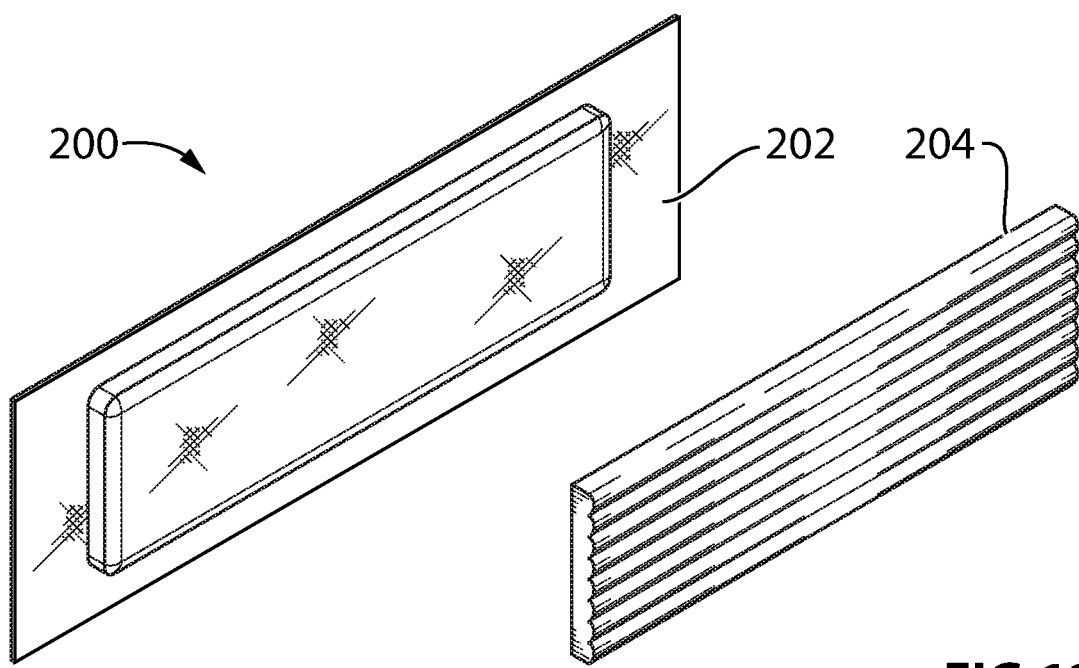
FIG. 12abc illustrate schematically a pillow-packaged substrate according to some example embodiments.
Figure 12B:
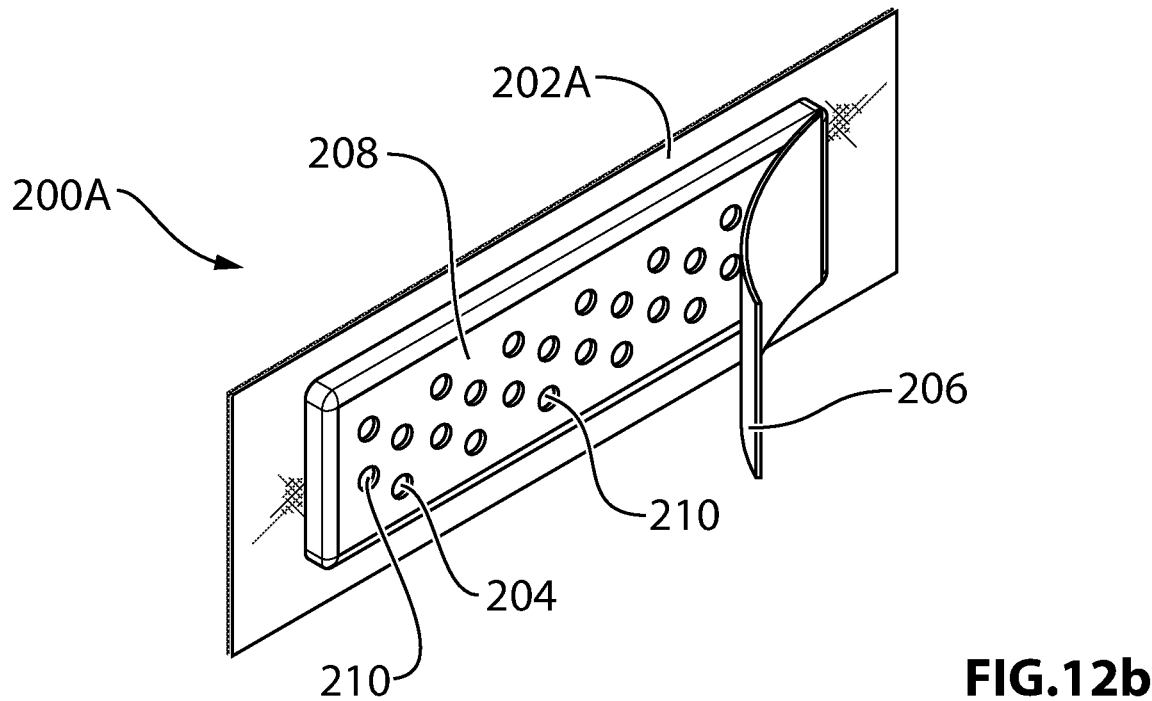
FIG. 12b shows the impregnated substrate in a sealed package with vent apertures covered by a peel strip.
Figure 12C:
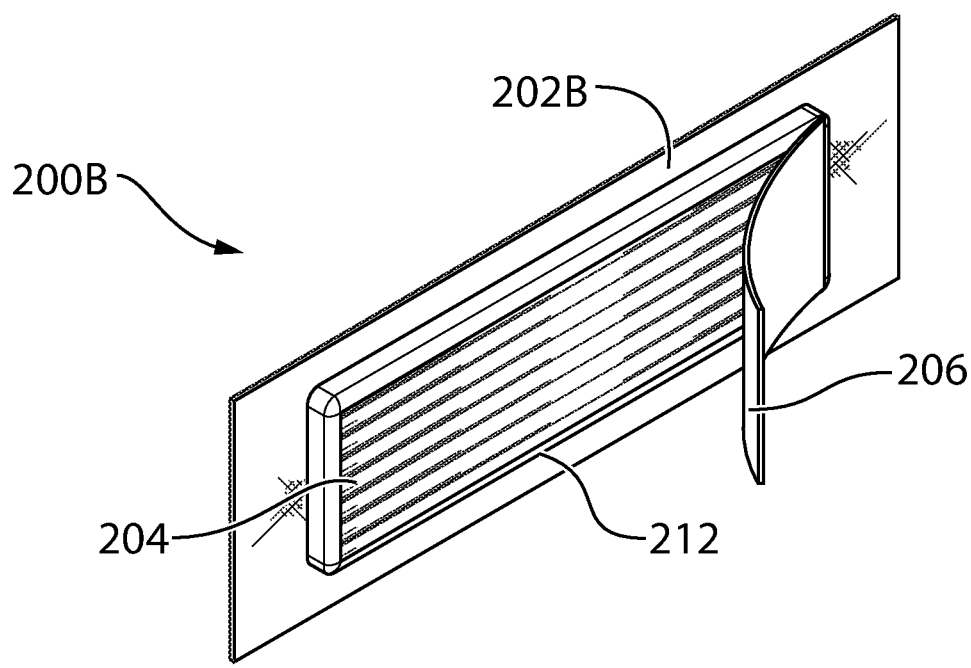
FIG. 12c shows the impregnated substrate in a sealed package with a venting window covered by a peel strip.

FIG. 12c shows an example embodiment of a pillow-packaged substrate 200B. Pillow-packaged substrate 200B is generally similar to pillow-packaged substrate 200A, except that a window 212 is provided in place of perforated surface 208. In the illustrated embodiment, window 212 comprises a generally rectangular opening in outer housing 202B that is initially sealingly covered by peel strip 206. Peel strip 206 can be pulled back to uncover window 212, thereby exposing substrate 204. In some embodiments, substrate 204 is impregnated with a pesticidal composition and placed inside housing 202B, which is then sealed. Outer housing 202B remains sealed until a user is ready to use substrate 204 to release pesticidal vapors. The user then peels back peel strip 206 to expose all or part of window 212, so that pesticidal vapors can be released from pillow-packaged substrate 200B.

In alternative embodiments, rather than covering perforated surface 208 or window 212 with a peel strip 206, outer housing 202A or 202B could instead be provided with a series of cut lines, and a user could cut or tear along the cut lines to remove a portion of outer housing 202 and expose perforated surface 208 and/or window 212.

Figure 12D:
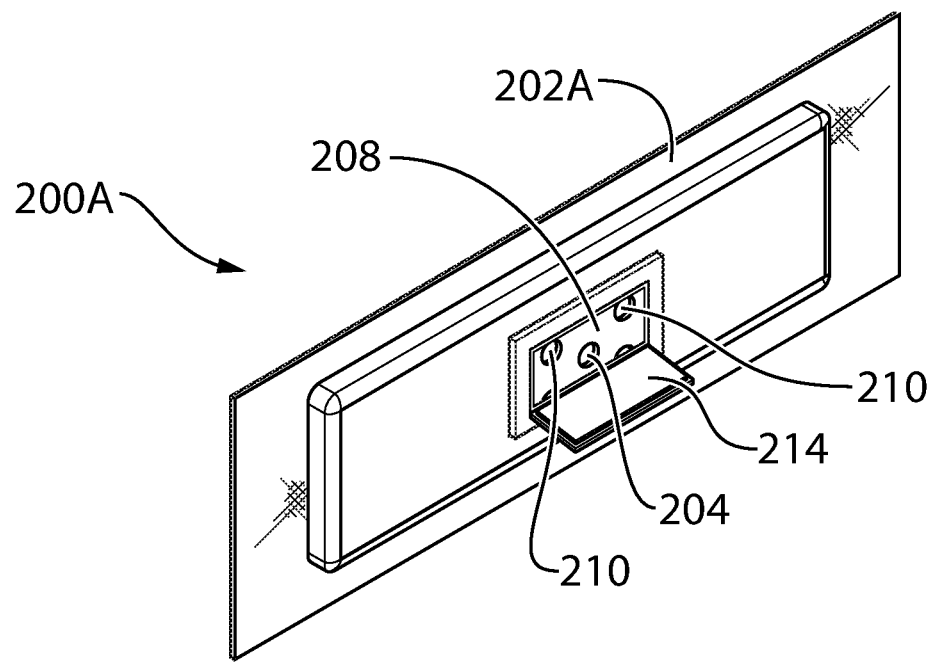
FIG. 12d shows the impregnated substrate in a sealed package with a rigid resealable closure covering vent apertures.

In alternative embodiments, rather than peel strip 206 being made of a flexible material, outer housing 202A or 202B could be provided with a rigid resealable closure, for example in the nature of rigid resealable plastic closures provided on packaging of consumer wet wipes. The rigid resealable closure could be opened and closed by a user to expose perforated surface 208 or window 212 only at desired times, and could contain pesticidal vapors within substrate 204 to preserve pillow-packaged substrate 200A or 200B for future uses. An example of such an embodiment is illustrated in FIG. 12d, in which pillow-packaged substrate 200A has a rigid plastic resealable closure 214 covering perforated surface 208 (including apertures 210 and substrate 204) instead of a peel strip 206.

Some embodiments of the present invention provide methods for killing or controlling a pest comprising placing a pesticidal composition, substrate or device as described above in the vicinity of a target pest, such that the pest is exposed to the vapors released from the composition, substrate, or device.

In some embodiments, methods comprise placing the composition, substrate or device in an enclosed volume of space (i.e. a treatment enclosure) such that released pesticidal vapors accumulate within the enclosed space and effectively kill or control any target pest within the space over a period of time. In some embodiments, the enclosed space is a sealable container containing objects that are infested or potentially infested by a target pest. In some embodiments, the enclosed space is a container that can be partially enclosed containing objects that are infested or potentially infested by a target pest. In some embodiments, the enclosed space is a container that is only partially permeable to pesticide vapors, and the container contains objects that are infested or potentially infested by a target pest. Examples of enclosed spaces or sealable containers that can provide a treatment enclosure in some embodiments include bags, garbage bags, garbage or recycling bins, boxes, suitcases, back packs, duffel bags, clothes bags, cabinets, totes, barrels, pet kennels and crates, shipping containers (including intermodal, standard, high-cube, hard top, ventilated, refrigerated, insulated and tank containers and the like), vehicles such as cars, trucks, buses, boats, train cars, recreational vehicles, motorhomes, cube vans, transport trucks, boats and the like, including public transportation vehicles, closets, rooms, hotel rooms, offices, dormitories, storage lockers, warehouses, greenhouses, public auditoriums (for example, theaters, concert halls, lecture halls and the like), refrigerators/freezers, bee hives, food storage containers, pre-sealed packages containing food or non-food items, retail food bags, food storage structures (e.g. silos and the like, including fruit storage containers), library shelves enclosed in sheets of plastic, book bins, and the like.

In some embodiments, the sealable containers are made of a material that is impermeable to vapors. In some embodiments, the enclosed space or sealable containers are sealed by wrapping or affixing an impermeable membrane around the space or over any areas through which vapors may leak out. In some embodiments, this impermeable membrane is stretchable plastic wrap or tape. In some embodiments, the enclosed space or sealable container is further placed within a sealed room or chamber. In some embodiments, the period of time the container is sealed or left in its enclosed state is at least 15 minutes, at least 30 minutes, at least 1 hour, at least 2 hours, at least 4 hours, at least 6 hours, at least 8 hours, at least 12 hours, at least 16 hours, or 1, 2, 3, 4, 5, 6, or 7 days, or more.

In some embodiments, a treatment enclosure is provided on a live animal, for example a mammal such as a companion animal, livestock or a human, by providing an impermeable membrane such as plastic around at least a portion of the animal. For example, external parasites such as fleas, lice, ticks, bog-flies, mites or the like, can be treated on an animal by providing a bag around the animal from which its head protrudes. The bag can be sealed around the infested portion of the animal, and pesticidal vapors released within the bag to control pests located directly on the animal. In some embodiments, an impermeable cap, similar to a shower cap, is provided that can be placed on the head of a human as a treatment enclosure to contain pesticidal vapors to control a pest located in the hair or scalp of the human, for example lice or ticks. In some embodiments, the animal is a dog, cat, mouse, hamster, guinea pig, bird, horse, cow, sheep, goat, pig, duck, turkey, chicken or the like.

In some embodiments, a treatment enclosure is provided on one or more live plants. For example, a plant (e.g. a potted house plant) or a group of plants (e.g. a row of plants) is covered by a bag or other impermeable membrane, and pesticidal vapors are released inside the impermeable membrane to control pests associated with the plant. Examples of pests that can be controlled in this manner include all life stages of aphids, ants, spider mites and other mites, thrips, beetles, moths, scales, mealybugs, and other arthropods that may infest plants. In some embodiments, the amount of pesticidal vapor released within the treatment enclosure is selected to differentially control an undesirable pest, while not harming one or more other beneficial arthropod species, for example ladybugs (which are predators of pests such as aphids) or bees or other pollinators.

In some embodiments, a method is provided for treating objects that are infested or potentially infested by pests comprising placing the infested objects in a container, placing a pesticidal composition, substrate or device as described above into the container, and sealing the container for a sufficient time to allow the vapors of the pesticidal composition to kill or otherwise control the pests and/or its eggs.

Figure 13:
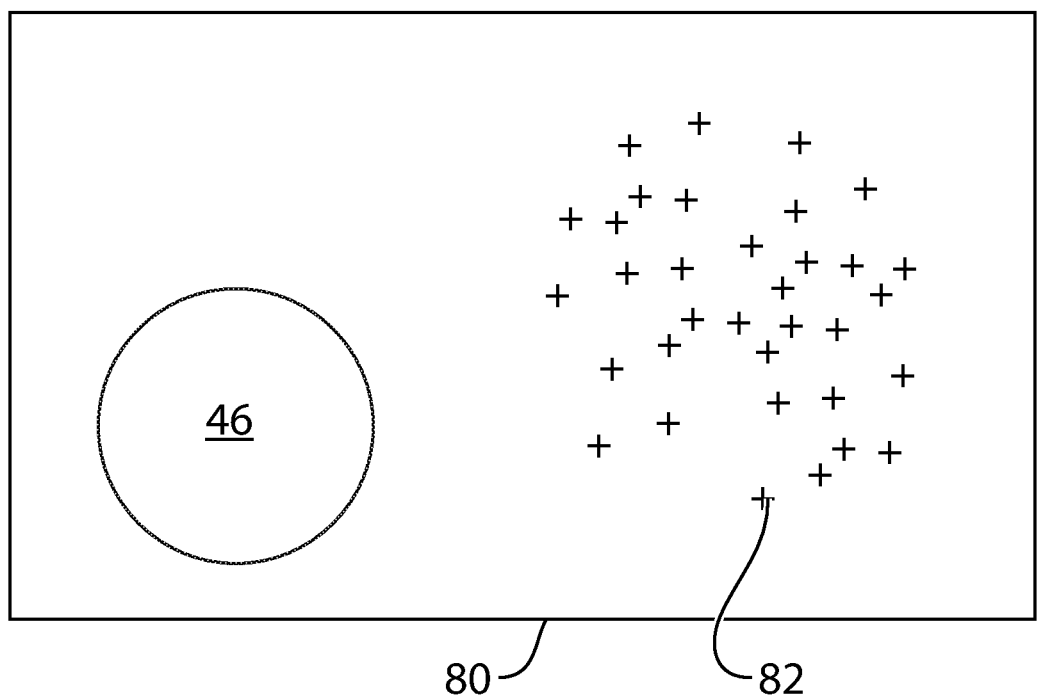
FIG. 13 shows schematically a pesticidal composition in an enclosed space with target pests in accordance with an example embodiment of the invention.

With reference to FIG. 13, an example embodiment of a treatment enclosure 80 in which a pesticidal composition 46 is used to treat a target pest 82 is schematically illustrated. The target pest 82, and/or an article infested with a target pest 82, and a pesticidal composition 46 that releases pesticidal vapors are placed together within a treatment enclosure 80. The source of pesticidal vapors from pesticidal composition 46 is left in treatment enclosure 80 for a sufficient period of time to control the target pest 82.

In some embodiments, a device for releasing pesticidal vapors, a pesticide-impregnated substrate, or a gelled pesticidal composition is provided as an integral part of a treatment enclosure into which infested articles can be inserted for treatment. With reference to FIG. 14a, an example embodiment of a treatment enclosure 250 is illustrated. Treatment enclosure 250 has an impermeable or substantially impermeable outer layer 252. In some embodiments, impermeable outer layer 252 is a plastic bag. At least one substrate, gel or device 254 for releasing an effective amount of a pesticidal vapor is adhered to or otherwise provided within outer layer 252. In some embodiments, the substrate, gel or device 254 is covered by a protective mesh or wire housing 255, to prevent direct contact between infested articles inserted in outer layer 252 and vapor release device 254. In some embodiments, protective mesh or wire housing 255 is directly secured on the inside surface of outer layer 252. In some embodiments, a plurality of substrates, gels and/or devices 254 are provided within outer layer 252.

In the illustrated embodiment, outer housing 252 is provided with a resealable opening 256. In use, a user can open resealable opening 256, insert infested articles inside outer housing 252, re-seal resealable opening 256, leave opening 256 sealed for a predetermined treatment period (e.g. 1 hour, 1 day, one week, or any time interval therebetween) to control pests associated with the infested articles, and then open resalable opening 256 to remove the treated articles.

In some embodiments, including the illustrated embodiment, outer housing 252 is provided with a tear strip 258 or other suitable member that sealingly covers opening 256, to prevent the inadvertent release of pesticidal vapors from treatment enclosure 250 before a user is ready to insert infested articles. For example, tear strip 258 could be a partially perforated section of plastic or the like, which is initially sealed, but which can be easily torn off by a user to access opening 256 when it is intended to use treatment enclosure 250 (e.g. similar to tear away plastic coverings over resealable openings on commercially sold food items).

In the embodiment illustrated in FIG. 14b, an example embodiment of a multi-layered treatment enclosure 250A is illustrated. Treatment enclosure 250A has an impermeable or generally impermeable outer housing 252, and an inner substrate lining 260 that is a substrate impregnated with a pesticidal composition. Inner substrate lining 260 sits inside outer housing 252 and lines the inside surface of treatment enclosure 250, to release pesticidal vapors to treat infested articles placed therein. Inner substrate lining 260 is pre-dosed with an effective amount of a pesticidal composition to provide an effective vapor concentration to control pests associated with infested articles inserted in treatment enclosure 250A. As in the illustrated embodiment, in some embodiments, a permeable inner membrane 262 is provided on the inside surface of inner substrate lining 260, to prevent infested articles from coming in direct contact with inner substrate lining 260 while allowing pesticidal vapors to permeate throughout the volume of the treatment enclosure 250A. In some embodiments, permeable inner membrane 262 is omitted. Treatment enclosure 250A is provided with a resalable opening 256, so that a user can insert and seal infested articles within treatment enclosure 250A for a treatment period.

With reference to FIG. 14c, an example embodiment of a reusable treatment enclosure 250B is illustrated. Treatment enclosure 250B has an outer impermeable layer 252 and a resealable opening 256, to allow a user to insert and remove infested articles from treatment enclosure 250B after a suitable treatment period. Treatment enclosure 250B further has at least one side pocket 264, and may have a plurality of side pockets 264. The outer surface of side pocket 264 is continuous with outer impermeable layer 252, or is sealingly engaged therewith. The inner surface of side pocket 264 comprises a permeable membrane 266. A source of pesticidal vapors 270, which can be a device for releasing pesticidal vapors, a substrate impregnated with a pesticidal composition, or a gel of a pesticidal composition, can be placed within pocket 264 via a resealable opening 268. Vapors released from the source of pesticidal vapors 270 can diffuse into the interior of treatment enclosure 250B via permeable membrane 266. In use, a user inserts infested articles into enclosure 250B via resealable opening 256, and inserts a source of pesticidal vapors into side pocket 264 via resealable opening 268. Both openings 256 and 268 are sealed, and the infested articles are left within the sealed treatment enclosure 250B for a predetermined treatment period to control pests on the infested articles. The articles can then be removed from treatment enclosure 250B, and the spent source of pesticidal vapors 270 can be removed from side pocket 264 and disposed of in a suitable manner. Treatment enclosure 250B is then ready for subsequent re-use to control pests on infested articles by repeating the above steps.

In some embodiments, outer layer 252 of treatment enclosure 250B is a pliable impermeable membrane, such as a plastic bag. In some embodiments, outer layer 252 of treatment enclosure 250B is a more durable material, for example rigid plastic or rubber, metal, wood, cardboard, expanded polystyrene, glass or the like to facilitate long term re-use of treatment enclosure 250B. In some embodiments, professional pest control personnel may maintain a stock of reusable treatment enclosures similar to treatment enclosure 250B, to facilitate repeated treatment of infested articles.

With reference to FIG. 14d, a single-layer treatment enclosure 250C is illustrated. Treatment enclosure 250C comprises a single layer 252C that is impermeable or generally impermeable to pesticidal vapors. Single layer 252C is also impregnated with a pesticidal composition, so that when infested articles are placed within treatment enclosure 250C, the infested articles will be exposed to an effective amount of pesticidal vapor to control pests on the infested articles. Treatment enclosure 250C can be closed in any suitable manner, for example using a resealable opening such as resealable opening 256. In the illustrated embodiment, treatment enclosure 250C can be closed via a drawstring 272, to enclose infested articles within treatment enclosure 250C. While pesticidal vapors will be released both inside and outside of treatment enclosure 250C, the concentration of pesticide impregnated within single layer 252C is sufficient to provide effective control of pests enclosed inside treatment enclosure 250C. Some embodiments such as treatment enclosure 250C may be particularly advantageous in outdoor applications, for example in the treatment of a plant infested with aphids or other pests, where there is limited concern for any odor released by the pesticidal treatment.

In some methods, the enclosed space in which pests are to be controlled is a bee hive wherein bees are infested by a parasitic pest such as *varroa* mites. In some embodiments, vapors released by a pesticidal composition, substrate, or device are effective in selectively controlling a parasitic pest without causing significant harm to its beneficial host. For example, some embodiments of the present invention can be used to control *varroa* mites within honey bee colonies by differentially killing and/or controlling the mites more readily than the bees. In some embodiments, the pesticidal vapors may disrupt or inhibit feeding, growth or reproductive functions of the *varroa* mites, or they may cause the mites to detach from the bees.

Figure 15:
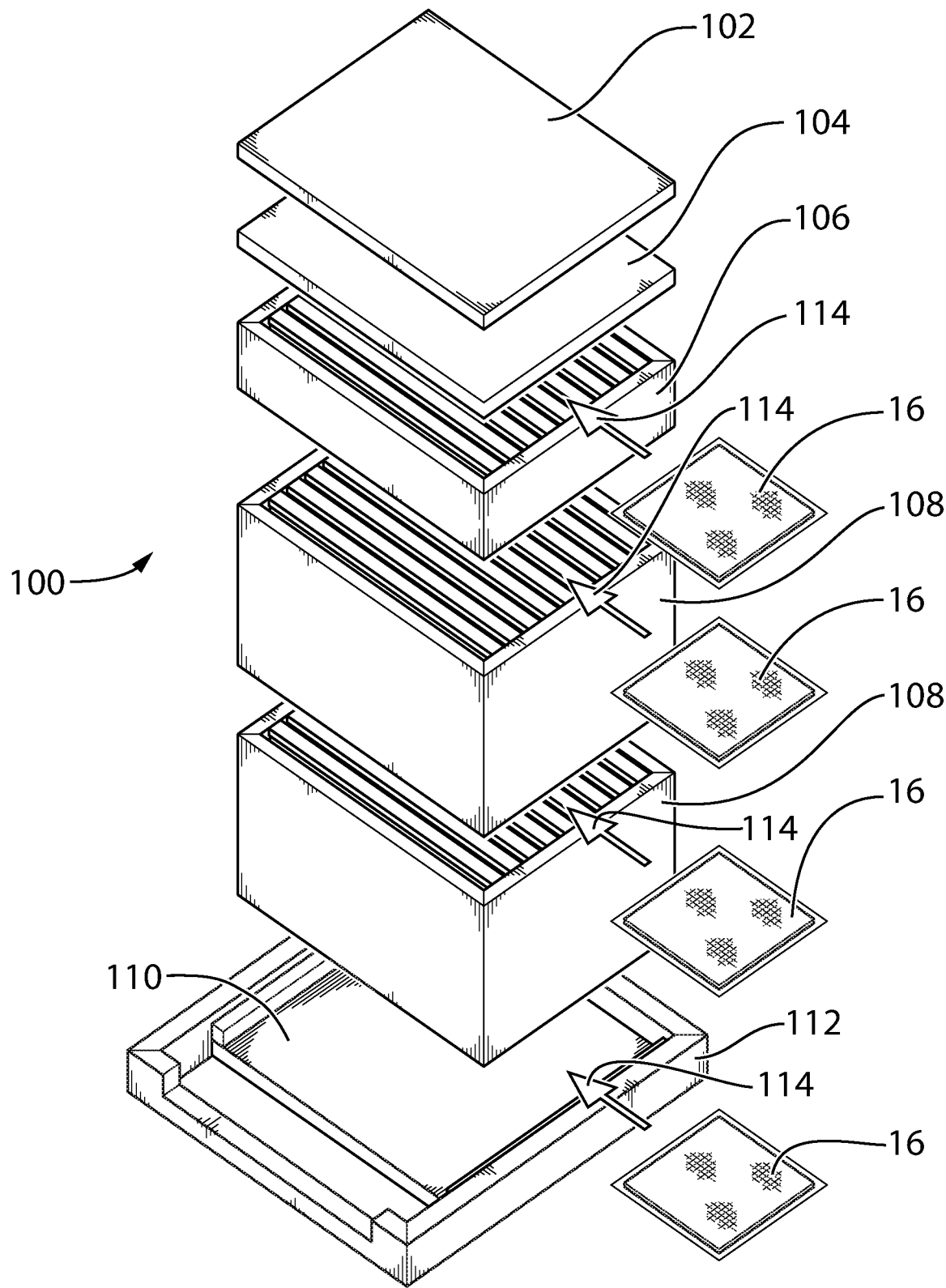
FIG. 15 shows a schematic diagram of a Langstroth bee hive that provides a treatment enclosure in one example embodiment.
Figure 16:
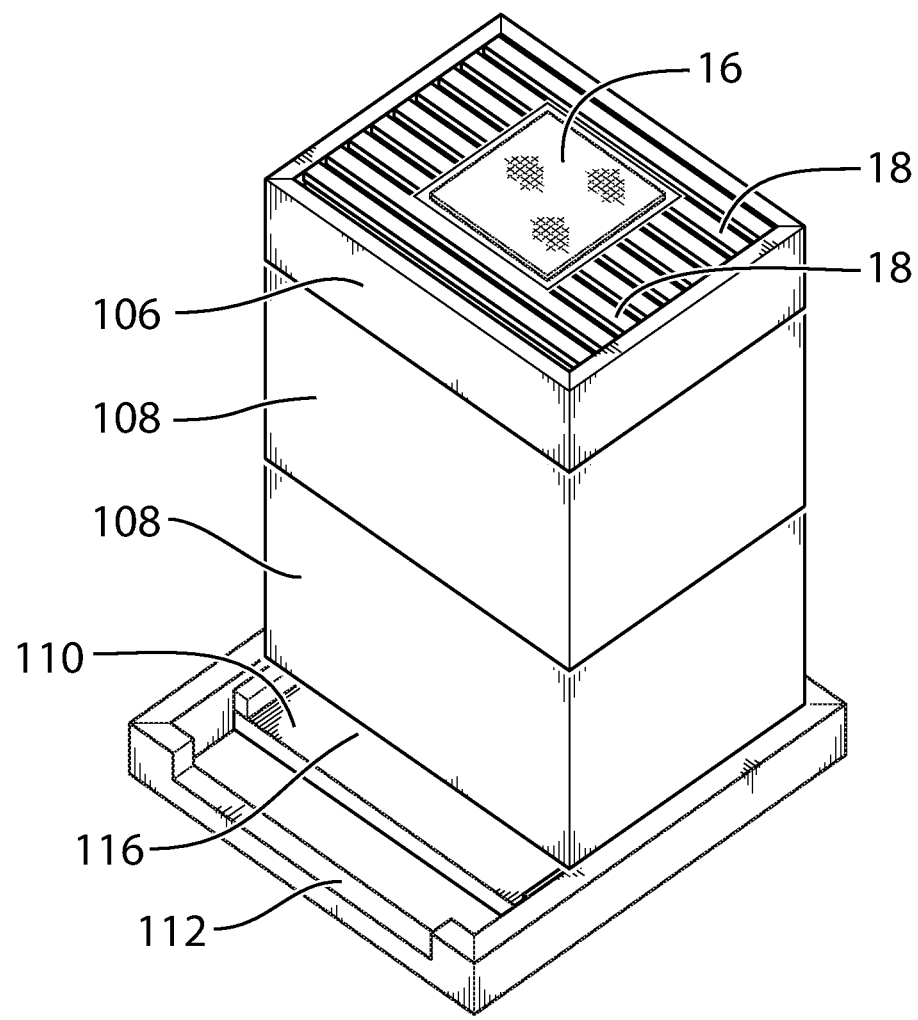
FIG. 16 shows an example placement of a generally flat substrate impregnated with a pesticidal composition on frames within a Langstroth bee hive in one example embodiment.

With reference to FIGS. 15 and 16, an example embodiment of a treatment enclosure that is a Langstroth bee hive 100 is illustrated. Bee hive 100 has an outer cover 102, an inner cover 104, a honey super 106, two vertically stacked brood chambers 108, a bottom board 110, and a hive stand 112. Arrows 114 represent potential locations where a generally flat substrate 16 impregnated with a pesticidal composition, or other device for releasing pesticidal vapors, could potentially be inserted within bee hive 100, and FIG. 16 shows an example placement of such a substrate on top of frames 118 of a honey super 106 within the hive.

Hive 100 is an example of a treatment enclosure that is at least partially permeable to pesticidal vapors. In particular, hive 100 includes openings 116 to allow bees to enter and exit hive 100. In the illustrated embodiment, opening 116 has been illustrated as being positioned at the bottom of the lower-most brood chamber of the hive (just above the ground). Such openings are typically 1-3 cm tall and can vary in width in typical hives. However, openings 116 can be provided at any desired location, for example, at the gap between or drilled into the front face of any of the brood chambers or honey super chambers. Pesticidal vapors released by substrate 16 are generally contained within hive 100, but there is some escape of pesticidal vapors from hive 100 (i.e. hive 100 is not airtight).

In some example embodiments, a vapor-release device or substrate such as any of those described above is inserted within a bee hive, and the substrate or reservoir of the release device is in fluid communication with a source of pesticidal composition, for example a hose or other form of tubing is connected at a first end to an external reservoir containing a solution of pesticidal composition, and a second end of the hose or other form of tubing is positioned to release liquid pesticidal composition onto the substrate or into the reservoir. A manual hand pump or an electrically activated pump is supplied to allow pesticidal composition to be pumped from the external reservoir onto the substrate or into the reservoir of the vapor release device. In use, an operator can periodically manually actuate the hand pump and/or the electrically activated pump can be periodically or continuously actuated to deliver a periodic or ongoing supply of pesticidal composition to the substrate or reservoir. Such an apparatus facilitates the ongoing and/or repeated delivery of pesticidal vapors within the bee hive, without the need to periodically open up the hive and replace a pesticide-impregnated substrate, which can potentially disrupt the bees within the hive. The apparatus also reduces the labor costs that would be associated with periodically manually replenishing the source of pesticidal vapors inside the hive.

In some embodiments, the volume of the container is variable such that the volume of space in the container may be reduced or expanded as desired to facilitate treatment. For example, some methods comprise placing objects in a variable-volume container with a device for releasing pesticidal vapors, removing a quantity of excess air from the variable-volume container, and sealing the container for a sufficient time to allow the vapors of the pesticidal composition to kill or control the target pests and/or its eggs. Reducing the volume of space to be treated in this way can allow for a higher vapor concentration to be achieved in the container for a given dose of pesticidal vapors, or can allow for a smaller dose to be delivered to achieve a given vapor concentration. The variable-volume container can be a bag made of flexible plastic or any other non-rigid, impermeable material.

Although reducing the volume of the treated space in this way can be beneficial, preferably sufficient space is left around the treated objects to allow for the flow of pesticidal vapors to circulate evenly throughout the space. In some embodiments, the variable-volume container includes a means for maintaining some space between the objects within the container and the walls of the container. For example, the variable-volume container may comprise an adjustable internal ribbing for supporting the walls of the container some distance away from the objects within the container.

In some embodiments, the container includes a valve through which air may be removed from the container, and/or pesticidal vapors may be added to the container. In some embodiments, air is removed through the valve by squeezing in the walls of the container. In other embodiments, air is removed using a device such as a vacuum or a pump. In some embodiments, a device for releasing pesticidal vapors is attachable to the valve such that pesticidal vapors are releasable into the sealed container.

In some methods, a pump is used to pump pesticidal vapors into a sealed container. The pump may allow the concentration of pesticidal vapors in the container to be increased more quickly and to a higher level than could be achieved by passive diffusion. Increased vapor pressure can in turn result in faster mortality of target pests and a shorter overall treatment period. In some methods, the pump is used to increase the vapor concentration in the container above a desired threshold or within a desired range. The pump may be manual, electric or otherwise motorized.

In some methods, a pump and/or valve is first used to remove air from a sealed container and then is used to add pesticidal vapors into the container. Such methods can further increase the relative concentration of pesticidal vapors in the container and reduce the availability of clean air for the target pests to breathe.

In some embodiments, a treatment container is provided that has a device for releasing pesticidal vapors built-in. The treatment container may be variable-volume as described above. The treatment container may include a valve and/or pump as described above.

Examples of objects that may be treated according to embodiments of the present invention include books, artwork, toys, clothing, linens, footwear, documents, DVDs, electronics, computers, phones, furniture, luggage, bedding, pallets, crates, lumber, firewood, soil, plants, pets, items being shipped in a shipping container, bee hives, food, food storage containers, or any other object that may be infested with a target pest. In some embodiments, such infested objects are referred to as infested articles.

In some embodiments, the effectiveness of the pesticidal vapor in controlling a target pest is enhanced by the release of a stimulation agent before, after, or at the same time as the release of the pesticidal vapors. The stimulation agent may act as stimulant or attractant to the target pest, such that the pest moves about more, moves closer to the release of pesticidal vapors and/or moves out of safe harborages into open space. The stimulation agent may act to increase the metabolic rate and/or the breathing rate of the target pest, such that its bio-uptake of pesticidal vapors is increased. The stimulation agent may otherwise serve to stimulate the target pest to be more active than it would be without the presence of the stimulation agent, thereby increasing the likelihood it will be exposed to and affected by the pesticidal vapors.

In some embodiments, the stimulation agent is carbon dioxide ($CO_2$), nitrogen ($N_2$), a propellant, or an inert gas. In other embodiments, the stimulation agent is a pheromone, kairomone, allomone, repellent, or other semiochemical, or a phagostimulant. In other embodiments, the stimulation agent is heat. In other embodiments, the stimulation agent is moisture or water vapor. In other embodiments, the stimulation agent is light, darkness, vibration or air movement. In other embodiments, the stimulation agent is color. In other embodiments, the stimulation agent is ultrasound.

In some embodiments, the volume within the treatment enclosure (which is a sealed container in some embodiments) is in the range of 10 L to 200 L and the amount of pesticidal composition used is in the range of 10 mL and 200 mL. In some embodiments, for example where the treatment enclosure is a shipping container, the treatment enclosure has a volume in the range of 300,000 to 1,000,000 L, including any value therebetween. In some embodiments, the amount of pesticidal composition used is in the range of 10 mL to 100 mL per 100 L of volume of the treatment enclosure. In one example embodiment, a treatment enclosure having a volume in the range of 100 L to 1200 L (for example, a sufficiently large volume to accommodate a king size mattress) is provided, and between about 100 mL to 1 L of pesticidal composition is provided on a pre-dosed substrate, or split among a plurality of pre-dosed substrates, for insertion into the treatment enclosure.

In some methods, the vapor concentration within the treatment enclosure (which is a sealed container in some embodiments), expressed as the percent of the amount of pesticidal composition evaporated relative to the total volume of the container, is greater than 0.01%. In some methods, the vapor concentration within the sealed container, expressed as the amount of pesticidal composition applied relative to the total volume of the container, is in the range of 0.01% to 0.2%. In some embodiments in which it is desired to control an undesirable arthropod pest while not harming a beneficial arthropod species, the vapor concentration within the sealed container, expressed as the amount of pesticidal composition applied relative to the total volume of the container, is in the range of 0.01% to 0.15%.

Some embodiments of the present invention can be used to control pests that are arthropods, including insects and arachnids, and/or other pests. Some embodiments of the present invention can be used to control sucking and biting pests, including bed bugs, mites, ticks, fleas, ants, lice, mosquitoes and cockroaches. Exemplary results are presented in this specification demonstrating the control of a number of arthropod pests using vapors of a pesticidal composition, including bed bugs, *varroa* mites, bees, cockroaches, ants, granary weevils, beetles and earwigs. Based on the similarity of terrestrial arthropods, including insects, with respect to organism size, cellular respiration, and other morphological respiratory structures, it can be soundly predicted that pesticidal compositions and devices as described herein can be used to control other terrestrial arthropod pests, including subterranean arthropod pests.

Some embodiments can be used to control pests by killing the pests, repelling the pests, preventing or reducing feeding, preventing or reducing oviposition, preventing or reducing eclosion of their eggs, or the like. Some embodiments exhibit effective pesticidal activity as a vapor. Some embodiments provide methods of killing or controlling pests comprising moistening or otherwise impregnating a substrate with the composition and placing the material in the vicinity of the pests such that they are exposed to the vapors of the composition as they are released from the substrate.

Some embodiments of the present invention provide pesticidal compositions comprising neem oil and acetophenone, in combination with any suitable diluent. In some embodiments, the diluent may be an organic or inorganic solvent. Commonly used organic liquid diluents include, but are not limited to, ethanol, isopropyl alcohol, benzene, butanol, 1-propanol, hexanol, other alcohols, glycerol, glycerides, lactic acid or dimethyl ether. Commonly used liquid inorganic diluents include, but are not limited to, water, ammonia, or sulphur dioxide.

Some embodiments can be used to control pests by killing the pests, preventing or reducing feeding, preventing or reducing oviposition, preventing or reducing eclosion of their eggs, or the like. Some embodiments exhibit effective knockdown pesticidal activity, effective residual pesticidal activity and/or effective pesticidal activity as a vapor. Some embodiments provide methods of killing or controlling pests comprising applying a pesticidal composition so that pests or their eggs may contact or otherwise be exposed to vapor of the composition. In some embodiments, pests are killed by exposure to vapors released from a substrate that has been moistened or otherwise impregnated with a pesticidal composition.

Some embodiments of the present invention pertain to compositions that can be used to control a variety of pests. Some embodiments contain a repellent or attractant to 'push' or 'pull' the pest to direct them to a treatment area or to otherwise influence pest behavior to effect better treatment. Some embodiments of the present invention can be used to control arthropods, including mites, and/or other pests. Some embodiments of the present invention can be used to selectively control a parasitic pest infecting a beneficial host. For example, some embodiments of the present invention can be used to control *varroa* mites within honey bee colonies, differentially killing mites more readily than bees.

Some embodiments of the invention pertain to methods for the control of pests such as mites. In some embodiments, the pests are differentially controlled relative to a beneficial species, i.e. a greater proportion of the pests are killed or otherwise harmed than are members of the beneficial species. In some embodiments, vapors of a pesticidal composition are used to control pests such as mites. Some embodiments include the use of a device or structure that allows the controlled release of pesticidal vapors. Some embodiments contain a repellent or attractant to influence pest movement as well as a pesticide. Some embodiments include a vapor dosage indicator. Some embodiments allow honey bee brood frames to be placed to allow the circulation of treated air.

Some embodiments of the present invention can be used to selectively control a parasitic pest infecting a beneficial host. Some embodiments exhibit effective pesticidal activity against a target pest species while not significantly harming a similarly exposed beneficial insect species. Some embodiments contain a repellent or attractant to 'push' or 'pull' the pest from hard to treat areas and direct them to a treatment area or to otherwise influence pest behavior to effect better treatment. Some embodiments can be used to control pests including arthropods such as mites. Some embodiments can be used to control *varroa* mites within honey bee colonies, differentially killing the mites at a much greater percentage (i.e. with a much higher efficacy) than the bees (i.e. killing a high percentage of mites and only a small percentage or none of the bees).

In some embodiments, a pesticidal composition is provided that can selectively control an undesirable pest while causing little or no harm to a beneficial species. In some embodiments, both the undesirable pest and the beneficial species are exposed to the pesticidal composition. In some embodiments, both the undesirable pest and the beneficial species are arthropods. In some embodiments, the undesirable pest is an arachnid that is a member of the Subclass Acari. In some embodiments, the beneficial species is an insect that is a member of the Family Apidae. In some embodiments, the undesirable pest is a mite. In some embodiments, the beneficial species is a bee or other pollinating insect. In some embodiments, the undesirable pest is a *Varroa* mite. In some embodiments, the beneficial species is a honey bee. In some embodiments, the undesirable pest has a smaller mass than the beneficial species.

Some embodiments include the use of a device or structure that allows the controlled release of pesticidal vapors. Some embodiments contain a repellent or attractant to influence pest movement as well as a pesticide. Some embodiments include a vapor dosage indicator. Some embodiments can be used to control pests including arthropods such as mites. Some embodiments can be used to control *varroa* mites within honey bee colonies, differentially killing the mites at a much greater percentage than the bees. In some embodiments, a pesticidal composition as defined herein is applied inside a honey bee colony to selectively control an undesirable pest therein, for example *varroa* mites, without significantly harming the honey bee colony. Some embodiments allow honey bee brood frames to be placed to allow the circulation of treated air. In some embodiments air circulation is optimized for a brood nest temperature of between approximately 10° C. to 35° C., including any value therebetween, e.g. 12, 14, 16, 18, 20, 22, 24, 26, 28, 30 or 32° C.

In some example embodiments where the pests to be treated are *varroa* mites and it is desired to control the *varroa* mites while not significantly adversely affecting a beneficial species, e.g. honey bees, any of the devices, methods or compositions described above are used to introduce pesticidal vapors within a hive containing honey bees. In some such embodiments, the treatment enclosure is a bee hive.

In some embodiments, the bee hive is a Langstroth, WBC (William Broughton Carr), Long-box, Dartington, Warré, Perone, Dadant, British National, or Commercial type of hive. In some embodiments, the hive is a nucleus colony box. In some embodiments, the bee hive has any number or arrangement of brood chambers or honey supers. In some embodiments, the bee hive has a plurality of brood chambers and/or honey supers contained therein. In some embodiments, the brood chambers and/or honey supers are arranged in any suitable arrangement. In some embodiments, for example as illustrated in FIG. 15, the bee hive has two vertically stacked brood chambers and one vertically stacked honey super.

In some embodiments, the bee hive provides a treatment enclosure that is permeable to pesticidal vapors. In some embodiments, the pesticidal vapors can escape through openings in the bee hive (for example, the entrances of the hive, the bottom of the hive, and air gaps between chambers). In some embodiments, some or all of the openings are partially or fully sealed to restrict the escape of pesticidal vapors from the hive. In some embodiments, such sealing is achieved by tying, taping, stapling, heat-sealing, gluing, plugging, capping, lidding, coating, or otherwise fully or partially closing the openings. In some embodiments, the bottom of the hive is fully or partially sealed by affixing a board or other generally planar object over the bottom (or a portion of the bottom) of the hive.

In some embodiments, the presence of wood, wax, honey and/or other structures within a hive decreases the concentration of pesticidal vapors within the hive, as compared with a hive that does not include the presence of such structures. Without being bound by theory, in some embodiments, the presence of wood, wax, honey and/or other structures within a hive provides a protective effect, that helps to prevent the honey bees from being harmed and/or killed by the pesticidal vapor while the pesticidal vapor retains its efficacy against a target pest such as *varroa* mites.

Some exemplary embodiments of the present invention are further described with reference to the examples below, which are intended to be illustrative and non-limiting. Embodiments of the present invention are not limited to the particular pesticidal compositions or concentrations described in the examples below. In addition to the particular concentrations set forth below, other broad ranges of concentrations of ingredients are believed to be effective as well. For example, embodiments of the present invention include pesticidal compositions comprising neem in the range of 0.2 to 40 percent by weight. Other embodiments of the present invention include pesticidal compositions comprising acetophenone in the range of 10 to 99.8 percent by weight. Embodiments of the present invention are also not limited to compositions comprising ethoxylated castor oil, isopropyl alcohol, water or any other particular surfactant, carrier, emulsifier, diluent, fragrance or other additive. Any suitable surfactant, carrier, emulsifier, diluent, fragrance or other additive could be used in alternative embodiments.

EXAMPLES

Example 1.0

Efficacy of Volatile Pesticidal Solutions Applied in an Enclosed Treatment Enclosure Example 1.1

Description of Compositions and Substrates Used

The following examples utilize three pesticidal compositions referred to as 'Solution A', 'Solution B', and 'Solution C'. 'Solution A' contained 5.5% cold pressed neem oil by weight, 18.25% acetophenone by weight, and 1.25% ethoxylated castor oil by weight and used water as a diluent (75% by weight). 'Solution B' contained 5.5% cold pressed neem oil by weight, 18.25% acetophenone by weight, and 1.25% ethoxylated castor oil by weight and used isopropyl alcohol (IPA) as a diluent (75% by weight). 'Solution C' contained 5.5% cold pressed neem oil by weight, 18.25% acetophenone by weight, 1.25% ethoxylated castor oil by weight, and 1% fragrance by weight with isopropyl alcohol (IPA) used as a diluent (74% by weight).

All experiments were conducted at a temperature of 21±2° C. unless otherwise indicated. Without being bound by theory, changes in temperature may affect the release of vapor from the pesticidal composition, so lower concentrations may be effective at higher temperatures, and higher concentrations may be required at lower ambient temperatures. Based on experiments conducted by the inventors, the compositions tested in these examples maintain efficacy at temperatures of 15° C. or higher, and can reasonably be expected to remain effective at lower temperatures, although higher treatment concentrations may be required at lower temperatures.

A variety of different substrates were tested for their ability to release pesticidal vapors. Characterization of the pore size of some of the texted substrates was performed by measuring the pore diameter of 10-20 pores per substrate using a light microscope.

The laboratory mat used in some experiments is made from flattened cotton batting, and is an example of a non-woven naturally occurring polymer that is derived from plants. Cotton is a cellulose substrate. The pore size of exemplary laboratory mat was measured to range between about 100-500 µm, with an average pore size of 260 µm. Total pad thickness was approximately 3 mm.

Commercially available cellulose pads known as Zap pads from Paper Pak Industries (product code Z-21001) were used in some experiments. These substrates have twelve layers of non-woven cellulose pressed together into a high-crepe pad open on four sides with a thick plastic backer pad, and are an example of a non-woven, naturally occurring polymer of plant origin. The pore size of exemplary pads was measured to range between about 50-100 µm, with an average pore size of 100 µm. The total pad thickness was approximately 2.2 mm.

Filter paper used as a substrate in some experiments was a single layer of pressed cellulose, and is an example of a non-woven naturally occurring polymer providing a cellulose substrate. The pore size of exemplary filter papers was measured to range between 60-1200 µm, with an average pore size of 396 µm. The total thickness of the substrate was approximately 0.2 mm.

Cotton cloth used as a substrate in some experiments is an example of woven fibers of a naturally occurring polymer, namely cotton, which is a form of cellulose. The pore size of exemplary cloth was measured to range between 20-100 µm, with an average pore size of approximately 33 µm.

Example 1.2

Efficacy of Vapors Against Bed Bugs in Petri Dish

Previous laboratory studies have demonstrated that adult bed bugs consistently exhibit 100% mortality within 24 hours when placed in contact with Solution A-treated filter papers within a sealed Petri dish. This study was designed to determine if Solution A vapors can cause bed bug mortality.

Solution A formulation (1.39% v/v) was applied evenly to each 9 cm diameter filter paper using a micro-applicator, and allowed to dry for 4 hours. 1 ml of Solution A liquid was applied inside a 72 ml Petri dish as a treatment enclosure, to yield a percentage concentration of pesticide of 1.39% (v/v, calculated as the volume of pesticide relative to the volume of the Petri dish that provided the treatment enclosure). A negative control paper was treated with water but was not exposed to Solution A. The untreated paper was placed on the bottom of a Petri dish in contact with bed bugs, and sealed with a lid (negative control). The treated paper was suspended from the top of a Petri dish out of reach of bed bugs, and sealed with a lid. Each Petri dish and paper was exposed to ten adult bed bugs (approximately half male and half female) immediately after the 4-hour drying period. The outside circumference of the Petri dishes was sealed with Parafilm™.

Bed bugs were observed for signs of toxicity, mortality and oviposition at 1, 2, 4, 6, and 24 hours after bed bugs were introduced to filter papers, then daily for 14 days. Bed bugs that were exposed to 1.39% v/v Solution A-treated paper, but prevented from contacting the paper, exhibited 100% mortality within 24 hours, indicating that toxic vapors emitted by Solution A can cause bed bug mortality, and that direct contact with treated surfaces are not necessary to induce mortality. This result is unexpected because typically pesticidal natural oils such as neem oil are effective only as contact killers (i.e. actual contact is required for pesticidal activity).

Example 1.3

Efficacy of Vapors Against Bed Bugs Eggs in Petri Dish

This study was designed to determine whether vapors of a pesticidal composition comprising neem oil and acetophenone would be effective against bed bug eggs and to assess the time period that bed bug eggs must be exposed to vapors before 100% efficacy is achieved.

Groups of five healthy bed bug eggs (each 2-day old) were each adhered to 9 cm diameter Petri dishes using a small drop of honey. Filter papers were treated with 260 ft$^2$/gal (1.39% v/v, i.e. 1 mL of Solution A in a 72 mL Petri dish, which provided a treatment enclosure) of Solution A. Filter paper is an example of a naturally occurring non-woven polymer that is an example of a cellulose substrate. A single treated filter paper was adhered to the roof of each egg-infested dish either immediately after dosing (0 hour dry time) or for 1, 5, 15, 30, 60 minutes, 4 hours, or 24 hours. Eggs were prevented from physically contacting treated filter papers, but each egg-infested dish was sealed with parafilm to ensure that treatment vapors permeated the dish. One egg infested dish served as a negative control and therefore was not exposed to Solution A vapors. Egg mortality was observed and recorded daily for 14 days (confirmation observations were performed for 20 days), until all eggs had eclosed or died.

Figure 17:
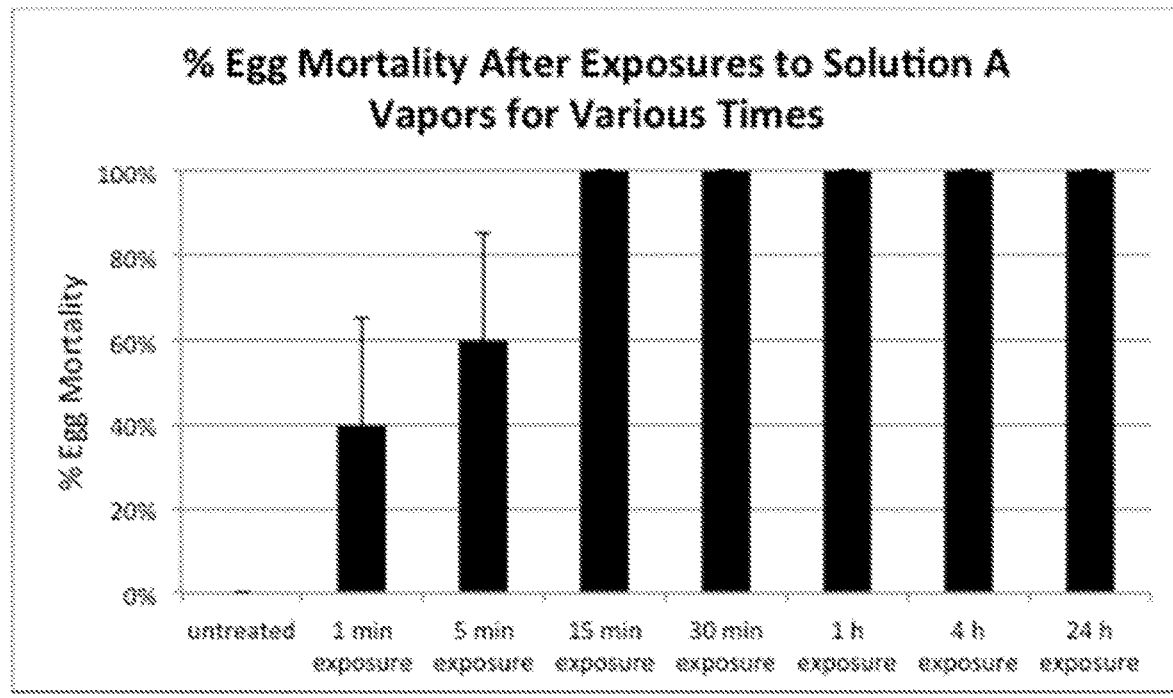
FIG. 17 shows the percent mortality of bed bug eggs exposed to vapors from filter paper treated with 260 ft$^2$/gal (1.39% (v/v)) Solution A (0 hour dry time) for 1, 5, 15, 30, 60 minutes, 4 hours, or 24 hours. Control eggs (untreated) were not exposed to Solution A vapors.

As shown in FIG. 17, bed bug eggs exposed to 1.39% v/v Solution A vapors for 1 minute or 5 minutes exhibited 40% and 60% mortality, respectively. Eggs that were exposed to 1.39% v/v Solution A vapors for 15, 30 or 60 minutes, 4 hours, or 24 hours, exhibited 100% mortality. These results suggest that within confined spaces treated with 260 ft$^2$/gal (1.39% v/v) Solution A, bed bug eggs can be controlled with Solution A vapors, and do not require direct contact with Solution A. These results also suggest that bed bug eggs should be exposed to vapors for at least 15 minutes at the tested concentration for maximum efficacy.

FIG. 17 shows percent mortality of bed bug eggs exposed to vapors from filter paper treated with 260 ft$^2$/gal (1.39% (v/v)) Solution A (0 hour dry time) for 1, 5, 15, 30, 60 minutes, 4 hours, or 24 hours. Control eggs (untreated) were not exposed to Solution A vapors.

Example 1.4

Efficacy of Vapors Against Bed Bug Eggs Under Layers of Upholstery

This study was designed to test the efficacy of Solution A against bed bug eggs in environments where eggs are typically difficult to treat (such as under fabrics, carpet, etc.). Bed bug eggs were adhered to filter paper in a Petri dish and covered with either 1, 2, or 3 pieces of upholstery fabric (each 9 cm diameter, 1.5 mm thickness). The top-most piece of fabric was sprayed with 400 ft$^2$/gal Solution A (=0.8% v/v of Solution A (0.64 mL) relative to the volume of the Petri dish (72 mL)), and the Petri dish was covered with a nylon mesh (open-air) or a plastic lid (closed-dish), and eclosion was observed for 20 days. In the case where the Petri dish is covered with a nylon mesh, the void-space is effectively closed by the upper-most layer of upholstery but there will inevitably be some leakage of vapor, thus lowering the vapor concentration slightly. In other words, the nylon mesh covered dish provides a partially permeable treatment enclosure. Two egg-infested pieces of paper were left untreated to serve as negative controls. Dead eggs were defined as those which failed to eclose after the 20 day observation period, and appeared dried or swollen when observed microscopically.

Eggs exhibited 100% mortality when covered with 1, 2, or 3 pieces of upholstery in open-air and closed-air Petri dishes.

The purpose of using an impregnated substrate or gel is to create a vapor-releasing vehicle that could be used to treat items that would be difficult to treat otherwise. Alternatively, a device for releasing pesticidal vapors from a liquid comprising a pesticidal composition can be provided to supply the vapors. For example, vapors are ideal for treating items such as electronics, art-work and books that can be damaged by direct application of a liquid spray. Vapors also have the advantage of penetrating into small and difficult to reach areas, such as cracks, crevices and cavities where insects may hide. The impregnated substrate would be placed into a sealed bag or container along with the sensitive items that require treatment.

The table below summarizes the results of multiple studies conducted to test varying substrates and gels, compositions, containers and contents.

TABLE 1

Summary of Container Studies using various Substrates

| Study | Substrate/Gel | Pesticidal Composition | Dose (mL) | Container Volume (L) | Container contents | Length of study (days) | % Mortality |
|---|---|---|---|---|---|---|---|
| 1 | Alginate (10 g) | Solution A | 30 | 17.3 | Empty | 2 | 100 |
| 2 | Alginate (20 g) | Solution A | 30 | 94.4 | Hard plastic clutter | 4 | 100 |
|  |  |  | 40 | 94.4 |  |  | 90 |
|  |  |  | 50 | 94.4 |  |  | 100 |
|  |  |  | 60 | 94.4 |  |  | 100 |
| 3 | Polyester cloth | Solution A | 72 | 94.4 | Books | 5 | 60 |
| 4 | Pine wood shavings | Solution B | 50 | 85 | Books | 17 h | 100 |
| 5 | Cotton rag | Solution B | 36 | 85 | Books | 17 h | 100 |
| 6 | Cotton rag in plastic housing | Solution B | 34 | 85 | Books | 1 | 100 |
|  |  |  |  | 85 | Books | 3 | 90 |
| 7 | Paper towel/cotton rag | Solution C | 42 | 85 | Books | 5 | 100 |
| 8 | Paper towel/cotton rag | Solution C | 36 | 85 | Electronics | 5 | 100 |
| 9 | Cotton Rag | Solution C | 3 oz. (90 mL) | 85 | Clothing | 5 | 100 |
| 10 | Cotton Rag | Solution C | 1 oz. (30 mL) | 85 | Shoes | 5 | 100 |

These results indicate that in an open- or closed-air environment (i.e. in a sealed or permeable treatment enclosure), multiple layers of upholstery do not protect bed bug eggs from 0.8% v/v Solution A vapors. Without being bound by theory, it is hypothesized that the pesticidal vapors can pass through the layers of upholstery to some extent, and further the fabric may trap the vapors within the Petri dish and enhance vapor efficacy.

Example 1.5

Efficacy of Vapors Released from Various Substrates in Sealed Containers

This series of studies was designed to assess the bio-efficacy of various substrates impregnated with a pesticidal composition comprising neem oil and acetophenone when placed inside sealed plastic bags or containers with various objects infested with bed bugs and eggs (such as books and electronics). Substrates tested included paper towels, cloth rags, pine wood shavings, and polyester cloth. Release of pesticidal vapors from alginate gels was also examined. These studies specifically examined the efficacy of the vapor-phase of the pesticidal composition, as the bed bugs and eggs were not sprayed directly or exposed to direct contact with the treated substrate.

Efficacy was tested against bed bugs and (in studies #7, 8 and 10) their eggs. In all studies, bed bugs were observed for signs of toxicity, mortality, and oviposition after the indicated time period had elapsed. Dead insects were defined as those which were unable to move after being stimulated. All studies included negative controls which exhibited 0% mortality.

Alginate is a natural gelling agent. Alginate molds in studies #1 and 2 of Table 1 were created by adding different volumes of Solution A (0.032-0.173% v/v, calculated based on the applied volume of pesticidal solution as indicated in Table 1 above and the final volume of the sealed container that provided the treatment enclosure) and water to alginate powder to achieve different concentrations. The liquid alginate solution was mixed in a glass beaker before transferring to an aluminum foil mold. Each mold was allowed one hour to set. Each treatment had ten bed bugs placed inside a 50 mL plastic tube containing a folded piece of filter paper and enclosed with a mesh top (allowing vapors to enter but preventing bed bugs from escaping). Each tube was placed in a plastic terrarium (approximately 3 cubic feet in volume).

In study #1, the terrarium was otherwise empty. In study #2, the terrarium was filled with various forms of plastic clutter. The alginate substrate was placed in the terrarium at opposite ends from the tube of bed bugs and the terrarium was closed with a fitted lid and placed inside a large non-porous plastic garbage bag that provided a treatment enclosure.

In study #3 of Table 1 (=0.076% v/v), a polyester cloth was used a substrate and the terrarium was filled with assorted books. Polyester cloth is an example of a woven synthetic polymer substrate. The terrarium was closed with a fitted lid and placed inside a large non-porous plastic garbage bag that provided a treatment enclosure.

In study #4, pine wood shavings dosed in Solution B (=0.059% v/v, calculated as volume of Solution B relative to the volume of the plastic bag that provided the treatment enclosure) were used as a substrate. Pine wood shavings are an example of a naturally occurring form of cellulose substrate, and are a non-woven polymer. The shavings were housed in a plastic container having multiple slits to allow the release of vapors. This housing was placed in a 30" by 38" clear plastic bag as a treatment enclosure filled with assorted books and a mesh-enclosed container of bed bugs. 100% mortality was observed after 17 hours.

In study #5 of Table 1, a cotton cloth dosed with 36 ml of Solution B (=0.04% v/v, calculated as the amount of solution B applied relative to the calculated final volume of the clear plastic bag that provided the treatment enclosure) was used as a substrate. Cotton is a naturally occurring polymer that is a form of cellulose substrate. The cotton cloth is a woven substrate. Bed bugs were contained in a Mason jar lid over which a nylon stocking was stretched taut and tied. This was then placed at the bottom of a 30" by 38" clear plastic bag and surrounded by ten randomly selected books. The treated cotton cloth contained in a slitted plastic housing was placed in the bag and 100% mortality was observed after 17 hours.

In study #6 of Table 1, plastic bags were filled with 35 assorted books. In one bag, a container enclosed with a stretched nylon stocking holding 10 bed bugs was placed amongst the books. In another bag, 10 bed bugs were infested directly on a book that was enclosed with a stretched nylon stocking. A cotton cloth was impregnated with Solution B (=0.04% v/v, calculated based on the volume of Solution B applied and the calculated volume of the plastic bag that provided the treatment enclosure) and placed into a custom made plastic housing having multiple slits to allow evaporating vapors to be released. Cotton is a naturally occurring polymer that is a form of cellulose substrate. The cotton cloth is an example of a woven polymer. The purpose of the housing was to prevent direct contact between the moistened cloth and the objects to be treated. The cloth in its plastic housing was then placed in each bag, and 100% mortality was observed in less than 24 hours for bed bugs in the nylon enclosed container, while the nylon enclosed book achieved 90% mortality in 3 days.

In study #7 of Table 1, books were infested with adult bed bugs and their eggs and placed inside large plastic storage bags. In one bag a cotton rag substrate was tested, and in another bag a paper towel substrate was tested. Cotton and paper towel are both examples of naturally occurring polymers that are different forms of cellulose substrates. The cotton cloth is a woven polymer and the paper towel is a non-woven polymer. Books were infested by encasing them in a stretched nylon stocking along with 10 live bed bugs and a piece of filter paper to which eggs were affixed. The infested books were then placed inside a 31"×42" clear plastic bag as a treatment enclosure along with 35 other books of random shapes and sizes. The cotton rag or paper towels (~7 sheets) were treated with 35 g of Solution B (=0.049% v/v, calculated as the volume of Solution B applied relative to the calculated volume of the plastic bag that provided the treatment enclosure) and placed on top of the books and the bag was sealed for 5 days. 100% adult and egg mortality was observed for both the paper towel and cotton rag substrates.

In study #8 of Table 1, a computer was infested with adult bed bugs and their eggs and placed in a bag with a keyboard and desktop telephone. Both cotton rag and paper towel substrates were tested. Cotton and paper are both examples of naturally occurring polymers that are different types of cellulose substrates. The cotton rag is a woven polymer and the paper towel is a non-woven polymer. Bed bugs were placed in a housing consisting of nylon stocking stretched taut over the ring of a Mason jar lid or a piece of cardboard of a similar size. A similar housing containing filter paper mounted with eggs was placed within a Mason jar lid ring inside a stretched nylon stocking. The computer housing was removed and the bed bug and egg samples were placed within the computer. The cotton rag or paper towel was treated with Solution B (=0.042% v/v, calculated as volume of Solution B applied relative to the calculated volume of the bag that provided the treatment enclosure) and placed on top of the electronics and the bag that provided the treatment enclosure was sealed for 5 days. Both paper towel and cotton rag had 100% mortality on both adult bed bugs and their eggs In study #9 of Table 1, articles of clothing were infested with bed bugs and place in a sealed bag. Three cotton rags were treated each with one ounce (30 mL) of Solution B. Cotton is a naturally occurring polymer that is an example of a cellulose substrate, and the cotton rags are an example of a woven polymer. One rag was placed at the bottom, middle and top of the clothing in the bag that provided a treatment enclosure (concentration of Solution B=0.105% v/v, calculated as the volume of Solution B applied relative to the calculated volume of the bag that provided the treatment enclosure). Seven articles of clothing were place in the bag in total, four of which were infested with bed bugs. 100% mortality was observed after 5 days.

In study #10 of Table 1, ten pairs of footwear were placed in a bag, five of which were infested with adult bed bugs and eggs. A cotton rag was treated with one ounce (30 mL) of Solution B and placed on top of the footwear inside the sealed plastic bag as a treatment enclosure (concentration of Solution B=0.035% v/v, calculated as the volume of Solution B applied relative to the calculated volume of the bag that provided the treatment enclosure). Cotton is a naturally occurring polymer that is an example of a cellulose substrate, and the cotton rag is an example of a woven polymer. 100% mortality was observed after 5 days.

The pesticide concentration to which the bed bugs and eggs were exposed in these studies may be estimated based on the volume of the treatment enclosure and the initial dose of pesticidal solution. In Table 2 below, vapor concentrations for each of the ten studies above are expressed as the percent of the amount of pesticidal composition relative to the total volume of the container. Note that for the studies using plastic bags, the volume of space inside the sealed bags was estimated to be approximately 3 cubic feet (approximately 85 L) based on the proportions of the bag, although an exact volume was not measured. Also note that the volumes shown in the table below do not take into account the volume of the contents of the container, and hence reflect the entire space enclosed within the container rather than the actual volume of remaining air space (i.e. void space).

TABLE 2

Summary of Vapor Concentrations

| Study # | Container Type | Container Contents | Container Volume (L) | Dose (ml) | Pesticide Concentration (% pesticidal solution/treatment volume) |
|---|---|---|---|---|---|
| 1 | Terrarium | Empty | 17.3 | 30 | 0.173% |
| 2 | Terrarium | Hard plastic clutter | 94.4 | 30 | 0.032% |
|   |           |                      | 94.4 | 40 | 0.042% |
|   |           |                      | 94.4 | 50 | 0.053% |
|   |           |                      | 94.4 | 60 | 0.064% |
| 3 | Terrarium | Books | 94.4 | 72 | 0.076% |
| 4 | Plastic Bag | Books | 85 | 50 | 0.059% |
| 5 | Plastic Bag | Books | 85 | 36 | 0.042% |
| 6 | Plastic Bag | Books | 85 | 34 | 0.040% |
|   |           | Books | 85 | 34 | 0.040% |
| 7 | Plastic Bag | Books | 85 | 42 | 0.049% |
| 8 | Plastic Bag | Electronics | 85 | 36 | 0.042% |
| 9 | Plastic Bag | Clothing | 85 | 89 | 0.105% |
| 10 | Plastic Bag | Shoes | 85 | 30 | 0.035% |

Example 1.6

Dose Response of Solution C Vapors on Bed Bug-Infested Books Sealed Inside Bags

Groups of 10 adult bed bugs and 5 bed bug eggs were each sealed into gas permeable, nylon mesh cages and placed inside or amongst items inside a plastic garbage bag (42 gallon, approximately 158 L) as a treatment enclosure. Each garbage bag (n=5 bags/treatment) contained bed bug adults and eggs, along with 50 assorted soft and hard cover books. Each bug infested bag (filled with materials) received 1-2 perforated polyethylene housings containing absorbent cellulose substrate that was dosed with 2 ounces (60 mL) of Solution C, or absorbent cellulose substrate (Zap pad) dosed with 2 ounces (60 mL) of water (untreated control). The absorbent substrate and housing was placed on top of the materials within each bag, out of physical contact with the bed bugs or eggs. The bags were then sealed and 0.037-0.074% (v/v) Solution C (calculated as the volume of Solution C applied relative to the volume of the garbage bag that provided the treatment enclosure) was allowed to evaporate over 5 days, at 20-22° C. The bags were then opened and adult bed bug mortality was observed. The mass of Solution C remaining on the absorbent substrate (compared to its initial mass) was also measured. Eclosion of treated bed bug eggs was observed daily for 14 days after removal from the bag, or until control eggs had all hatched.

Figure 18:
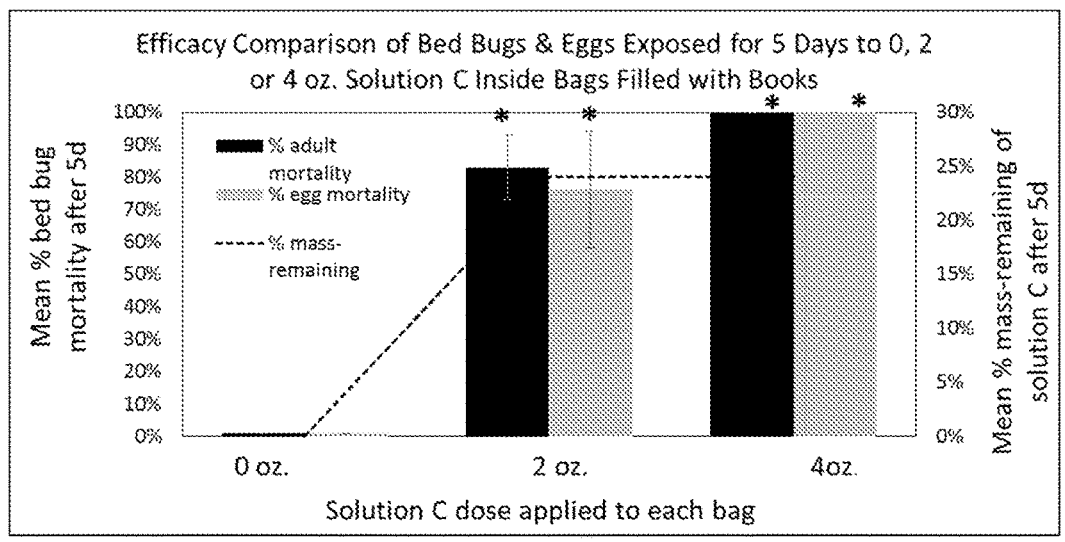
FIG. 18 shows the percent mortality of bed bug adults and eggs after exposure to 0.037% or 0.074% v/v Solution C vapors inside sealed 158 L (42 gallon) garbage bags filled with hard-cover and soft-cover books (mass-remaining of Solution C after 5 day exposure is also shown).

Vapors emitted from 4 ounces (120 mL) (0.074% v/v) of Solution C killed 100% of adult bed bugs and bed bug eggs in bags filled with books, vapors emitted from 2 ounces (60 mL) (0.038% v/v) of Solution C killed 83% of adults and 76% of eggs in bags filled with books over five days (FIG. 18). These results indicate that bed bug and egg mortality increases with the concentration of evaporated Solution C vapors inside the bag that provides the treatment enclosure.

FIG. 18 shows the percent mortality of bed bug adults and eggs after exposure to Solution C vapors inside sealed 158 L (42 gallon) garbage bags filled with hard-cover and soft-cover books (mass-remaining of Solution C after 5 day exposure is also shown). Bugs and eggs were exposed for 5 days to vapors emitted from 2 ounces (60 mL) (0.037% v/v) or 4 ounces (120 mL) (0.074% v/v) of liquid Solution C applied to absorbent cellulose pads (Zap pads) as a substrate (10 adults and 5 eggs per bag; n=5 bags per treatment, 3-4 bags per control). Lines above bars indicate standard error of adult and egg mortality; asterisks above bars indicate treatment mortality that is significantly higher than control mortality (Chi-square test; *$p<0.05$; 1 d.f.).

Example 1.7

Efficacy of Solution C Vapors on Bed Bugs Sealed Inside Bags with Different Types of Material Groups of 10 adult bed bugs and 5 bed bug eggs were each sealed into gas permeable, nylon mesh cages and placed inside or amongst items inside a 158 L (42 gallon) plastic garbage bag as a treatment enclosure. Each garbage bag (n=5 bags/treatment) contained bed bug adults and eggs mixed with the following materials: a) 50 assorted soft and hard cover books; b) one large electronic device (printer, computer, DVD or VHS player) and a mix of telephones, other small electronic items as well as DVD's, CD's and VHS tapes; c) eight pairs of shoes and three handbags; d) 20 items of clothing comprised of various different fabrics. Each bug-infested bag (filled with materials) received 1 perforated polyethylene housing containing absorbent cellulose substrate that was dosed with 2 ounces (60 mL) of Solution C(=0.037% v/v, calculated as the amount of Solution C applied relative to the 158 L (42 gallon) volume of the garbage bag that provided the treatment enclosure), or absorbent cellulose substrate (Zap pad) dosed with 2 ounces (60 mL) of water (untreated control). The absorbent substrate and housing was placed on top of the materials within each bag, out of contact with the bed bugs or eggs. The bags were then sealed and Solution C vapor was allowed to evaporate over 5 days, at 20-22° C. The bags were then opened and adult bed bug mortality was observed. The mass of Solution C remaining on the absorbent substrate (compared to its initial mass) was also measured. Eclosion of treated bed bug eggs was observed daily for 14 days after removal from the bag, or until control eggs had all hatched.

Figure 19:
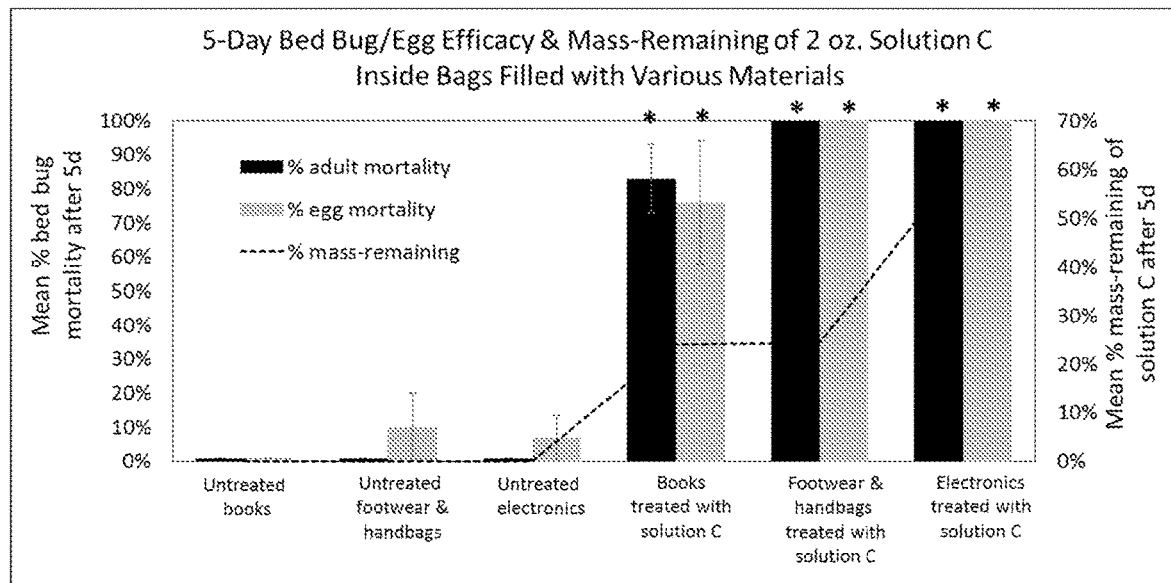
FIG. 19 shows the percent mortality of bed bug adults and eggs after exposure to 0.037% v/v Solution C vapors inside sealed 158 L (42 gallon) garbage bags filled with hard-cover and soft-cover books, footwear & handbags, or electronics (mass-remaining of Solution C after 5 day exposure is also shown).

Vapors emitted from 2 ounces (60 mL) of Solution C(=0.037% v/v) killed 100% of adult bed bugs and bed bug eggs in bags filled with electronics or footwear and handbags, and killed 83% of adults and 76% of eggs inside bags filled with books (FIG. 19). The presence of books, footwear or handbags inside the sealed bag resulted in a lower mass of Solution C remaining on absorbent cellulose pads (Zap pads) compared to the mass remaining when less absorbent materials such as electronics were placed inside the bag. This increased mass loss may derive from the books, footwear or handbag's ability to absorb Solution C vapors from the void space. The resulting lowered concentration of Solution C vapors in the void space results in lower adult and egg mortality when vapor-absorbing items are placed inside the bag. In comparison, non-absorbent items such as electronics do not lower the vapor concentration (and resulting efficacy) as readily.

FIG. 19 shows the percent mortality of bed bug adults and eggs after exposure to 0.037% v/v Solution C vapors inside sealed 158 L (42 gallon) garbage bags filled with hard-cover and soft-cover books, footwear & handbags, or electronics (mass-remaining of Solution C after 5 day exposure is also shown). Bugs and eggs were exposed for 5 days to vapors emitted from 2 ounces (60 mL) of liquid Solution C applied to absorbent cellulose pads (Zap pads) (0.037% v/v; 10 adults and 5 eggs per bag; n=5 bags per treatment, 3-4 bags per control). Lines above and below bars indicate standard error of adult and egg mortality; Asterisks above bars

Example 1.8

Figure 20:
FIG. 20 is a photograph illustrating how the absorbent pad was draped over the suit (left image) and how the suit and pad were sealed inside a suit bag (right image).

Efficacy of Solution C Vapors on a Bed Bug-Infested Suit Inside a Sealed Suit Bag Six groups of 5 healthy adult bed bugs were each encased in a gas-permeable nylon mesh-covered ring which were each placed in a different location in and around a man's suit (at the top of the suit bag, under pants on the hanger, outside of the breast pocket, inside the jacket's internal pocket, outside the lower pocket, and at the bottom of suit bag. Thirty ml (=0.043% v/v) or 60 ml (=0.086% v/v) of Solution C (calculated as volume of Solution C applied relative to the suit bag that provided the treatment enclosure) was poured onto an absorbent polymer pad (15×6 inches$^2$) (38×15 cm$^2$) adhered to a liquid-impermeable polypropylene backing (the absorbent polymer pad was cotton, a naturally occurring polymer that is a form of cellulose, that is a portion of absorbent laboratory spill matting, which is a non-woven substrate). The absorbent pad was draped over a wire coat hanger (backing-side-down), over the shoulders of the suit jacket, out of physical contact with bed bugs (FIG. 20). A sealable, gas-impervious polymer suit bag having a volume of approximately 70 L was then placed over the suit to contain the vapors and suit within for 24 hours. An additional group of 5 adult bugs remained untreated, within a gas-permeable cage placed outside of the sealed suit bag. FIG. 20 is a photograph illustrating how the absorbent pad was draped over the suit (left image) and how the suit and pad were sealed inside a suit bag (right image).

Figure 21:
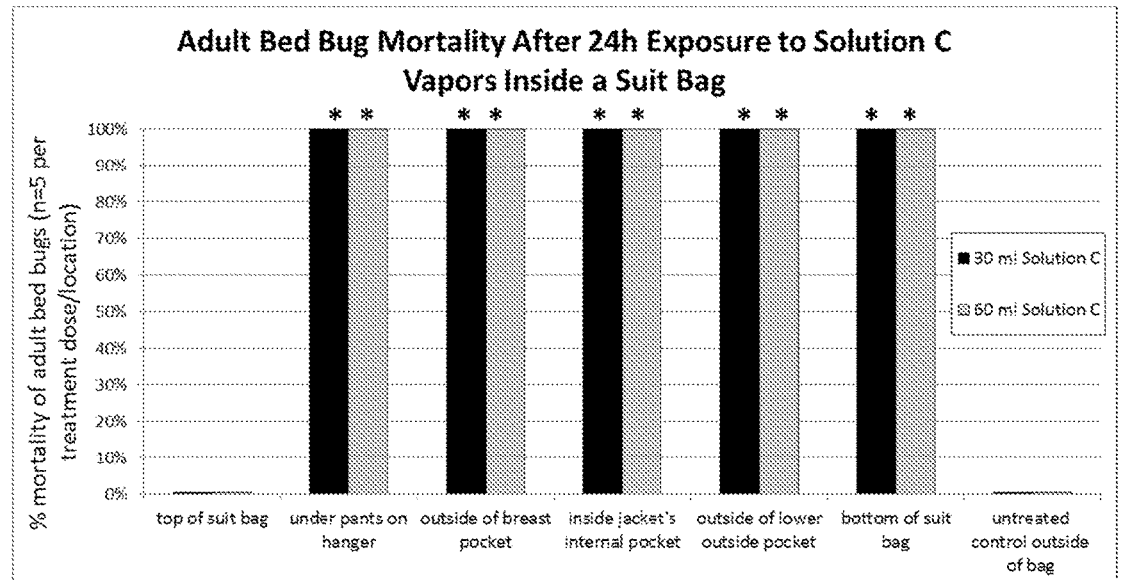
FIG. 21 shows the percent mortality of adult bed bugs exposed to vapors emitted from 30 ml (=0.043% v/v) or 60 ml (=0.086% v/v) of liquid Solution C for 24 hours inside a sealed suit-bag.

0.043%-0.086% v/v Solution C vapors emitted from an absorbent substrate inside a sealed suit-bag successfully killed 100% of adult bed bugs (all significantly higher than untreated control mortality) in all locations within the sealed suit bag except for those located at the very top of the bag (FIG. 21). Solution C vapors are denser than air, therefore, those bugs at the extreme top of the bag were likely exposed to a lower concentration of vapors than bugs at lower locations, where vapors should tend to accumulate. Active movement of vapors within the bag, changing the orientation of the bag (e.g. laying the bag flat), using a lower density formulation, or longer vapor-exposure time would likely kill 100% of all life stages of insects and other arthropods, even in the uppermost locations.

FIG. 21 shows the percent mortality of adult bed bugs exposed to vapors emitted from 30 ml (=0.043% v/v) or 60 ml (=0.086% v/v) of liquid Solution C for 24 hours inside a sealed suit-bag. The sealed suit bag contained a man's suit jacket and pants, along with gas-permeable cages containing adult bed bugs which were placed in various locations within the suit bag (n=5 bugs/treatment location). An additional group of 5 adult bugs remained untreated, within a gas-permeable cage placed outside of the sealed suit bag. Asterisks above bars indicate treatment mortality that is significantly higher than control mortality (Chi-square test; *p<0.05; 1 d.f.).

Example 1.9

Efficacy of Solution C Vapor on a Bed Bug-Infested Suitcase Sealed within a Plastic Bag Suitcases (7.8 ft$^2$) were each infested with 20 adult bed bugs and 10 bed bug eggs (10 adults and 5 eggs placed inside the suitcase, and 10 adults and 5 eggs placed on the outer wall and pockets of the suitcase). Bed bug-infested suitcases (unzipped) were each placed inside a sealed 158 L (42 gallon) garbage bag as a treatment enclosure, along with 2 absorbent cellulose pads (Zap pads), placed out of physical contact with bed bugs inside the suitcase; one pad was dosed with 30 ml of Solution C and placed on the inside of the suitcase (on the bottom when the suitcase is standing upright), and a second pad was dosed with 30 ml of Solution C and placed on top of the upright suitcase (=0.037% v/v applied per bag, calculated as the volume of Solution C applied relative to the volume of the garbage bag that provided the treatment enclosure). Three bed bug-infested suitcases were not exposed directly or indirectly to any treatment, to act as untreated controls. Adult bed bugs were observed for mortality 5 days after initial treatment to Solution C liquid or vapors. Eclosion of treated bed bug eggs was observed daily for 14 days after removal from the bag, or until control eggs had all hatched. Results are summarized in Table 3.

After 5 days exposure to 0.037% v/v Solution C vapor, all bed bug adults on the inside and outside of the suitcases were killed (compared to 10.6% average mortality of untreated control adults). Similarly, after 5 days exposure to Solution C vapors, all bed bug eggs on the outside of the suitcases were killed (compared to 7% mortality on the outside of untreated control suitcases). Egg mortality inside suitcases could not be determined. It was observed that bed bug adults had laid eggs on the control suitcases but not on the treatment suitcases, suggesting Solution C liquid or vapors prevent oviposition by causing rapid death of the adult bed bugs. These results indicate that 0.037% v/v Solution C vapors are capable of killing bed bug eggs laid on suitcases and by killing adults inside and outside of suitcases, oviposition can be prevented.

TABLE 3

Percent mortality of adult bed bugs and bed bug eggs infesting suitcases and exposed to 0.038% v/v Solution C vapors inside sealed plastic bags for 5 days (n = 20 adult bed bugs and 10 bed bug eggs/suitcase).

| Suitcase | % Adult Mortality Inside and Outside of the Suitcase | % Eclosion on Outside of the Suitcase |
| --- | --- | --- |
| 1 (untreated) | 12% | 100% |
| 2 (untreated) | 15% | 100% |
| 3 (untreated) | 5% | 80% |
| 1 (treated) | 100% | 0% |
| 2 (treated) | 100% | 0% |
| 3 (treated) | 93%** | 0% |

**One bed bug was moribund and died one week after initial observations

Example 1.10

Efficacy of Solution C Vapor Against Various Insect Pests Inside a Sealed Plastic Bag Groups of 5 healthy, adult German cockroaches (*Blattella germanica*), pavement ants (*Tetramorium caespitum*), granary weevils (*Sitophilus granarius*), Dermestid beetle larvae (*Dermestes maculatus*) or earwigs (*Forficula auricularia*) were each caged inside a gas-permeable nylon-mesh cage. Each cage was placed inside an empty, transparent plastic garbage bag (158 L, 3 mil thickness) as a treatment enclosure along with 1 polyethylene housing containing a pair of stacked absorbent cellulose pads (Zap pads, each 15.5×11 cm) dosed with 2 ounces (60 mL) of Solution C(=0.037% v/v, calculated as volume of Solution C applied relative to the volume of the treatment enclosure), or with 2 ounces (60 mL) of water (to serve as an untreated control). Solution C treated pads were placed out of physical contact with insects inside each bag. All insects were exposed to vapors inside sealed bags for 5 days, during which time they were observed for mortality. Four replications (5 insects of each species per bag) were performed for each treatment.

Insects were observed for signs of toxicity and mortality at 0, 1, 2, 3, 4 and 24 hours after initial exposure to treatment vapors, then daily for 5 days thereafter. Dead insects were defined as those which did not move and were unable to move when the bag was gently agitated. The percent mortality observed after 24 hour exposure to treatment vapors was compared to mortality of untreated control insects using Chi-square analysis.

Figure 22:
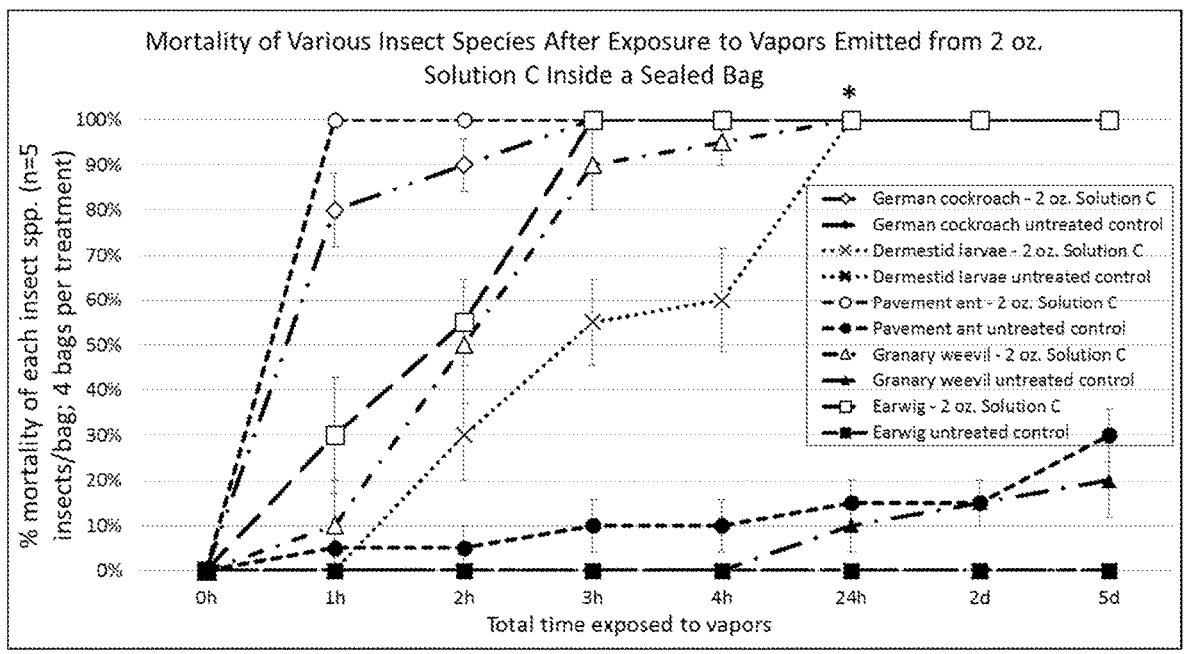
FIG. 22 shows the mortality of German cockroaches, Dermestid beetle larvae, pavement ants, granary weevils and earwigs after exposure to vapors emitted by 60 ml Solution C (=0.037% v/v) inside a sealed plastic bag (n=20 insects of each species per treatment, 5 insects per bag).

All insect species exhibited 100% mortality after 24 hours of exposure to vapors emitted by 60 ml (2 ounces) of Solution C(=0.037% v/v) inside an empty sealed plastic bag. Pavement ants were the most susceptible to vapors, exhibiting 100% mortality 1 hour after initial exposure to vapors; German cockroaches and earwigs exhibited 100% mortality 3 hours after initial exposure to vapors, and granary weevils and Dermestid beetle larvae exhibited 100% mortality 24 hours after initial exposure to vapors. Mortality of each insect species was significantly higher than control mortality (FIG. 22). These results indicate that Solution C vapors are capable of killing multiple insect species from a variety of taxonomic orders. Based on the similarity of other arthropods to insects with respect to organism size, cellular respiration and other morphological respiratory structures, it can be soundly predicted that Solution C vapors would similarly be capable of killing other species of terrestrial arthropods, including subterranean arthropods.

FIG. 22 shows the mortality of German cockroaches, Dermestid beetle larvae, pavement ants, granary weevils and earwigs after exposure to vapors emitted by 60 ml Solution C(=0.038% v/v) inside a sealed plastic bag (n=20 insects of each species per treatment, 5 insects per bag). Mortality observations were made at 0, 1, 2, 3, 4, and 24 hours after initial exposure to vapors, then daily for 5 days. Lines above and below data points indicate standard error mortality and asterisks indicate insect mortality after 24 hours vapor-exposure that is significantly higher than control mortality of the same species. (Chi-square test; *p<0.01; 1 d.f.).

Example 1.11

Measure of Vapor Concentration, Release-Rate and Corresponding Bed Bug Mortality for Volatile Components of Solution C 0.25, 0.5, 1, 2, or 4 ounces (7.5, 15, 30, 60, or 120 mL) (=0.0046%, 0.009%, 0.019%, 0.037% and 0.07% v/v relative to treatment enclosure volume) of Solution C was applied to a single- or stacked pair of absorbent cellulose pads (Zap pads, each 15.5×11 cm), contained within a perforated polyethylene housing. Each absorbent pad and housing was then sealed inside a 158 L (42 gallon) plastic garbage bag as a treatment enclosure that remained empty, or was filled with 50 assorted soft and hard cover books. Pads dosed with treatment liquid were placed on top of the books in book-filled bags.

Dosed pads were allowed to evaporate inside sealed bags at 19-21° C. for 5 days. The head space from the inflated bags was sampled at 0.5, 1, 1.5, 2, 2.5, 3, 4 and 24 hours after Solution C absorbent pads were initially placed into each bag. Sampling was performed by piercing the bottom of the bag and drawing 100 µL of head space gas using a gastight syringe. The piercing was then re-sealed with tape. Each head-space vapor sample was injected into a gas chromatograph equipped with a flame ionization detector (GC-FID: HP 6850; column: Varian CP-Wax 52CB. 24 m×320 µm×1.20 µm; injector temperature: 250° C.; detector temperature: 250° C.; oven temperature program: 60° C.>250° C. at 20° C./min.>hold 1 minute.). Head space samples were analyzed for isopropyl alcohol vapor concentration as determined by peak areas. Three replicates were performed for each Solution C concentration tested.

Isopropyl alcohol was selected for gas-chromatographic detection because it is the most abundant compound in the tested Solution C, and is therefore easier to observe via gas chromatography. The concentration of isopropyl alcohol is correlated to the volume of liquid formulation placed inside the treatment enclosure, and the isopropyl alcohol concentration, and the concentration of other formulation vapors, are greatly influenced by the presence of absorptive materials within the container. Thus, monitoring isopropyl alcohol concentration allows an assessment of the impact of the presence of absorptive materials within the treatment enclosure on the pesticidal vapor concentration therein.

In parallel, groups of 5 adult bed bugs and 5 bed bug eggs (caged inside gas-permeable nylon mesh) were each sealed into a 158 L (42 gallon) plastic bag as a treatment enclosure along with either 0, 0.25, 0.5, 1, 2, or 4 ounces (0, 7.5, 15, 30, 60, 120 mL) of Solution C(=0.0%, 0.0046%, 0.009%, 0.019%, 0.037% and 0.07% v/v) applied to absorbent cellulose pads (Zap pads contained with a perforated polyethylene housing). Pads were placed out of physical contact with adult bugs or eggs. Three treatment replicates were performed for each volume of Solution C that was tested. After 5 days exposure to Solution C, a head-space sample was drawn from each bag and analyzed for isopropyl vapor concentration (method described above). At the same time, adult bed bugs and eggs were removed from each bag and assessed for mortality. Adult mortality was defined as bugs which did not move and which did not cling to the mesh cage after light agitation; egg mortality was defined as eggs that did not eclose 14 days after initial placement within the bag. Eclosion and survival of treated bed bugs and eggs was compared to that of untreated controls using Chi-square analysis.

Figure 23:
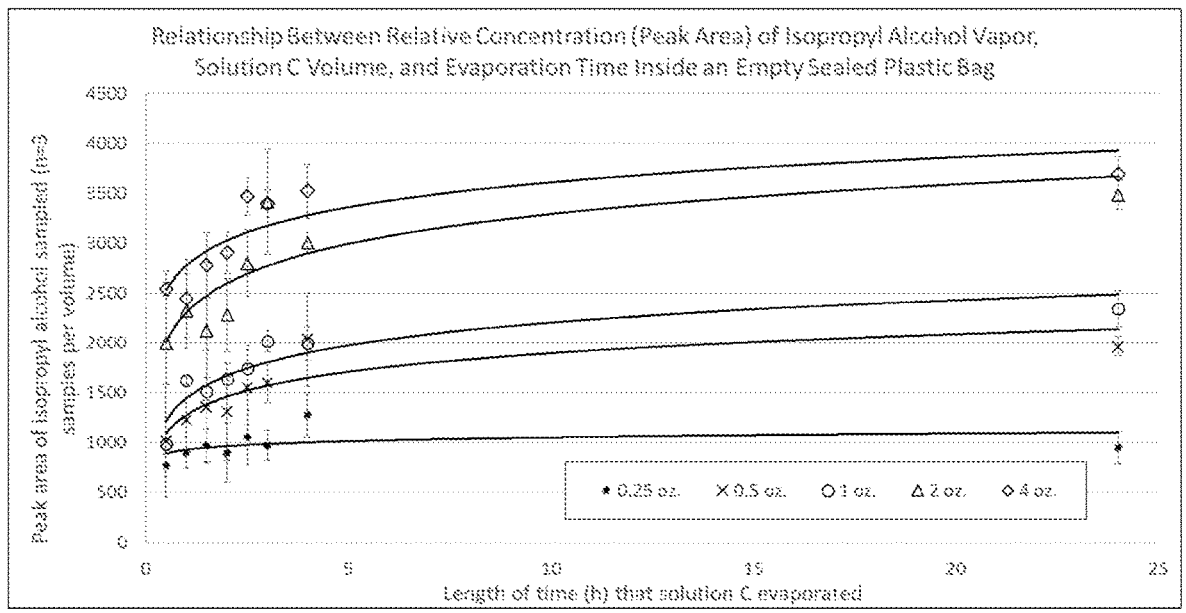
FIG. 23 shows the relative isopropyl alcohol vapor concentration (as determined by peak area) when 0.25, 0.5, 1, 2, or 4 ounces (7.5, 15, 30, 60 or 120 mL) (=0.0046%, 0.009%, 0.019%, 0.037% and 0.07% v/v) of Solution C is poured onto an absorbent cellulose pad and sealed inside an empty 158 L (42 gallon) plastic bag (n=3 bags per volume of Solution C tested).
Figure 24:
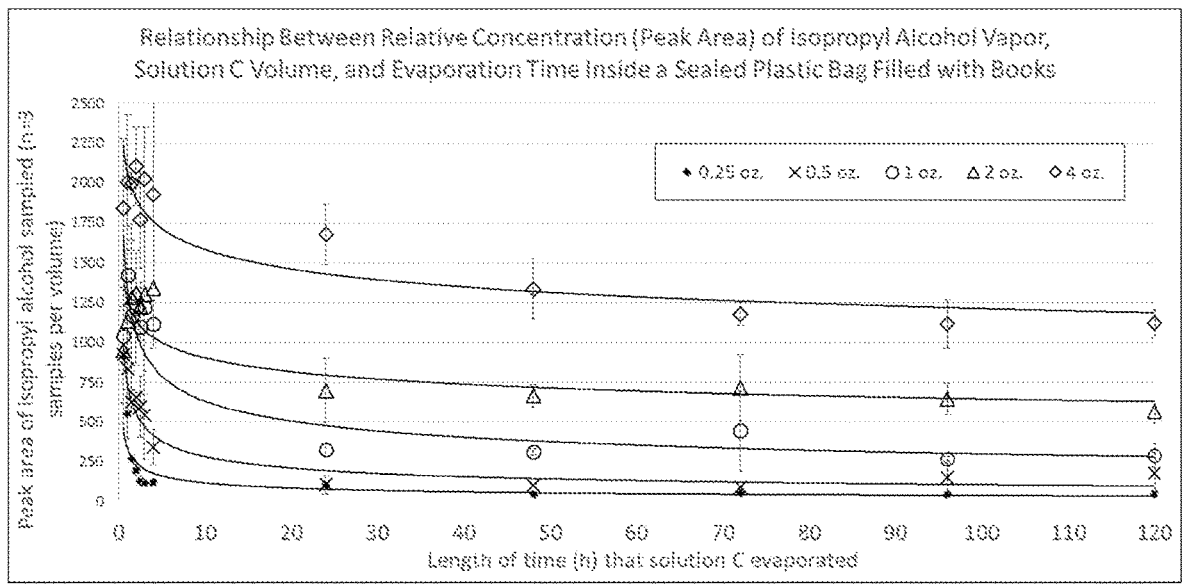
FIG. 24 shows relative isopropyl alcohol vapor concentration (as determined by peak area) when 0.25, 0.5, 1, 2, or 4 ounces (7.5, 15, 30, 60 or 120 mL) (=0.0046%, 0.009%, 0.019%, 0.037% and 0.07% v/v) of Solution C is poured onto an absorbent cellulose pad and sealed inside a 158 liter plastic bag filled with books (n=3 bags per volume of Solution C tested).
Figure 25:
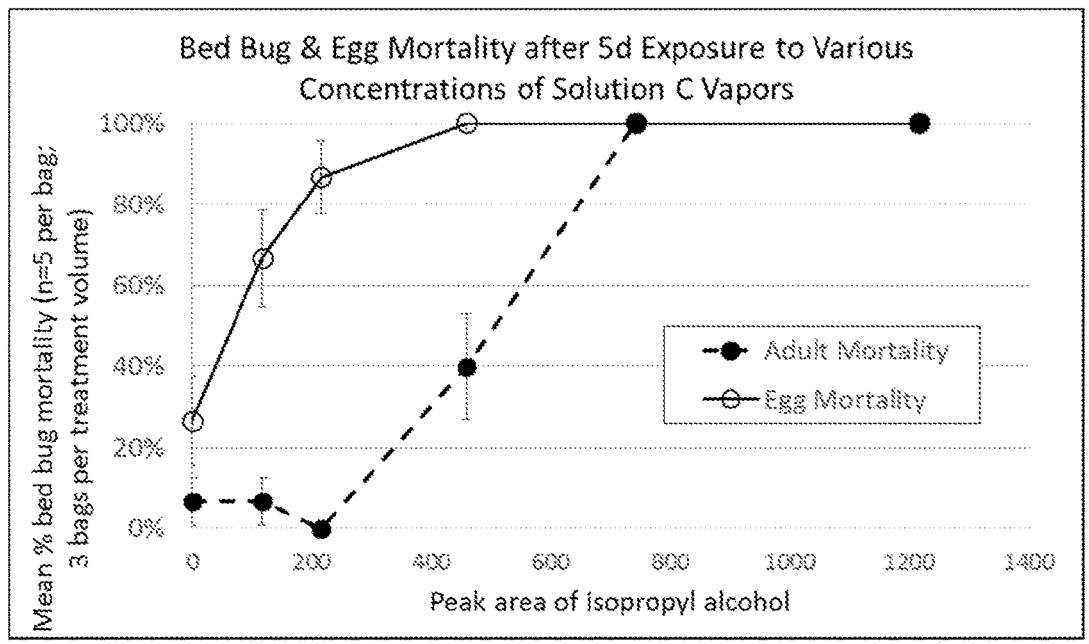
FIG. 25 shows mean mortality of adult bed bugs and bed bug eggs after 5-day exposure to various vapor concentrations emitted by 0.25, 0.5, 1, 2, or 4 ounces (7.5, 15, 30, 60 or 120 mL) (=0.0046%, 0.009%, 0.019%, 0.037% and 0.07% v/v) of Solution C inside a sealed 158 L (42 gallon) plastic bag (n=5 bugs per bag; 3 bags per concentration tested). Solution C vapor concentrations are displayed as relative isopropyl alcohol vapor concentration (determined by HPLC peak areas analyzed from samples of each bag's head-space). Lines above and below data points indicate standard error of mortality of adult bugs and eggs.

FIG. 23 shows the relative isopropyl alcohol vapor concentration (as determined by peak area) when 0.25, 0.5, 1, 2, or 4 ounces (7.5, 15, 30, 60 or 120 mL) (=0.0046%, 0.009%, 0.019%, 0.037% and 0.07% v/v) of Solution C is poured onto an absorbent cellulose pad and sealed inside an empty 158 L (42 gallon) plastic bag (n=3 bags per volume of Solution C tested). Lines above and below data points indicate standard deviation peak area. FIG. 24 shows relative isopropyl alcohol vapor concentration (as determined by peak area) when 0.25, 0.5, 1, 2, or 4 ounces (7.5, 15, 30, 60 or 120 mL) (=0.0046%, 0.009%, 0.019%, 0.037% and 0.07% v/v) of Solution C is poured onto an absorbent cellulose pad and sealed inside a 158 L (42 gallon) plastic bag filled with books (n=3 bags per volume of Solution C tested). Lines above and below data points indicate standard deviation peak area. FIG. 25 shows mean mortality of adult bed bugs and bed bug eggs after 5-day exposure to various vapor concentrations emitted by 0.25, 0.5, 1, 2, or 4 ounces (7.5, 15, 30, 60 or 120 mL) (=0.0046%, 0.009%, 0.019%, 0.037% and 0.07% v/v) of Solution C inside a sealed 158 L (42 gallon) plastic bag (n=5 bugs per bag; 3 bags per concentration tested). Solution C vapor concentrations are displayed as relative isopropyl alcohol vapor concentration (determined by gas-chromatographic peak areas analyzed from samples of each bag's head-space). Lines above and below data points indicate standard error mortality of adult bugs and eggs.

Evaporation of Solution C inside empty bags resulted in isopropyl alcohol vapor concentration increasing with the volume of Solution C applied to absorbent cellulose pads. At each volume tested, after 4 hours of evaporation within empty bags, the isopropyl alcohol vapor concentration begins to stabilize as the void-space becomes saturated (FIG. 23). When plastic bags contain books, the maximum concentration of isopropyl alcohol vapor that is detected after evaporation from Solution C dosed pads is significantly lower than that observed inside empty bags (FIGS. 23 and 24). Within book-filled bags, the isopropyl alcohol concentration is maximal after 0.5-4 hours of evaporation, then rapidly decreases and begins to stabilize at 24 hours, remaining stable for the next 4 days (FIG. 24). This rapid decrease in vapor concentration after 24 hours is not observed in empty bags treated with the same volume of Solution C, and the resulting isopropyl alcohol vapor concentration within empty bags remains at a level that is 3-20 times higher than the vapor concentration within book-filled bags. Without being bound by theory, the lowered maximum concentration and rapid decrease of isopropyl alcohol vapor is believed to be caused by the absorbent cellulosic nature of the books within the bag. As isopropyl alcohol evaporates from the pad, the vapor is quickly absorbed by the books and therefore, cannot reach the same maximum concentration observed inside empty bags treated with the same volume of Solution C. Once maximal evaporation has occurred (between 0.5-4 hours), the books continue to absorb vapor (causing a rapid lowering of vapor concentration) until the books become saturated (causing a stable, but lower vapor concentration within the bag). This vapor absorbing phenomenon is likely to occur when bags are filled with other absorbent substrates such as clothing.

Bed bug adults exhibited 100% mortality after 5-day exposure to a relative isopropyl alcohol peak area of 743 emitted from Solution C vapors. Bed bug eggs exhibited 100% mortality after 5-day exposure to a relative isopropyl alcohol peak area of 459. Lower relative peak areas resulted in lower adult bed bug and egg mortality, indicating that a threshold vapor concentration must be maintained to achieve 100% mortality (FIG. 25). These results also indicate that bed bug eggs are affected by lower concentrations of Solution C vapor than are bed bug adults, and emphasize the importance of exposing adults and eggs to an appropriate volume of pesticidal composition for an extended period, taking into account the absorptive nature of the materials within the sealed container.

Example 1.12

Efficacy of Solution C Vapors Against Granary Weevil-Infested Grain Inside a Sealed Bag Groups of 20 healthy adult granary weevils, Sitophilus granarius, were caged above or within the middle of a 100 g column of grain (7.5 cm tall grain column inside a 10 cm×4.5 cm diameter jar) by placing a gas-permeable, nylon mesh barrier within the grain column that filled the jar. Grain and weevils were then sealed into 158 L (42 gallon) plastic bags as a treatment enclosure along with 0, 0.025, 0.05, 0.1, 0.25, 0.5, or 1 ounce (0, 0.75, 1.5, 3, 7.5, 15, or 30 mL) of Solution C liquid dosed onto an absorbent cellulosic pad (Zap pad, =0.0%, 0.0005%, 0.001%, 0.002%, 0.0046%, 0.009% and 0.019% v/v). Weevils and grain jars were each placed inside an empty, transparent plastic garbage bag (158 L, 3 mil thickness) along with 1 polyethylene housing containing a pair of stacked absorbent cellulose pads (each 15.5×11 cm) dosed with 0.025, 0.05, 0.1, 0.25, 0.5, or 1 ounce (0.75, 1.5, 3, 7.5, 15 or 30 mL) of Solution C liquid, or with 1 ounce (30 mL) of water (to serve as an untreated control). Solution C treated pads were placed out of physical contact with insects and grain inside each bag. All insects were exposed to vapors inside sealed bags for 3 days, after which time weevils were observed for mortality. Four replications (20 weevils per jar) were performed for each treatment volume. After 3 days of exposure to Solution C vapors, weevils were removed from bags and grain, and observed for signs of mortality. Dead weevils were defined as those which did not move and were unable to move when gently prodded with forceps. The percent mortality observed after 3 day exposure to each treatment volume was recorded and graphed to determine the minimum effective dose achieved in this system.

Figure 26:
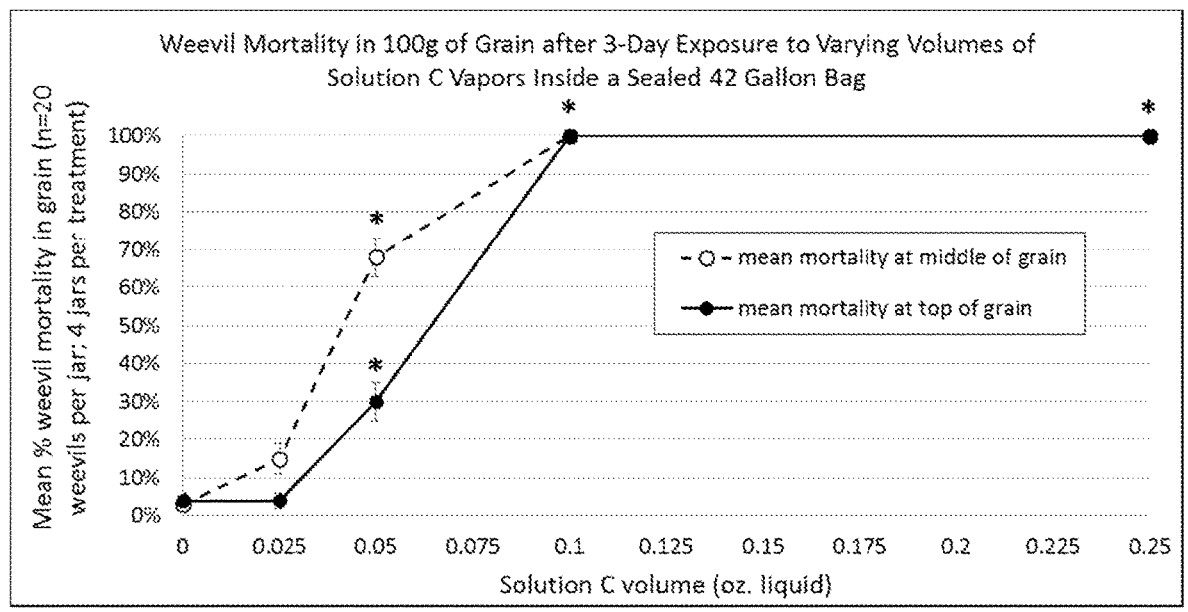
FIG. 26 shows mean mortality of granary weevils, *Sitophilus granarius*, within jars of grain, after exposure to vapors emitted by 0, 0.025, 0.05, 0.075, 0.1, or 0.25 ounces (0.75 mL, 1.5 mL, 2.25 mL, 3 mL, or 7.5 mL) (=0.0046%, 0.009%, 0.019%, 0.037% and 0.07% v/v) of Solution C inside a sealed 158 L (42 gallon) plastic bag (n=20 weevils per jar, 4 jars per treatment volume). Mortality observations were made after 3 days exposure to vapors. Lines above and below data points indicate standard error of mortality and asterisks indicate insect mortality after 24 h vapor-exposure that is significantly higher than control mortality of the same species. (Chi-square test; *p<0.01; 1 d.f.).

Results are shown in FIG. 26, which shows mean mortality of granary weevils, Sitophilus granarius, after exposure to vapors emitted by 0, 0.025, 0.05, 0.075, 0.1, or 0.25 ounces (0, 0.75, 1.5, 2.25, 3, or 7.5 mL) (0.0%, 0.0005%, 0.001%, 0.0015%, 0.002% or 0.0046% v/v). Solution C inside a sealed plastic bag having a volume of 158 L (n=20 weevils per jar, 4 jars per treatment volume). Mortality observations were made after 3 days exposure to vapors. Lines above and below data points indicate standard error mortality and asterisks indicate insect mortality after 24 hour vapor-exposure that is significantly higher than control mortality of the same species. (Chi-square test; *$p<0.01$; 1 d.f.).

Weevils on top of the grain surface exhibited 45%, 30% and 100% mortality when exposed to vapors emitted from 0.025, 0.05, and 0.1 ounce (0.75, 1.5 and 3 mL) of Solution C, respectively. Weevils within the middle of the grain column exhibited 15%, 68% and 100% mortality when exposed to vapors emitted from 0.025, 0.05, and 0.1 ounce (0.75, 1.5 and 3 mL) of Solution C, respectively. All weevils exposed to 0.1 ounce (3 mL) or higher volumes of Solution C exhibited 100% mortality regardless of position within the grain column (FIG. 26). These results indicate that Solution C vapors are capable of entering the void-spaces of a grain column, and can kill weevils residing within those void-spaces.

Example 1.13

Mass-Loss and Relative Isopropyl Alcohol Vapor Concentrations Released from 3 Solution C-Treated Substrates Polyester sponges, cellulose fiber pads and wax pads (n=3 per substrate) were each loaded with 50 grams of Solution C liquid (=0.04% v/v relative to the volume of the treatment enclosure) and allowed to evaporate inside a sealed 158 L (42 gallon) bag. Polyester sponges are an example of a synthetic non-woven polymer. The cellulose fiber pads were Zap pads. The wax pads are an example of a wax substrate, and were made from beeswax, which is a wax derived from an animal. Twenty four hours after each substrate was sealed into a bag, a sample of the bag's head-space volatiles were drawn and analyzed for isopropyl alcohol vapor concentration, and mass-loss from each substrate (due to evaporation of Solution C) was recorded.

After 24 hours, sponge, cellulose-pad and wax substrates exhibited a loss of 18%, 20% and 3% of Solution C due to evaporation, respectively. Each substrate also emitted a relative isopropyl peak area at or above 1860 inside each bag. These results indicate that Solution C evaporates faster from sponge and cellulose fibers, than from wax, but within the sealed system sufficiently lethal vapor concentration accumulated regardless of the substrate used (Table 4).

TABLE 4

Mean mass-loss and relative isopropyl alcohol peak area emitted from sponge, cellulose-pad or wax substrates dosed with 50 g of Solution C placed inside a sealed bag for 24 hours.

| Substrate | Mean % mass loss (g) after 24 hours | Mean relative IPA peak area after 24 hours |
|---|---|---|
| Sponge | 17.8% (±0.5%) | 2835 (±1131) |
| Cellulose Pad | 19.5% (±2.5%) | 1867 (±127) |
| Wax | 2.5% (±0.7%) | 3061 (±627) |

This example demonstrates that sponges and wax can be used as substrates for releasing pesticidal vapors in some embodiments of the present invention. Cellulose-based substrates were selected for further testing in the examples described herein because the density of the tested sponge substrate was lower, and therefore a larger volume of sponge would be required to absorb a particular dose of pesticidal composition; however, other types of sponges may be more absorbent than the tested polyester sponge.

Example 2.0

Selective Efficacy of Pesticidal Vapor on Pests Versus Beneficial Insects

Example 2.1

Efficacy of Pesticidal Vapors Against *Varroa* Mites on Honey Bees

This study was designed to determine whether vapors of a pesticidal composition comprising neem oil and acetophenone would be effective against *varroa* mites (*Varroa destructor*) infested on honey bees (*Apis mellifera*), and if so, what doses of the pesticidal composition would be most effective in differentially killing *Varroa* mites more readily than honey bees.

'Solution A' containing 5.5% cold pressed neem oil by weight, 18.25% acetophenone by weight, and 1.25% ethoxylated castor oil by weight was prepared using water as an emulsifying agent (75% by weight). Live honey bees infested with *varroa* mites were housed within mesh-covered cylinders. The cylinders, containing bees and mites, were placed inside lidded plastic bins (50400 cm$^3$) as a treatment enclosure to approximate the dimensions of a commercial bee hive. Filter papers dosed with either 0.5, 2.0, 5.0, or 10.0 mL of Solution A (=0.001%, 0.004%, 0.01% and 0.02% v/v relative to the volume of the lidded plastic bin that provided a treatment enclosure) were placed within each of the bins with the bees and mites and left to evaporate in ambient conditions for 16 hours (such that the bees and mites inside the mesh cylinders were exposed to vapors of Solution A over this period of time). Filter papers are an example of a naturally occurring polymer, and an example of a non-woven cellulose substrate. Because the bees and mites were confined to the mesh cylinders, they were prevented from having any direct contact with the dosed filter papers throughout the experiment and were only exposed to Solution A via its vapor phase. A negative control bin containing bees and mites was not exposed to any vapors for the duration of the experiment. After 16 hours of exposure, bees and mites were removed from the bins and each was observed microscopically for mortality and signs of toxicity. Experiments were conducted indoors at ambient temperatures of approximately 20-22° C.

Figure 27:
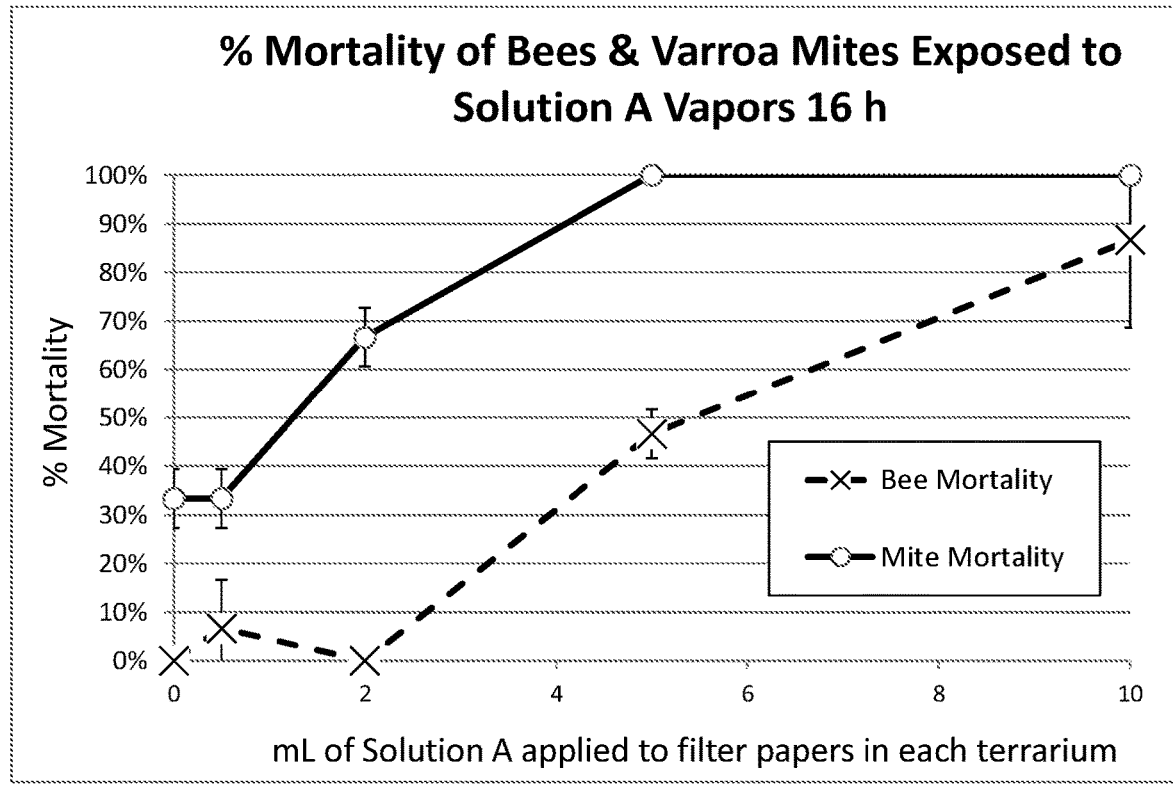
FIG. 27 shows mortality of *Varroa* mites and honey bees exposed to 0, 0.5, 2, 5, or 10 mL of Solution A evaporating from filter papers inside an empty 50400 cm$^3$ bin for 16 hours.

FIG. 27 shows mortality of *Varroa* mites and honey bees exposed to 0, 0.5, 2, 5, or 10 mL of Solution A evaporating from filter papers inside an empty 50400 cm$^3$ bin for 16 hours. As shown in FIG. 27, after 16 hours of exposure to vapors of Solution A, *varroa* mites exhibited higher mortality than bees at all doses that were tested. Respectively, mite mortality and bee mortality were 67% and 0% when 2 ml of Solution A was applied, 100% and 47% with 5 ml of Solution A, and 100% and 87% at 10 ml of Solution A. These volumes correspond to a pesticide concentration of 0.001%, 0.004%, 0.01% and 0.02% v/v, respectively. The bins used as treatment enclosures in this study had tight-fitting lids and were considered air tight. Thus, the bins provided a sealed treatment enclosure.

This example demonstrates the selective activity of Solution A, and in particular the pesticidal activity of the vapors of Solution A as it evaporates from a moistened substrate, to control an undesirable pest arthropod species while not harming a beneficial arthropod species. Although the conditions of this study do not exactly simulate those in a commercial hive, this preliminary experiment has also demonstrated that mites are more susceptible to Solution A vapors than are honey bees, suggesting that Solution A vapors can be useful for selectively controlling *Varroa* mites within bee hives.

Example 2.2

Bee Frame Effect on *Varroa* Mite & Bee Mortality

This study was designed to determine if the presence of bee frames (containing wax, honey and brood) increases or decreases the efficacy of vapors of the pesticidal composition of Example 2.1 against *varroa* mites (*Varroa destructor*) infested on honey bees (*Apis mellifera*). Without being bound by theory, it is believed that wood, honey and/or wax within a bee hive may absorb pesticidal vapors, which reduces the effective pesticidal vapor concentration within a bee hive that provides a treatment enclosure. Experiments were conducted indoors at an ambient temperature of approximately 20-22° C.

'Solution A' containing 5.5% cold pressed neem oil by weight, 18.25% acetophenone by weight, and 1.25% ethoxylated castor oil by weight was prepared using water as an emulsifying agent (75% by weight). Live honey bees infested with *varroa* mites were housed within mesh-covered cylinders. The cylinders, containing bees and mites, were placed inside lidded plastic bins (50400 cm$^3$) as a treatment enclosure to approximate the dimensions of a commercial bee hive. One bin remained empty other than the cylinder containing the mite-infested bees for the duration of the experiment, while a second bin contained 3 bee frames (filled with wax, honey and capped brood). Each of these two bins also received a filter paper dosed with 1 mL of Solution A (0.002% v/v) which was placed above the bee frames (or on a pedestal inside the empty bin) and left to evaporate inside each bin with the bees and mites for 18 hours (such that the bees and mites inside the mesh cylinders were exposed to vapors of Solution A over this period of time). Filter paper is an example of a naturally occurring polymer, and a form of non-woven cellulose substrate.

Because the bees and mites were confined to the mesh cylinders, they were prevented from having any direct contact with the dosed filter papers throughout the experiment and were only exposed to Solution A via its vapor phase. A third bin containing bees infested with mites served as a negative control and was not exposed to any Solution A vapors for the duration of the experiment. After 18 hours of exposure, bees and mites were removed from the bins and each was observed microscopically for mortality and signs of toxicity.

Figure 28:
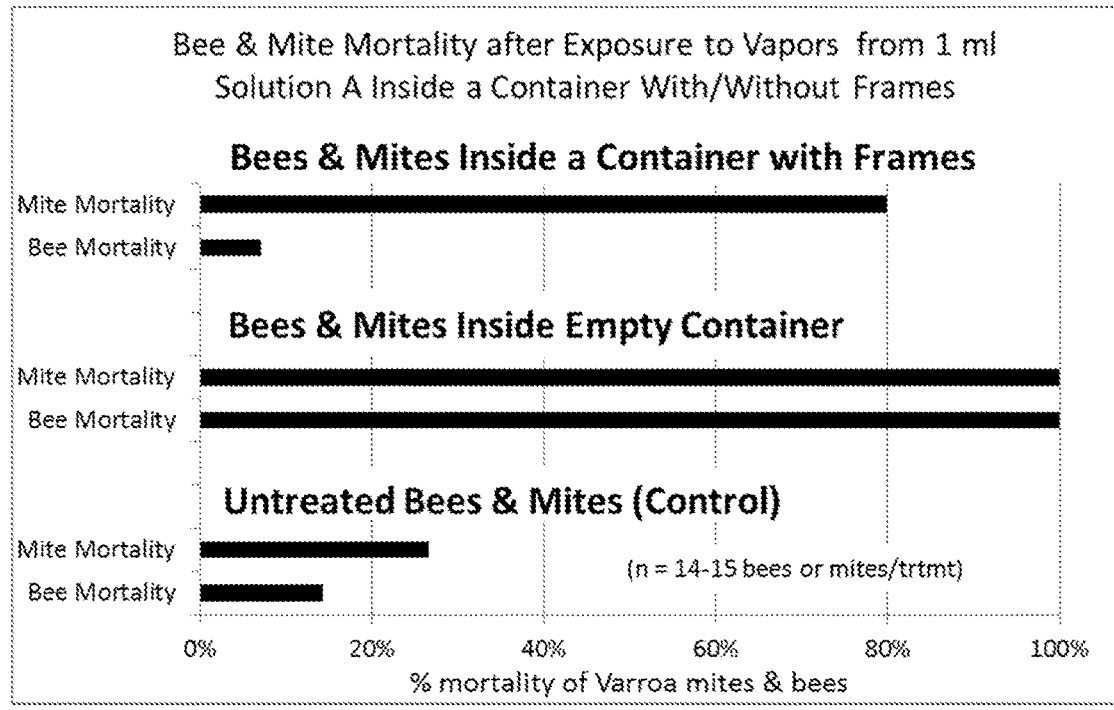
FIG. 28 shows mortality of *varroa* mites and honey bees exposed to 1 mL of Solution A evaporating from filter papers inside a 50400 cm³ bin; either empty or containing three bee frames laden with wax, honey and brood larvae.

FIG. 28 shows mortality of *varroa* mites and honey bees exposed to 1 mL of Solution A evaporating from filter papers inside a 50400 cm$^3$ bin; either empty or containing three bee frames laden with wax, honey and brood larvae. The estimated volume of the three frames laden with honey, larvae and wax is 40972 cm$^3$. Bees that were infested with mites prior to the start of the assay were exposed to Solution A vapors for 18 hours.

As shown in FIG. 28, after 18 hours exposure to vapors emitted from 1 mL of Solution A (0.002% v/v of Solution A applied relative to the volume of the treatment enclosure), bee and *varroa* mite mortality were 7% and 80%, respectively, in bins that contained frames with wax, honey and brood. Comparatively, 100% bee and 100% mite mortality was observed inside empty bins that did not contain wax, honey or brood. These results indicate that the presence of frames with wax, honey and brood greatly decreases the potency of Solution A vapors against bees (possibly due to absorption of vapors by one or more of the materials), and slightly decreases its potency against mites. Therefore, 1 mL or more of Solution A (0.002% v/v Solution A applied versus the treatment volume) may be a safe dose to apply to an actual hive despite high bee mortality in empty bins treated with 1 mL (0.002% v/v) of Solution A.

The bees in Example 2.2 were collected from the same colony as the bees in Example 2.1. However, the bees in Example 2.2 were collected during the fall, when honey and pollen sources are scarce, while the bees in Example 2.1 were collected in the late spring/early summer when the bees had access to an abundance of pollen and honey. Without being bound by theory, it is believed that the greater sensitivity of bees to pesticidal vapors observed in Example 2.2 as compared with Example 1.1 relates to bee health and bee-nutrient access at the time of year that the bees were collected, and thus the applied dose of pesticidal vapour may need to be adjusted to take into account the relative condition of a population of honey bees. However, at both times of collection, the bees were less susceptible to pesticidal vapors than were the *Varroa* mites. Bees in Example 2.3 were tested in mid-spring, and bees in Example 2.4. were tested in summer.

Example 2.3

Field Trials and Assessment of Dose Response

Based on laboratory results and preliminary field trials, 16 bee hives (each comprised of 2 stacked deep brood boxes), containing live honey bees (*Apis mellifera*), were chosen to receive a treatment of 0 ml, 50 ml, 100 ml or 150 ml of Solution B. After subtracting the volume taken up by hive frames and wax inside two stacked brood boxes (estimated to be 81944 cm$^3$), the calculated airspace (i.e. void volume) inside each hive is 24584 cm$^3$ (out of a total possible volume of 106528 cm$^3$ for the 2 stacked brood boxes). The volume of the treatment enclosure is taken as the total volume of 106528 cm$^3$, and the concentration of pesticidal composition (i.e. Solution B) applied in each experiment was respectively 0%, 0.047%, 0.094% or 0.141% v/v, based on the total volume of the hive that provided the treatment enclosure.

Experiments were conducted outdoors at an average ambient temperature in the range of 12-15° C. Without being bound by theory, temperatures inside a bee hive will generally be warmer than the outdoor ambient temperature, because the bees form a tight cluster that vibrates to produce heat. The temperature within the hive can vary depending on the location within the hive relative to this cluster. Thus, it is estimated that the temperature within the hive was in the range of about 12-30° C.

Solution B contained 5.5% cold-pressed Neem oil, 1.25% ethoxylated castor oil, 18.25% acetophenone and 75% isopropyl alcohol (all percentages by weight). Each treatment was applied to two stacked cotton squares (22 cm$^2$) cut from absorbent laboratory mat (each cotton square was approximately 2 mm thick) and covered by a fine aluminum mesh (25 cm$^2$) which was stapled around its periphery to prevent bees from accessing the moistened cotton. Cotton is a naturally occurring polymer, and the cotton laboratory mat is an example of a non-woven cellulose substrate. An appropriate dose of treatment formulation was applied to each cotton square, which was then immediately placed above the brood frames of a bee hive, and then covered by the hive's inner and outer lid to provide a treatment enclosure that is somewhat permeable to pesticidal vapors. Hives were treated when the ambient temperature was 12° C., and before 9:00 am to ensure all bees were present in the hive. Hives treated with 50 or 100 ml doses of Solution B received a single stacked square placed centrally above frames, whereas hives treated with 150 ml Solution B formulation received two stacked squares placed side-by side above frames. No attempt was made to close or reduce hive entrances during treatment but mite trap boards were fitted directly below the lower brood box just before the treatment was applied. The mite boards were left in place for 2 weeks prior to treatment and for 2 weeks following treatment (with replacement every 2 days) and mite drop onto boards was counted every 2 days to determine natural mite mortality and mortality resulting from treatments. The Solution B-treated cotton squares were left in each hive for 4 days, then were removed after it was determined the treatments were no longer increasing the mite-drop counts. Insertion of the mite board restricted air flow through the bottom of the hives, although other openings such as hive entrances and air gaps were left open. Thus, the bee hives were partially sealed. The opening at the bottom of the hive was fully open (approximately 2 cm high and 20 cm wide). Air can also flow through thin air gaps (typically less than about 0.5 mm) where the brood boxes and lid of the hive meet.

Mites within bee hives are located on the worker bees or within capped brood cells (mites within these cells emerge when bees emerge from the cells). Therefore, bee and capped brood cell populations were counted using photographs taken of each frame within each hive, and mite population in each hive was estimated based on mite numbers collected from worker bees in each hive (n=500 bees total), from mite numbers collected from capped brood cells collected from each hive (n=500 cells total), and from the following formula:

$$\frac{\text{mite drop}}{(\text{bees} \times \text{mites}_p) + [(\text{cells} \times r_{emergence}) \times \text{mites}_c]} \quad (1)$$

where, mite drop=number of dead mites found on mite boards within 24 hours; bees=observed number of bees per hive; mites$_p$=observed # of phoretic mites/bee;

cells=observed number of capped brood cells per hive; $r_{emergence}$=0.083–the calculated daily emergence rate of bees and mites per capped brood cell; $mites_c$=estimated number of mites per capped brood cell as determined from samples.

Figure 29:
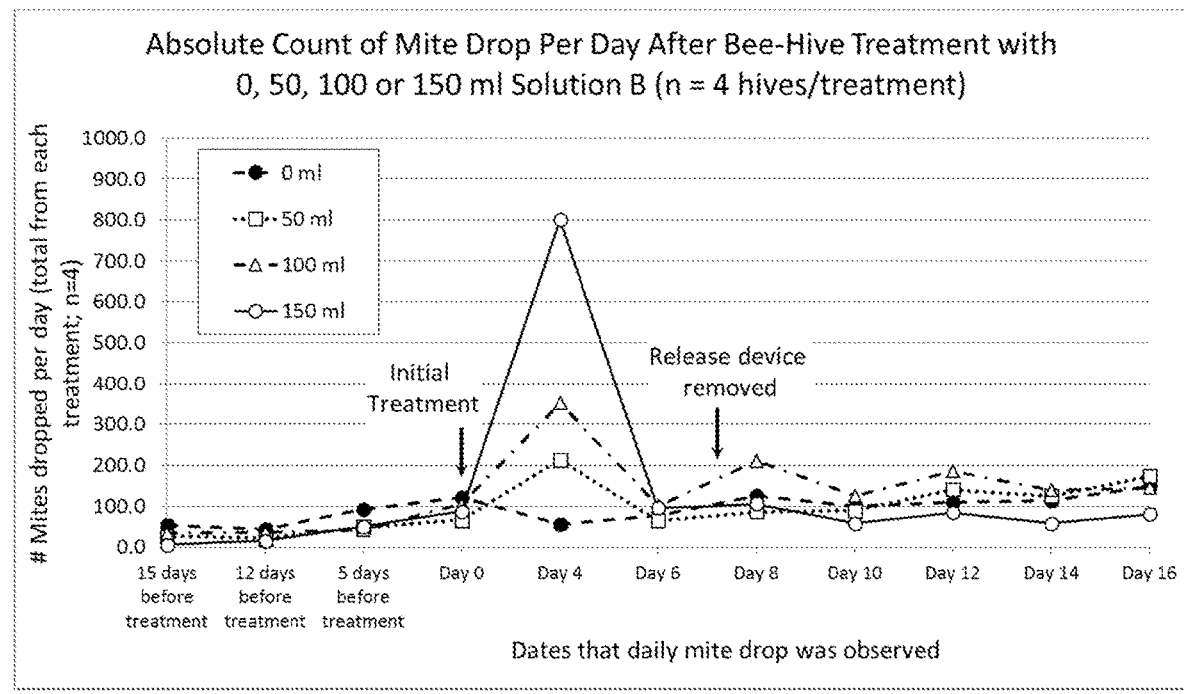
FIG. 29 shows the mortality of phoretic mites in hives treated with 0 ml, 50 ml, 100 ml or 150 ml of Solution B formulation (pre- and post-treatment mortality shown).

FIG. 29 shows the one-month mortality of phoretic mites in hives treated with 0 ml, 50 ml, 100 ml or 150 ml of Solution B (0%, 0.047%, 0.094% or 0.141% v/v, pre- and post-treatment mortality shown). Bee hive treatment with 0 ml Solution B (negative control) caused an average mite drop of 55 mites/day (compared to 78 mites/day pre-treatment); 50 ml Solution B caused an average drop of 213 mites/day (compared to 41 mites/day pre-treatment); 100 ml Solution B caused a drop of 352 mites/day (compared to 55 mites/day pre-treatment); 150 ml of Solution B caused a drop of 801 mites/day (compared to 40 mites/day pre-treatment) (FIG. 29).

Figure 30:
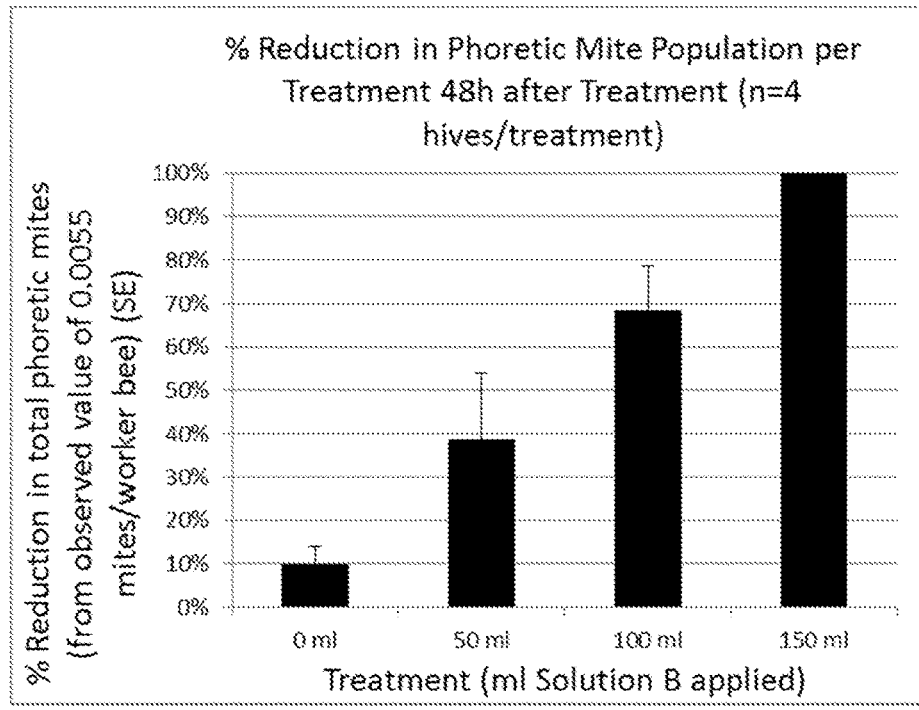
FIG. 30 shows the percent mortality of phoretic mites on worker bees in hives as a result of treatment with 0 ml, 50 ml, 100 ml or 150 ml of Solution C after 48 hours.
Figure 31:
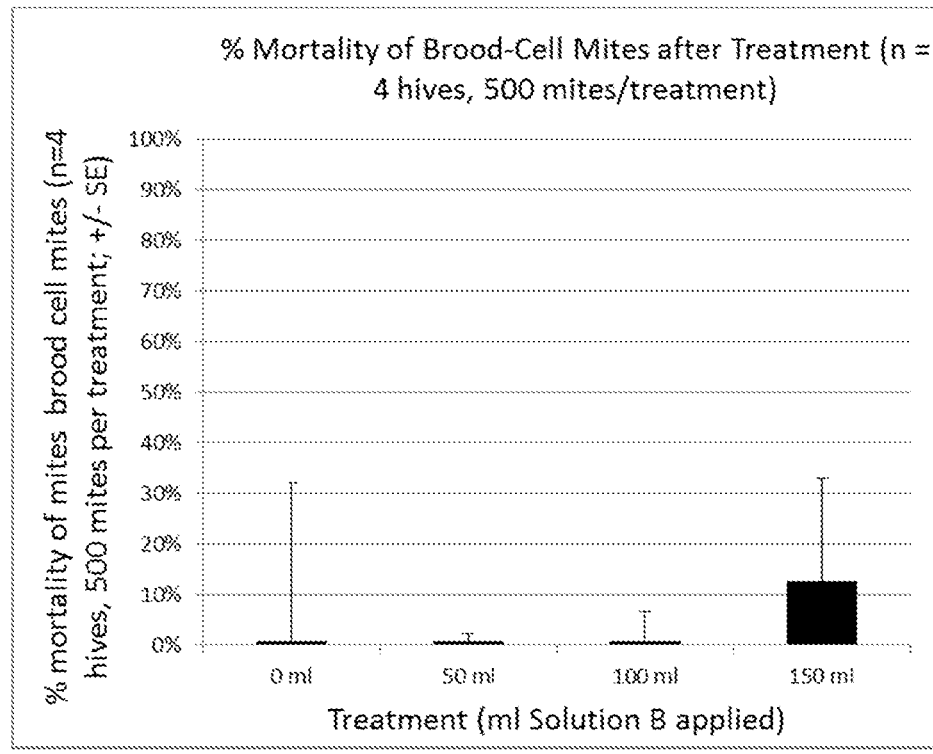
FIG. 31 shows the percent mortality of mites emerging from capped brood cells from hives after treatment with 0 ml, 50 ml, 100 ml or 150 ml of Solution C. These values indicate the total mortality of brood cell mites within hives after exposure to each treatment.

From observed mite mortality and calculated bee and mite populations, it was determined that 0 ml, 50 ml, 100 ml and 150 ml Solution B treatments (0%, 0.047%, 0.094% or 0.141% v/v) killed 10%, 39%, 69% and 100% of phoretic mites, respectively within 48 hours (FIG. 30). However, mites emerging from capped brood cells were not affected by the 0 ml, 50 ml and 100 ml treatments, but the 150 ml treatment killed 12% of the emerging mites (FIG. 31). Without being bound by theory, it is believed that newly emerged mites are not exposed to 0-100 ml treatments because those treatments evaporate before the new mites emerge from cells, whereas the 150 ml treatments remain long enough to affect some of the early emerging mites.

Observations of worker bee populations before and after treatment indicate that little to no worker bee death occurred as a result of any of the treatments. Bee health was monitored for one month following the initial treatments.

Example 2.4

Assessment of *Varroa* Mite Mortality and Bee Health after Exposure to Solution C or 65% Formic Acid 23 honey bee colonies (*Apis mellifera*) were assessed. Each hive was inoculated with *Varroa* mites (*Varroa destructor*) by introducing *Varroa*-infested brood comb 3 months prior to testing. For 2 weeks prior to treatment, mite drop from each hive was counted every four days from sticky boards placed below each hive.

Experiments were conducted outdoors at an average ambient temperature in the range of 18-20° C. Without being bound by theory, temperatures inside a bee hive will generally be warmer than the outdoor ambient temperature, because the bees form a tight cluster that vibrates to produce heat. The temperature within the hive can vary depending on the location within the hive relative to this cluster. Thus, it is estimated that the temperature within the hive was in the range of about 18-30° C.

16 hives received a treatment of 100 ml of water (negative control), 100 ml Solution B (5.5% neem oil, 1.25% ethoxylated castor oil, 18.25% acetophenone, 75% isopropyl alcohol) (0.094% v/v), or 30 ml of 65% formic acid (positive control) (n=4 hives per treatment). Each treatment was applied to two stacked cotton pads (having an area of 22 cm²) cut from absorbent laboratory mat (each cotton pad was approximately 2 mm thick) and covered by a fine aluminum mesh (25 cm²) which was stapled around its periphery to prevent bees from accessing the moistened cotton. Cotton is a naturally occurring polymer, and the absorbent laboratory mat is an example of a non-woven cellulose substrate. An appropriate dose of treatment formulation was applied to each cotton pad, which was then immediately placed above the brood frames of the top-most brood box (directly below the hive's inner lid) in each bee hive, and then covered by the hive's inner and outer lid to provide a treatment enclosure. The ambient temperature outside the hive during treatments was 20° C. No attempt was made to close or reduce hive entrances during treatment but sticky mite boards were fitted directly below the lower brood box just before the treatment was applied. Average outside temperatures ranged from 18-22° C. during the treatment and observation period.

Mite boards were left in place for 5 weeks following treatment (with replacement every 2 days) and mite drop onto boards was counted every 2 days to determine natural mite mortality, treatment-mortality, and duration of treatment effect. The treated cotton pads were left in each hive for 8 days, then were removed once it was determined that mite mortality had fallen to pre-treatment levels. Following removal of treated cotton pads, an Amitraz clean-up treatment was added to each hive by suspending 2 Apivar-strips (3.3% Amitraz) between frames within each brood chamber for 21 days. Mite mortality on sticky boards from each hive was counted weekly for the duration of the Amitraz treatment. The purpose of the 21 day Amitraz clean-up treatment was to kill and measure the number of mites that were present during application of vapor treatments but were not killed by vapor treatments.

The efficaciousness of vapor treatments against mites was determined by the method of Melathopoulos et al. (2000). The proportion of mites killed by each treatment ($P_{varroa}$) was measured by counting mite drop onto sticky boards placed below each hive for 8 days following the vapor treatment, as compared to the total mite population (phoretic and brood-bound mites) present within each hive. Total mite population was measured by counting mortality of mites on sticky boards killed by vapor treatment ($M_{treatment}$) in addition to those killed by Amitraz clean-up treatment ($M_{evaluation}$). The clean-up treatment was intended to kill any mites that may have survived the experimental vapor treatment, including those that emerged from brood-cells following removal of experimental vapor treatments.

$$P_{varroa} = \frac{M_{treatment}}{M_{treatment} + M_{evaluation}} \qquad (2)$$

Bee health was measured for 1 month following initial treatments. Worker bee health was measured by photographing worker behavior on hive exteriors each day following treatment, and by counting worker mortality on drop sheets placed in front of hive entrances. One week following treatment, brood mortality was assessed by removing a single frame from each hive, and brood was manually uncapped in order to observe movement of pupae and assess mortality. Brood emergence was measured by photographing a small patch of newly-capped brood (100-200, 10 day-old brood) within each hive prior to treatment. Photographed brood were then removed from each hive 8 days after treatment and were incubated in laboratory rearing chambers for an additional 14 days. All worker bees and bees newly emerged from brood cells were removed daily to prevent bees from uncapping brood on frames. Brood patches were then photographed a second time and numbers of uncapped cells (indicating brood emergence) were counted. Each treated hive was also inspected weekly for evidence of oviposition and queen mortality.

Figure 32:
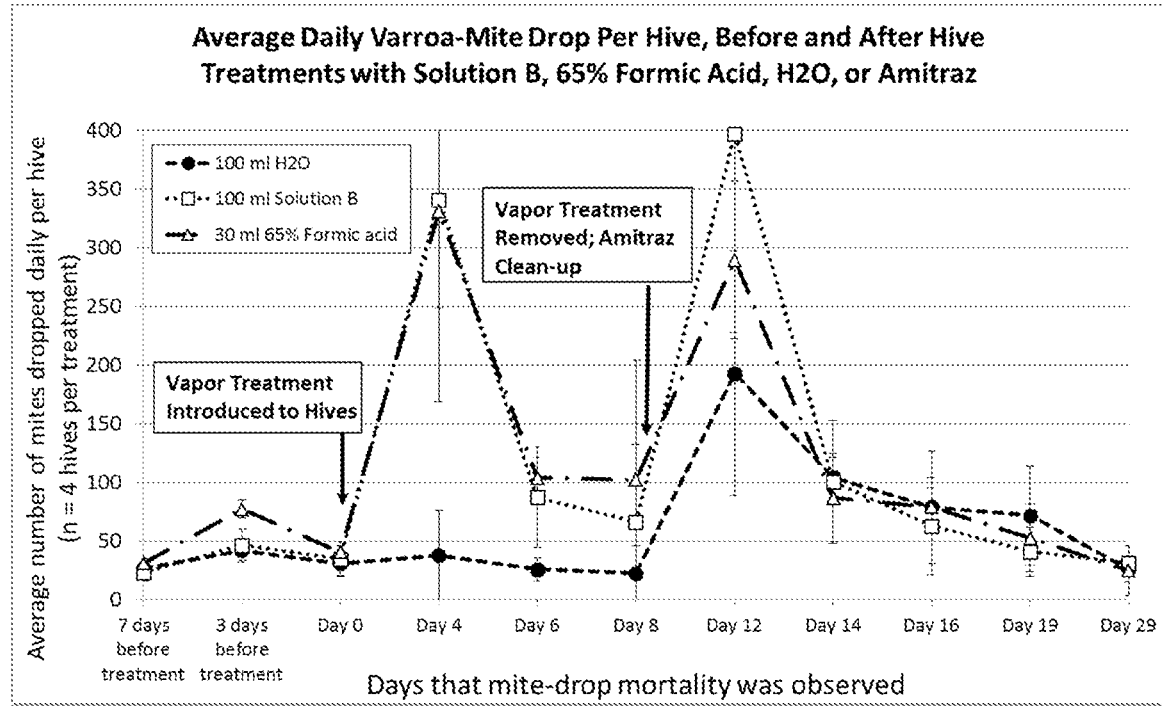
FIG. 32 shows the average daily Varroa mite drop in bee hives observed from sticky boards for two weeks prior to treatments (mite drop 1 week prior to treatment shown), 8 days during vapor treatment, and for three weeks following Amitraz clean-up treatment following treatment with Solution B, 65% formic acid, or water.
Figure 33:
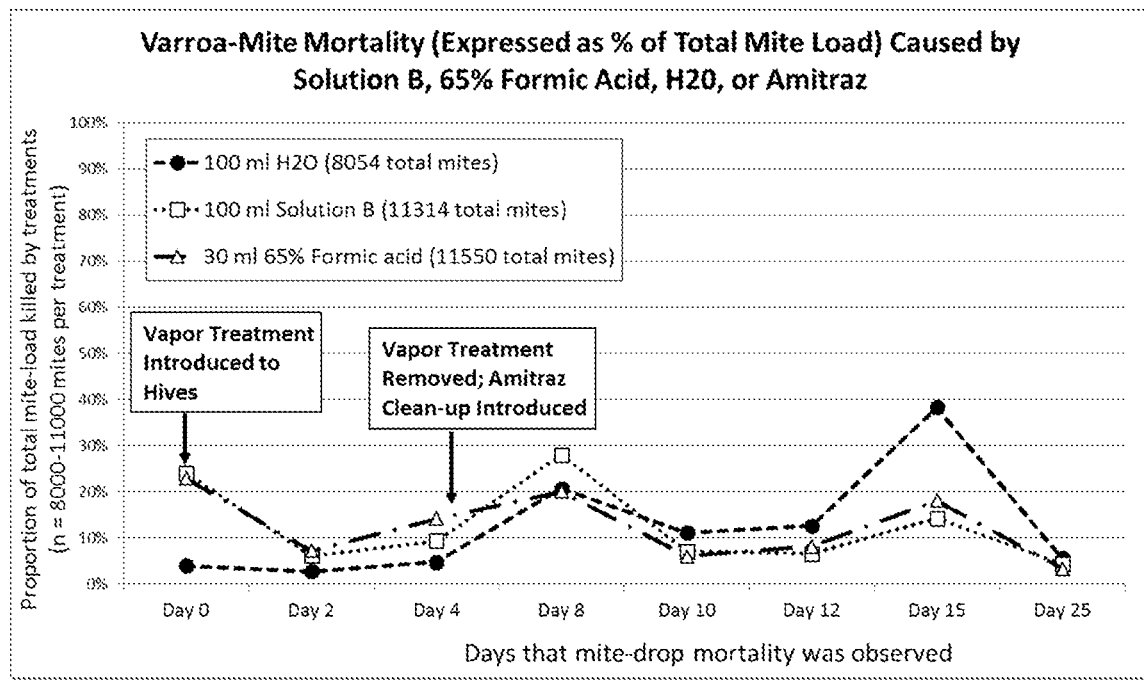
FIG. 33 shows total Varroa mite mortality (mortality of phoretic and brood-cell mites, expressed as % of total mite load) observed from sticky boards during vapor treatment, and following Amitraz clean-up treatment. Mites were counted and mite-boards were replaced in each hive every 2-5 days (n=4 hives per treatment).

FIG. 32 shows average daily *Varroa* mite drop observed from sticky boards for 1 week prior to vapor treatments, 8 days during vapor treatment, and for 3 weeks following Amitraz clean-up treatment. Mites were counted and mite-boards were replaced in each hive every 2-5 days. Treatments consisted of placing saturated cotton pads above the frames of the top-most brood box (immediately below the hive's inner lid; two brood chambers and 1 honey super, stacked) for 8 days (n=4 hives per treatment). Lines above and below data points indicate standard error mite of drop at each observation time. FIG. 33 shows *Varroa* mite mortality (expressed as % of total mite load) observed from sticky boards during vapor treatment, and for 3 weeks following Amitraz clean-up treatment. Mites were counted and mite-boards were replaced in each hive every 2-5 days (n=4 hives per treatment).

Figure 34:
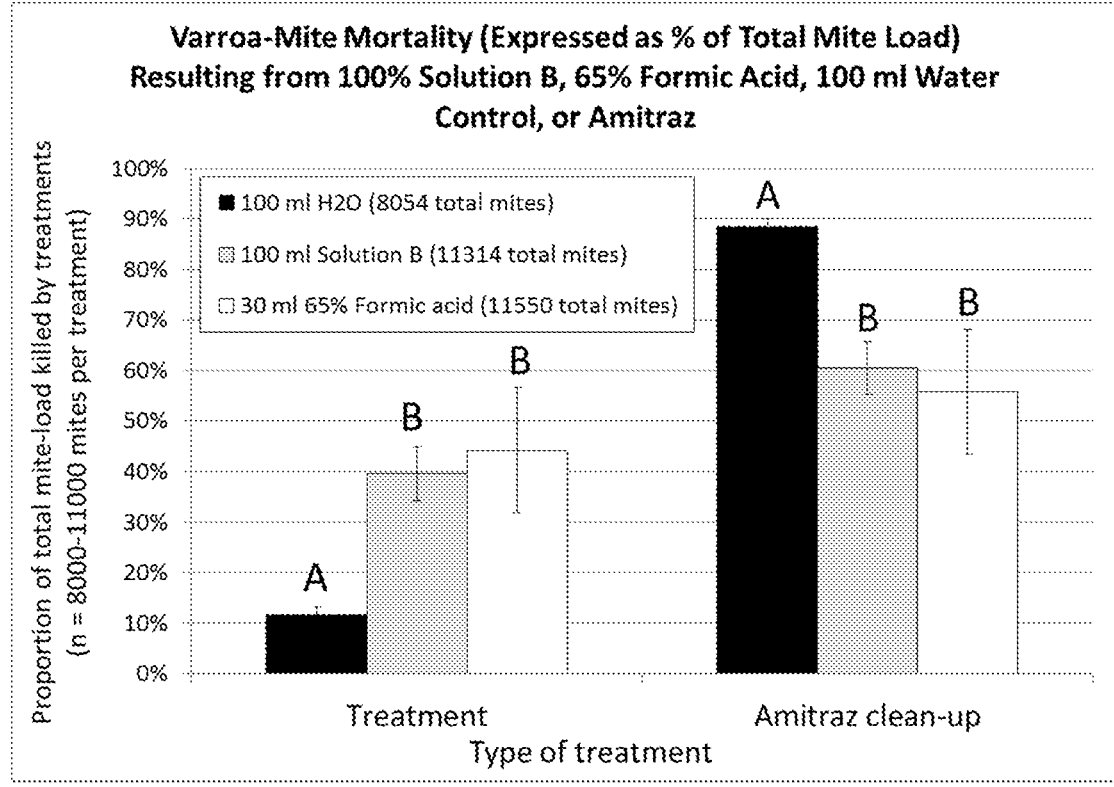
FIG. 34 shows Varroa mite mortality expressed as a percentage of total mite load resulting from treatment with Solution B, 65% formic acid, or water for 8 days or treatment with Amitraz. Identical letters above bars indicate mite mortality which was not statistically different (t-test, $p<0.05$, n=8000-11000 mites per treatment).
Figure 35:
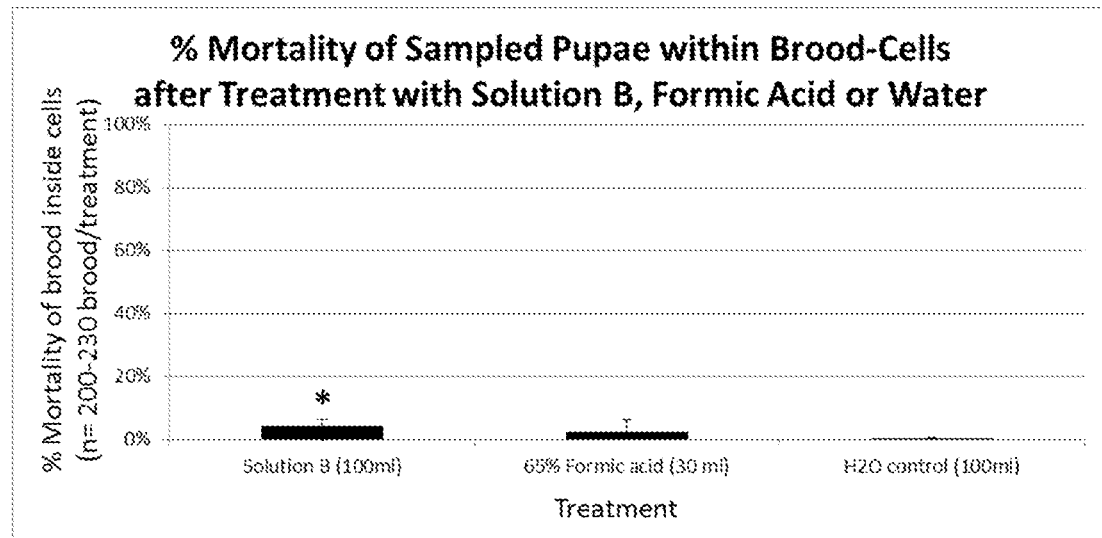
FIG. 35 shows the percent mortality of manually uncapped bee pupae 1 week after treatment with vapors from 100 mL of Solution B, 30 mL of 65% formic acid, or 100 mL of $H_2O$.
Figure 36:
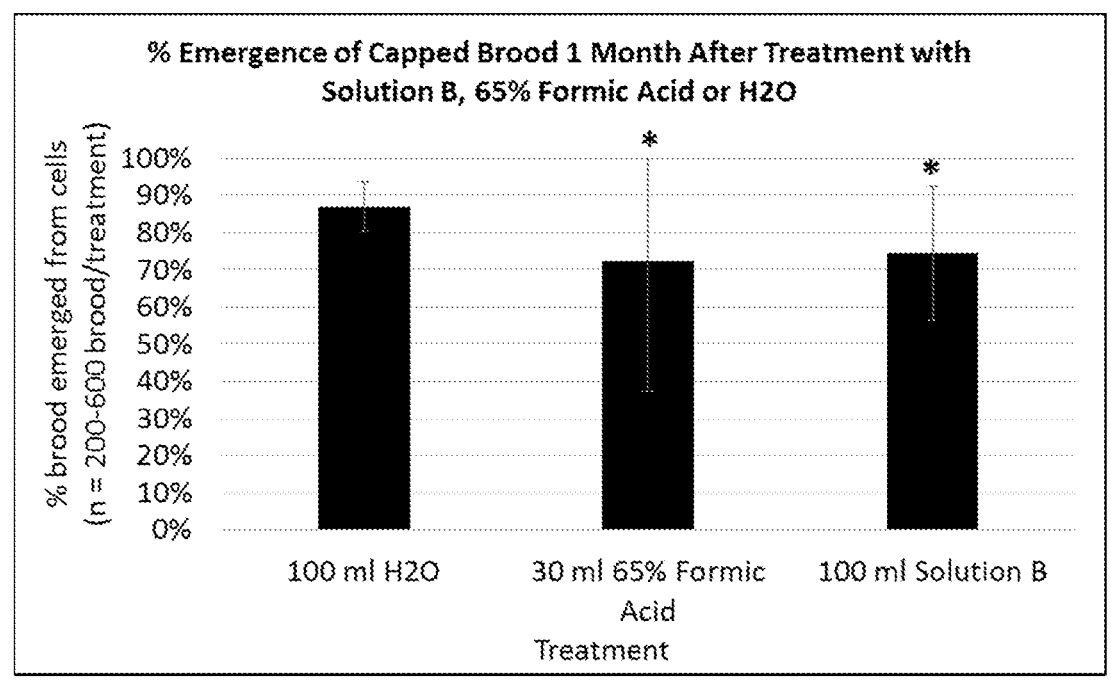
FIG. 36 shows the percent emergence of 10 day-old, capped bee pupae 1 month after treatment with vapors from 100 mL of Solution B, 30 mL of 65% formic acid, or 100 mL of $H_2O$.

FIG. 34 shows *Varroa* mite mortality for various vapor treatments after 8 days of exposure. The left set of bars show the proportion of mites killed by each vapor treatment ($M_{treatment}$) compared to the total mite load of each hive (all phoretic mites and brood-cell bound mites); the right set of bars show proportion of total mite load not killed by experimental vapor treatments (i.e. all remaining mites killed by the Amitraz clean-up treatment; $M_{evaluation}$). The proportion of mites killed by treatments ($P_{varroa}$) was calculated using the method of Melathopoulos et al. (2000): $P_{varroa} = M_{treatment}/(M_{treatment} M_{evaluation})$. Lines above bars indicate standard error of mite mortality of each treatment. Bars with different letters indicate treatments with significantly different mite mortality (t-test, $p<0.05$, n=4 hives per treatment) during vapor treatment, or within those same hives after Amitraz clean-up treatment. FIG. 35 shows the percent mortality of manually uncapped bee pupae 1 week after treatment with vapors from 0.094% v/v Solution B, 65% formic acid, or $H_2O$. Lines above bars indicate standard error of % mortality; asterisks above bars indicate treatment mortality that is significantly higher than control mortality (Chi square test; $p<0.05$; 1 d.f.; n=200-230 brood per treatment). FIG. 36 shows the percent emergence of 10 day-old, capped bee pupae 1 month after treatment with vapors from 0.094% v/v Solution B, 65% formic acid, or $H_2O$. Lines above bars indicate standard error of % mortality; asterisks above bars indicate treatment mortality that is significantly higher than control mortality (Chi square test; *$p<0.05$; 1 d.f.; n=250-500 brood per treatment).

Solution B vapors killed 40% of the total mite-population (11314 mites) within treated hives; formic acid vapors killed 44% of the total mite-population (11550 mites); $H_2O$ vapors (negative control) also killed 12% of the total mite population (8054 mites) within treated hives (FIGS. 32-34). These results indicate that vapors emitted by 100 ml (0.094% v/v) of Solution B and 30 ml 65% formic acid demonstrate similar efficacy against *Varroa* mites. After applying each vapor treatment, almost all mite mortality was observed within the first 48 hours, after which time mortality fell to pre-treatment levels (FIG. 32), indicating that vapors were very effective at killing mites that were living phoretically at the time of treatment, and that those vapors dissipated within 48 hours. In addition, 29 days after the initial vapor treatments, the total population of mites surviving within Solution B—or formic acid-treated hives (as determined from the number of mites killed by Amitraz clean-up treatment) was significantly lower than the total population of mites surviving within $H_2O$-treated hives (FIGS. 33 and 34), indicating that Solution B and formic acid treatments did significantly reduce *Varroa* populations over a longer period. Previous tests of vapor penetration into brood cells, as well as field trials indicate that Solution B and formic acid vapors can kill mites within brood-cells if the vapor is highly concentrated. Unfortunately, increasing the vapor concentration of Solution B or formic acid risks killing brood, workers and queen bees. A possible solution that could increase the effectiveness for these fast-evaporating vapors is to incorporate them into a sustained-release matrix, or into a timed-release device such as described herein that allows release of periodic, short bursts or sustained release of effective vapor concentrations throughout the 21 day *Varroa* mite life cycle.

Within 30 minutes of applying treatments, 2 of the hives treated with Solution B exhibited heavy bearding and no bearding was observed in any other hives. At 48 hours post-treatment one of the Solution B-treated hives and 2 of the formic acid-treated hives exhibited mild bearding, which disappeared after 4 days. The proportion of brood surviving treatment with Solution B, formic acid, and $H_2O$ vapors was 96%, 98%, and 100%, respectively (FIG. 35). Brood emergence was significantly lower after Solution B and formic acid treatments (76% and 72% emergence, respectively) compared to control emergence (87%) (FIG. 36). Weekly observations of hives indicated that oviposition was not affected by any of the treatments, and that queen survival was 100% for all treatments in all hives except for hive #6 which had lost its queen in the week preceding treatment.

The results of this example indicate that vapors emitted by 100 ml (0.094% v/v) of Solution B or 30 ml of 65% formic acid did not harm queens and did not kill a biologically significant number of brood. However, it should be noted that statistically, the 4% brood mortality caused by Solution B was significantly higher than 0% mortality in controls (Chi square test; $p<0.05$) (brood mortality caused by Solution B and formic acid were not significantly different).

While a number of exemplary aspects and embodiments have been discussed above, those of skill in the art will recognize certain modifications, permutations, additions and sub-combinations thereof. To the extent that they are not mutually exclusive, embodiments described above can be combined with one another to yield further embodiments of the invention. It is therefore intended that the following appended claims and claims hereafter introduced are not to be limited by the exemplary embodiments set forth herein, but are to be given the broadest interpretation consistent with the specification as a whole.

What is claimed is:
1. A method of killing a pest, the method comprising:
   providing a treatment enclosure containing pests or their eggs, or an article infested with pests or their eggs, the treatment enclosure having a volume of between 70 L and 1200 L;
   providing a substrate impregnated with a pesticidal composition; and
   passively releasing pesticidal vapors of the pesticidal composition from the substrate within the treatment enclosure for a treatment period, wherein the pesticidal composition comprises neem oil;
   wherein the concentration of neem oil in the pesticidal composition comprises in the range of about 0.00055% to 0.013% by volume per volume of the treatment enclosure.
2. A method as defined in claim 1, wherein:
   the pesticidal vapors are released within the treatment enclosure for the treatment period so that a void space of the treatment enclosure begins to saturate within 4 hours and reaches saturation within 24 hours as mea- sured by gas chromatography using a diluent as a marker, wherein the diluent optionally comprises isopropyl alcohol.

3. A method as defined in claim 1, wherein the treatment enclosure is airtight.

4. A method as defined in claim 1, wherein the treatment enclosure is at least partially permeable to pesticidal vapors.

5. A method as defined in claim 4, wherein the pests comprise *varroa* mites and the treatment enclosure comprises a bee hive, and wherein the concentration of the neem oil in the composition comprises in the range of about 0.00055% to 0.00825% by volume per volume of the bee hive, and the concentration of acetophenone in the composition comprises in the range of about 0.001825% to 0.0275% by volume per volume of the bee hive.

6. A method as defined in claim 1, wherein:
the treatment enclosure has a volume of between 70 L and 200 L and the substrate comprises between 10 mL and 200 mL of the pesticidal composition; and
wherein the pests comprise terrestrial arthropods.

7. A method as defined in claim 6, wherein the pesticidal composition comprises acetophenone, and the concentration of acetophenone is in the range of about 0.001825% to 0.0365% by volume per volume of treatment enclosure in which it is applied.

8. A method as defined in claim 1, wherein the composition comprises a diluent, and wherein a peak area of the diluent as measured by gas chromatography reaches at least 750 within 24 hours.

9. A method as defined in claim 8, wherein the diluent comprises isopropyl alcohol.

10. A method as defined in claim 1, wherein the pesticidal vapors of the pesticidal composition are released from the substrate so that a void space of the treatment enclosure begins to saturate within 4 hours and reaches saturation within 24 hours.

11. A method as defined in claim 1 for controlling eggs of a pest, wherein the step of providing a treatment enclosure containing pests or their eggs, or an article infested with pests or their eggs comprises providing a treatment enclosure containing the eggs of the pest or an article infested with the eggs of the pest; and wherein the pest comprises a terrestrial arthropod.

12. A method as defined in claim 11 wherein the pesticidal composition comprises a diluent, and wherein a peak area of the diluent as measured by gas chromatography is at least 450 after 5 days.

13. A method as defined in claim 12, wherein the diluent comprises isopropyl alcohol.

14. A method as defined in claim 1, wherein the treatment enclosure comprises a volume of between 70 L and 200 L and the substrate comprises between 10 mL and 200 mL of pesticidal composition.

15. A method as defined in claim 1, wherein the substrate comprises a volume of the pesticidal composition in a range of 10 mL to 100 mL of the pesticidal composition per 100 L volume of the treatment enclosure.

16. A method as defined in claim 1, wherein the step of providing a substrate impregnated with a pesticidal composition comprises providing the substrate within a housing, the housing comprising a window or series of apertures for releasing pesticidal vapors from the substrate and a peel strip or resealable rigid opening that initially sealingly covers the window or series of apertures, and further comprises opening the peel strip or resealable rigid opening.

17. A method as defined in claim 1, wherein the treatment enclosure comprises a structure for fully or partially sealing the treatment enclosure, the structure comprising a flexible outer layer that is impermeable or substantially impermeable to pesticidal vapors.

18. A method as defined in claim 17, further comprising killing the pest inside the treatment enclosure.

19. A method of killing a pest, the method comprising:
providing a treatment enclosure containing pests or their eggs, or an article infested with pests or their eggs; and
releasing pesticidal vapors within the treatment enclosure for a treatment period, the pesticidal vapors being released from a composition comprising neem oil wherein:
the treatment enclosure has a volume of between 70 L and 1200 L; and
the step of releasing pesticidal vapors within the treatment enclosure comprises:
providing a substrate impregnated with a pesticidal composition; and
passively releasing pesticidal vapors of the pesticidal composition from the substrate within the treatment enclosure for a treatment period, wherein the pesticidal composition is applied at a concentration in the range of 0.01% to 0.2% vol/vol relative to the volume of the treatment enclosure in which it is applied;
wherein the pests comprise terrestrial arthropods.

20. A method as defined in claim 19, wherein the pesticidal composition comprises acetophenone at a concentration in the range of about 0.001825% to 0.0365% by volume per volume of treatment enclosure in which it is applied.

21. A method as defined in claim 20, wherein the concentration of the neem oil is in the range of about 0.00055% to 0.013% by volume per volume of treatment enclosure in which it is applied.

22. A method as defined in claim 19 for controlling eggs of a pest, wherein the step of providing a treatment enclosure containing pests or their eggs or an article infested with pests or their eggs comprises providing the treatment enclosure containing the eggs of the pest or an article infested with the eggs of the pest.

23. A method as defined in claim 22, wherein the pesticidal composition comprises acetophenone at a concentration in the range of about 0.001825% to 0.0365% by volume per volume of treatment enclosure in which it is applied.

24. A method as defined in claim 23, wherein the concentration of the neem oil is in the range of about 0.00055% to 0.011% by volume per volume of treatment enclosure in which it is applied.

25. A method of killing a pest, the method comprising:
providing a treatment enclosure containing pests or their eggs, or an article infested with pests or their eggs, the treatment enclosure comprising a structure for fully or partially sealing the treatment enclosure, the structure comprising a flexible outer layer that is impermeable or substantially impermeable to pesticidal vapors;
providing a substrate impregnated with a pesticidal composition; and
passively releasing pesticidal vapors of the pesticidal composition from the substrate within the treatment enclosure for a treatment period, wherein the pesticidal composition comprises neem oil;
wherein the concentration of neem oil in the pesticidal composition comprises in the range of about 0.00055% to 0.013% by volume per volume of the treatment enclosure.

26. A method of controlling a pest by killing the pest, the method comprising:

providing a treatment enclosure containing pests or their eggs, or an article infested with pests or their eggs, the treatment enclosure comprising a structure for fully or partially sealing the treatment enclosure, the structure comprising a flexible outer layer that is impermeable or substantially impermeable to pesticidal vapors;

providing a substrate impregnated with a pesticidal composition; and passively releasing pesticidal vapors of the pesticidal composition from the substrate within the treatment enclosure for a treatment period, wherein the pesticidal composition comprises neem oil.

\* \* \* \* \*